United States Patent
Braje et al.

(10) Patent No.: US 9,617,226 B2
(45) Date of Patent: Apr. 11, 2017

(54) FUSED HETEROCYCLIC OR CARBOCYCLIC COMPOUNDS CARRYING A SUBSTITUTED CYCLOALIPHATIC RADICAL AND USE THEREOF FOR TREATING VASOPRESSIN-RELATED DISEASES

(71) Applicant: AbbVie Deutschland GmbH & Co. KG, Wiesbaden (DE)

(72) Inventors: Wilfried Braje, Ludwigshafen (DE); Jayne Froggett, Ludwigshafen (DE); Hervé Geneste, Ludwigshafen (DE); Wilfried Hornberger, Ludwigshafen (DE); Katja Jantos, Ludwigshafen (DE); Andreas Kling, Ludwigshafen (DE); Marcel van Gaalen, Göttingen (DE)

(73) Assignee: AbbVie Deutschland GmbH & Co. KG, Wiesbaden (GB)

( * ) Notice: Subject to any disclaimer, the term of this patent is extended or adjusted under 35 U.S.C. 154(b) by 0 days.

(21) Appl. No.: 14/845,727

(22) Filed: Sep. 4, 2015

(65) Prior Publication Data
US 2016/0068494 A1    Mar. 10, 2016

Related U.S. Application Data

(60) Provisional application No. 62/046,527, filed on Sep. 5, 2014.

(51) Int. Cl.
C07D 239/91 (2006.01)
C07D 401/12 (2006.01)
C07D 403/12 (2006.01)
C07D 455/02 (2006.01)
C07D 491/107 (2006.01)

(52) U.S. Cl.
CPC ......... *C07D 239/91* (2013.01); *C07D 401/12* (2013.01); *C07D 403/12* (2013.01); *C07D 455/02* (2013.01); *C07D 491/107* (2013.01)

(58) Field of Classification Search
CPC .. C07D 239/91; C07D 401/12; C07D 403/12; C07D 455/02; C07D 491/107
See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| WO | 9507271 A1 | 3/1995 |
| WO | 9710223 A1 | 3/1997 |
| WO | 2005099353 A2 | 10/2005 |
| WO | 2006008754 A1 | 1/2006 |
| WO | 2006095014 A1 | 9/2006 |
| WO | 2008033764 A2 | 3/2008 |
| WO | 2008071779 A1 | 6/2008 |
| WO | 2010037129 A1 | 4/2010 |
| WO | 2011045258 A1 | 4/2011 |
| WO | 2012154760 A1 | 11/2012 |

OTHER PUBLICATIONS

Napier, et al., Synthesis as SAR studies of novel 2-(6-aminomethyl-aryl-2-aryl-4-oxo-quinazolin-3(4H)-yl)acetamide Vasopressin V1b receptor antagonists, Bioorganic & Medicinal Chem. Letters 21(12), 3813-3817 (2011).*

Alam M.M., et al., "Synthetic Communications," An International Journal for Rapid Communication of Synthetic Organic Chemistry, 2003, vol. 33 (1), pp. 59-63.

Beylot M. et al., "In Vivo Studies of Intrahepatic Metabolic Pathways," Diabetes Metabolism, 1997, vol. 23 (3), pp. 251-257.

Blagojevic N., et al., "Role of heavy water in Boron Neutron Capture Therapy," in: Dosimetry & Treatment Planning for Neutron Capture Therapy, Zamenhof R, et al., Edition, 1994, Advanced Medical Publishing, pp. 125-134.

Blake, M. I. et al., "Studies With Deuterated Drugs," Journal of Pharmaceutical Sciences, 1975, vol. 64 (3), pp. 367-391.

Blanchard R.J., et al., "AVP V1B Selective Antagonist SSR149415 Blocks Aggressive Behaviors in Hamsters," Pharmacology Biochemistry and Behavior, 2005, vol. 80 (1), pp. 189-194.

(Continued)

Primary Examiner — Erich A Leeser
(74) Attorney, Agent, or Firm — Neal Gerber & Eisenberg LLP

(57) ABSTRACT

The present invention relates to novel fused heterocyclic or carbocyclic compounds of formula I

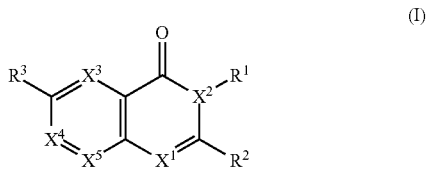

wherein the variables are as defined in the claims and the description. The invention further relates to pharmaceutical compositions comprising these compounds, and to their use for the treatment of vasopressin-related disorders.

29 Claims, No Drawings

(56) References Cited

OTHER PUBLICATIONS

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Budas G., et al., "The Effect of Corticosteroids on Amyloid Beta Precursor Protein/Amyloid Precursor-Like Protein Expression and Processing in Vivo," Neuroscience Letters, 1999, vol. 276 (1), pp. 61-64.
Butte N.F. et al., "Measurement of Milk Intake: Tracer-To-Infant Deuterium Dilution Method," British Journal of Nutrition, 1991, vol. 65, pp. 3-14.
Coward W.A., et al., "New Method for Measuring Milk Intakes in Breast-Fed Babies," Lancet (London, England), 1979, vol. 2 (8132), pp. 13-14.
Czajka D. M., et al., "Effect of Deuterium Oxide on the Reproductive Potential of Mice," Annals of the New York Academy of Sciences, 1960, vol. 84, pp. 770-779.
Czajka D. M. et al., "Physiological Effects of Deuterium on Dogs," American Journal of Physiology, 1961, vol. 201 (2), pp. 357-362.
Decaux G., et al., "Non-Peptide Arginine-Vasopressin Antagonists: The Vaptans," Lancet, 2008, vol. 371 (9624), pp. 1624-1632.
Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.
Fortschritte Der Arzneimittelforschung, Birkhäuser Verlag, Deutschland, Schweiz, 1966, vol. 10, pp. 224-285.
Foster, A. B. et al., "Deuterium Isotope Effects in the Metabolism of Drugs and Xenobiotics: Implications for Drug Design," Advances in Drug Research, 1985, vol. 14, pp. 2-36.
Greene, et al., Protecting Groups in Chemical Synthesis, 3rd Edition, John Wiley & Sons, 1999, Table of Contents.
Kalinin A.V., et al., "Anionic Homologous Fries Rearrangement of O-(2-Methylaryl)Carbamates. A Regiospecific Route to Benzo[B]Furan-2(3H)-Ones Including an Unnamed Metabolite from Helenium Species," Synlett, 1977, vol. 1997 (7), pp. 839-841.
Kato, S. et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Lee B.K. et al., "Apolipoprotein E Genotype, Cortisol, and Cognitive Function in Community-Dwelling Older Adults," The American journal of psychiatry, 2008, vol. 165 (11), pp. 1456-1464.
Lemmens-Gruber R., et al., "Vasopressin Antagonists," Cellular and Molecular Life Sciences, 2006, vol. 63 (15), pp. 1766-1779.
Lizondo, J. et al., "Linezolid: Oxazolidinone antibacterial," Drugs of the Future, 1996, vol. 21 (11), pp. 1116-1123.
Loupy A., Ed., "Microwaves in Organic Synthesis," in: Tetrahedron, 2001, vol. 57, Wiley-VCH 2002, p. 9199 ff. p. 9225 ff.
MacLennan A.H., et al., "Neonatal Body Water Turnover: A Putative Index of Perinatal Morbidity," American Journal of Obstetrics & Gynecology, 1981, vol. 139 (8), pp. 948-952.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Notification of Transmittal of the International Search Report and Written Opinion for Application No. PCT/EP2015/070223, mailed on Oct. 2, 2015, 9 pages.
Obach R.S., "The Prediction of Human Clearance from Hepatic Microsomal Metabolism Data," Current Opinion in Drug Discovery and Development, 2001, vol. 4 (1), pp. 36-44.
Pons G., et al., "Stable Isotopes Labeling of Drugs in Pediatric Clinical Pharmacology," Pediatrics, 1999, vol. 104 (3 Pt 2), pp. 633-639.
Rodewald L.E., et al., "Deuterium Oxide as a Tracer for Measurement of Compliance in Pediatric Clinical Drug Trials," Journal of Pediatrics, 1989, vol. 114 (5), 885-891.
Roozendaal B., et al., "Systems Mediating Acute Glucocorticoid Effects on Memory Consolidation and Retrieval," Progress in Neuro-Psychopharmacology and Biological Psychiatry, 2003, vol. 27 (8), pp. 1213-1223.
Ryckmans T., et al., "Modulation of the Vasopressin System for the Treatment of CNS Diseases," Current opinion in drug discovery & development, 2010, vol. 13 (5), pp. 538-547.
Schwarcz H.P., "Use of Stable Isotopes to Determine Compliance," Controlled Clinical Trials, 1984, vol. 5 (Suppl 4), 573-575.
Surget A., et al., "Involvement of Vasopressin in Affective Disorders," European Journal of Pharmacology, 2008, vol. 583 (2-3), pp. 340-349.
Thibonnier M., "Development and Therapeutic Indications of Orally-active Non-peptide Vasopressin Receptor Antagonists," Expert Opinion on Investigational Drugs, 1998, vol. 7 (5), pp. 729-740.
Thomson J.F. "Physiological Effects of D20 in Mammals," Annals of the New York Academy of Sciences, 1960, vol. 84, pp. 736-744.
Wersinger S.R., et al., "Vasopressin V1b Receptor Knockout Reduces Aggressive Behavior in Male Mice," Molecular Psychiatry, 2002, vol. 7 (9), pp. 975-984.
Zhou Y., et al., "Involvement of Arginine Vasopressin and V1b Receptor in Heroin withdrawal and Heroin Seeking Precipitated by Stress and by Heroin," Neuropsychopharmacology, 2008, vol. 33 (2), pp. 226-236.

* cited by examiner

FUSED HETEROCYCLIC OR CARBOCYCLIC COMPOUNDS CARRYING A SUBSTITUTED CYCLOALIPHATIC RADICAL AND USE THEREOF FOR TREATING VASOPRESSIN-RELATED DISEASES

CROSS-REFERENCE TO RELATED APPLICATION(S)

This claims priority to U.S. Provisional Patent Application No. 62/046,527, filed on Sep. 5, 2014, the entire contents of which are fully incorporated herein by reference.

The present invention relates to novel fused heterocyclic or carbocyclic compounds carrying a substituted cycloaliphatic radical, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3, and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life Sci. 63 (2006), 1766-1779).

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity;

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/mL);

7.) suitable pharmacokinetics (time course of the concentration of the compound of the invention in plasma or in tissue, for example brain). The pharmacokinetics can be described by the following parameters: half-life (in h), volume of distribution (in l·kg−1), plasma clearance (in l·h−1·kg−1), AUC (area under the curve, area under the concentration-time curve, in ng·h·1-1), oral bioavailability (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

Fused heterocyclic or carbocyclic compounds have been described in WO 2006/095014, WO 2008/033764, WO 2008/071779, WO2010/037123, WO 2011/045258 and WO 2012/154760.

It was an object of the present invention to provide compounds for the treatment or prophylaxis of various vasopressin-related diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I

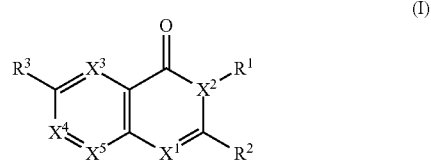

wherein $X^1$, $X^2$, $X^3$, $X^4$ and $X^5$, independently of each other, are N or CH;

$R^1$ is $C_1$-$C_4$-alkyl which carries a group —C(=O)$R^4$ or fluorinated $C_1$-$C_4$-alkyl which carries a group —C(=O)$R^4$;

$R^2$ is phenyl or a 5- or 6-membered heteroaromatic ring with 1, 2 or 3 heteroatoms selected from O, S and N as ring members, where phenyl or the 5- or 6-membered heteroaromatic ring may carry 1, 2 or 3 substituents $R^5$;

$R^3$ is a 3-, 4-, 5- or 6-membered saturated or partially unsaturated carbocyclic ring which carries one substituent $R^6$ and which may additionally carry 1 or 2 substituents $R^7$;

$R^4$ is $OR^8$ or $-NR^9R^{10}$;

each $R^5$ is independently selected from halogen, cyano, nitro, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_3$-$C_8$-cycloalkoxy, fluorinated $C_3$-$C_8$-cycloalkoxy, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)aminocarbonyl, phenyl, phenyl-$C_1$-$C_2$-alkyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$; or two radicals $R^5$, bound on adjacent ring atoms, form together with the ring atoms to which they are bound a saturated or unsaturated 3-, 4-, 5-, 6-, 7-, 8- or 9-membered ring, wherein the ring may contain 1 or 2 heteroatoms or heteroatom groups selected from O, S, N, NO, SO and $SO_2$ and/or 1 or 2 C=O groups as ring members, and wherein the ring may be substituted by one or more radicals $R^{13}$;

$R^6$ is $C_1$-$C_4$-alkyl which carries a radical $-NR^{11}R^{12}$ or fluorinated $C_1$-$C_4$-alkyl, which carries a radical $-NR^{11}R^{12}$;

each $R^7$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy, or two radicals $R^7$ bound on the same carbon ring atom form together a group =O (oxo);

$R^8$ is selected from hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; phenyl, phenyl-$C_1$-$C_2$-alkyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$;

$R^9$ and $R^{10}$, independently of each other, are selected from hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_1$-$C_6$-alkoxy, fluorinated $C_1$-$C_6$-alkoxy, phenyl, phenyl-$C_1$-$C_2$-alkyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$; or $R^9$ and $R^{10}$, together with the nitrogen atom they are bound to, form a 3-, 4-, 5-, 6-, 7- or 8-membered saturated, partially unsaturated or maximally unsaturated heterocyclic ring, where the heterocyclic ring may additionally contain 1 or 2 heteroatoms or heteroatom groups selected from O, S, N, NO, SO, $SO_2$ and C=O as ring members, and where the heterocyclic ring may carry 1, 2, 3 or 4 radicals $R^{13}$;

$R^{11}$ and $R^{12}$, independently of each other, are selected from hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_1$-$C_6$-alkoxy, fluorinated $C_1$-$C_6$-alkoxy, phenyl, phenyl-$C_1$-$C_2$-alkyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$; or $R^{11}$ and $R^{12}$, together with the nitrogen atom they are bound to, form a 3-, 4-, 5-, 6-, 7- or 8-membered saturated, partially unsaturated or maximally unsaturated heterocyclic ring, where the heterocyclic ring may additionally contain 1 or 2 heteroatoms or heteroatom groups selected from O, S, N, NO, SO, $SO_2$ and C=O as ring members, and where the heterocyclic ring may carry 1, 2, 3 or 4 radicals $R^{13}$;

each $R^{13}$ is independently selected from halogen, cyano, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkyl-$C_1$-$C_4$-alkyl, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)-aminocarbonyl, phenyl and phenyl-$C_1$-$C_2$-alkyl; or two radicals $R^{13}$ bound to the same carbon ring atom together a group =O or =S; or two radicals $R^{13}$ bound to the same carbon ring atom may form together with this carbon ring atom a 3-, 4-, 5-, 6-, 7- or 8-membered saturated, partially unsaturated or maximally unsaturated ring (thus forming a spiro ring system), where the ring may contain 1, 2, 3 or 4 heteroatoms or heteroatom-containing groups selected from O, S, N, NO, SO, $SO_2$ and C=O as ring members, and where the ring may be substituted with one or more substituents $R^{14}$; or two non-geminal radicals $R^{13}$ form together a group $-(CH_2)_k-$, where k is 1, 2, 3 or 4, where 1 or 2 hydrogen atoms in this group may be replaced by a methyl group; or two vicinal radicals $R^{13}$ form together a group —CH=CH—CH=CH— (thus forming a phenyl ring fused to the ring to which the two vicinal radicals $R^{13}$ are bound);

each $R^{14}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; and each $R^{15}$ is independently selected from cyano, hydroxyl, nitro, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)-aminocarbonyl, phenyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$; and $R^{15}$ as a substituent on a cycloaliphatic ring is additionally selected from $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl and phenyl-$C_1$-$C_2$-alkyl, where the phenyl moiety in phenyl-$C_1$-$C_2$-alkyl may carry one or more radicals $R^{13}$;

and the N-oxides, stereoisomers and pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhauser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

The term "stereoisomers" encompasses both optical isomers, such as enantiomers or diastereomers, the latter existing due to more than one center of chirality in the molecule, as well as geometrical isomers (cis/trans isomers; correctly speaking, these are also diastereomers).

Depending on the substitution pattern, the compounds of the formula I may have one or more centers of chirality, in which case they are present as mixtures of enantiomers or diastereomers. One stereogenic center is the carbon ring atom via which the carbocyclic radical $R^3$ is bound to the scaffold of the compound I; another is the carbon ring atom of the carbocyclic radical $R^3$ which carries the radical $R^6$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

Halogen in the terms of the present invention is fluorine, chlorine, bromine or iodine, preferably fluorine, chlorine or bromine and especially fluorine or chlorine.

$C_1$-$C_2$-Alkyl is a linear or branched alkyl radical having 1 or 2 carbon atoms, such as methyl and ethyl. $C_1$-$C_3$-Alkyl is a linear or branched alkyl radical having 1 to 3 carbon atoms, such as methyl, ethyl, n-propyl or isopropyl. $C_1$-$C_4$-Alkyl is a linear or branched alkyl radical having 1 to 4 carbon atoms, such as methyl, ethyl, n-propyl, isopropyl, n-butyl, sec-butyl, isobutyl or tert-butyl. $C_1$-$C_6$-Alkyl is a linear or branched alkyl radical having 1 to 6 carbon atoms, such as methyl, ethyl, n-propyl, isopropyl, n-butyl, sec-butyl, isobutyl, tert-butyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dime-thylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

Fluorinated alkyl is a straight-chain or branched alkyl group having from 1 to 4 (=fluorinated $C_1$-$C_4$-alkyl), in particular 1 to 3 carbon atoms (=fluorinated $C_1$-$C_3$-alkyl), more preferably 1 or 2 carbon atoms (=fluorinated $C_1$-$C_2$-alkyl), wherein at least one, e.g. 1, 2, 3, 4 or all of the hydrogen atoms are replaced by fluorine atoms. Examples for fluorinated $C_1$-$C_2$-alkyl are fluoromethyl, difluoromethyl, trifluoromethyl, 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, pentafluoroethyl and the like. Examples for fluorinated $C_1$-$C_3$-alkyl are, apart those mentioned above for fluorinated $C_1$-$C_2$-alkyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-

1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl and the like. Examples for fluorinated $C_1$-$C_4$-alkyl are, apart those mentioned above for fluorinated $C_1$-$C_3$-alkyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position. Examples for $C_2$-$C_3$-alkenyl are ethenyl, 1-propenyl, 2-propenyl or 1-methylethenyl. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl. Examples for $C_2$-$C_6$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "fluorinated alkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by fluorine atoms as mentioned above, for example fluorovinyl, fluoroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position. Examples for $C_2$-$C_3$-alkynyl are ethynyl, 1-propynyl or 2-propynyl. Examples for $C_2$-$C_4$-alkynyl are ethynyl, 1-propynyl, 2-propynyl, 1-butynyl, 2-butynyl, 3-butynyl, 1-methyl-2-propynyl and the like. Examples for $C_2$-$C_6$-alkynyl are ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "fluorinated alkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl") or 2 to 6 ("$C_2$-$C_6$-haloalkynyl") carbon atoms and one or two triple bonds in any position (as mentioned above), where some or all of the hydrogen atoms in these groups are replaced by fluorine atoms as mentioned above.

$C_3$-$C_8$-Cycloalkyl is a monocyclic saturated hydrocarbon radical having 3 to 8, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkyl comprise cyclopropyl and cyclobutyl. Examples of $C_3$-$C_5$-cycloalkyl comprise cyclopropyl, cyclobutyl and cyclopentyl. Examples of $C_3$-$C_6$-cycloalkyl comprise cyclopropyl, cyclobutyl, cyclopentyl and cyclohexyl. Examples of $C_3$-$C_8$-cycloalkyl comprise cyclopropyl, cyclobutyl, cyclopentyl, cyclohexyl, cycloheptyl and cyclooctyl.

Fluorinated $C_3$-$C_8$-cycloalkyl is a monocyclic saturated hydrocarbon radical having 3 to 8, in particular 3 to 6 ("fluorinated $C_3$-$C_6$-cycloalkyl") or 3 to 5 ("fluorinated $C_3$-$C_5$-cycloalkyl") or 3 to 4 ("fluorinated $C_3$-$C_4$-cycloalkyl") carbon ring members (as mentioned above) in which some or all of the hydrogen atoms are replaced by fluorine atoms. Examples for fluorinated $C_3$-$C_4$-cycloalkyl are 1-fluorocyclopropyl, 2-fluorocyclopropyl, 2,2-difluorocyclopropyl, 1-fluorocyclobutyl, 2-fluorocyclobutyl, 3-fluorocyclobutyl, 2,2-difluorocyclobutyl, 3,3-difluorocyclobutyl and the like. Examples for fluorinated $C_3$-$C_5$-cycloalkyl are additionally 1-fluorocyclopentyl, 2-fluorocyclopentyl, 3-fluorocyclopentyl, 2,2-difluorocyclopentyl, 3,3-difluorocyclopentyl, and the like. Examples for fluorinated $C_3$-$C_6$-cycloalkyl are additionally 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, and the like. Examples for fluorinated $C_3$-$C_8$-cycloalkyl are additionally 1-fluorocycloheptyl, 2-fluorocycloheptyl, 3-fluorocycloheptyl, 4-fluorocycloheptyl, 2,2-difluorocycloheptyl, 3,3-difluorocycloheptyl, 4,4-difluorocycloheptyl, 1-fluorocyclooctyl, 2-fluorocyclooctyl, 3-fluorocyclooctyl, 4-fluorocyclooctyl, 2,2-difluorocyclooctyl, 3,3-difluorocyclooctyl, 4,4-difluorocyclooctyl, and the like.

The term "$C_3$-$C_6$-cycloalkyl-$C_1$-$C_4$-alkyl" refers to a $C_3$-$C_6$-cycloalkyl group, as defined above, which is bound to the remainder of the molecule via a $C_1$-$C_4$-alkyl group, as defined above. The term "$C_3$-$C_8$-cycloalkyl-$C_1$-$C_4$-alkyl" refers to a $C_3$-$C_8$-cycloalkyl group, as defined above, which is bound to the remainder of the molecule via a $C_1$-$C_4$-alkyl group, as defined above. Examples for $C_3$-$C_6$-cycloalkyl-$C_1$-$C_4$-alkyl are cyclopropylmethyl, 1-cyclopropyl-1-ethyl, 1-cyclopropyl-2-ethyl, 1-cyclopropyl-1-propyl, 1-cyclopropyl-2-propyl, 2-cyclopropyl-1-propyl, 2-cyclopropyl-2-propyl, 1-cyclopropyl-3-propyl, cyclobutylmethyl, 1-cyclobutyl-1-ethyl, 1-cyclobutyl-2-ethyl, 1-cyclobutyl-1-propyl, 1-cyclobutyl-2-propyl, 2-cyclobutyl-1-propyl, 2-cyclobutyl- 2-propyl, 1-cyclobutyl-3-propyl, cyclopentylmethyl, 1-cyclopentyl-1-ethyl, 1-cyclopentyl-2-ethyl, 1-cyclopentyl-1-propyl, 1-cyclopentyl-2-propyl, 2-cyclopentyl-1-propyl, 2-cyclopentyl-2-propyl, 1-cyclopentyl-3-propyl, cyclohexylmethyl, 1-cyclohexyl-1-ethyl, 1-cyclohexyl-2-ethyl, 1-cyclohexyl-1-propyl, 1-cyclohexyl-2-propyl, 2-cyclohexyl-1-propyl, 2-cyclohexyl-2-propyl and 1-cyclohexyl-3-propyl. Examples for $C_3$-$C_8$-cycloalkyl-$C_1$-$C_4$-alkyl are, apart from those mentioned for $C_3$-$C_6$-cycloalkyl-$C_1$-$C_4$-alkyl, cycloheptylmethyl, 1-cycloheptyl-1-ethyl, 1-cycloheptyl-2-ethyl, 1-cycloheptyl-1-propyl, 1-cycloheptyl-2-propyl, 2-cycloheptyl-1-propyl, 2-cycloheptyl-2-propyl, 1-cycloheptyl-3-propyl, cyclooctylmethyl, 1-cyclooctyl-1-ethyl, 1-cyclooctyl-2-ethyl, 1-cyclooctyl-1-propyl, 1-cyclooctyl-2-propyl, 2-cyclooctyl-1-propyl, 2-cyclooctyl-2-propyl and 1-cyclooctyl-3-propyl.

$C_3$-$C_8$-Cycloalkenyl is a monocyclic partially unsaturated hydrocarbon radical having 3 to 8 ("$C_3$-$C_8$-cycloalkenyl"), in particular 3 to 6 ("$C_3$-$C_6$-cycloalkenyl") or 3 to 5 ("$C_3$-$C_5$-cycloalkenyl") or 3 to 4 ("$C_3$-$C_4$-cycloalkenyl") carbon atoms which is neither aromatic nor antiaromatic or homoaromatic. Examples for $C_3$-$C_4$-cycloalkenyl are cycloprop-1-en-1-yl, cycloprop-1-en-3-yl, cyclobut-1-en-1-yl and cyclobut-1-en-3-yl. Examples for $C_3$-$C_5$-cycloalkenyl are, apart those mentioned for $C_3$-$C_4$-cycloalkenyl, cyclopent-1-en-1-yl, cyclopent-1-en-3-yl and cyclopent-1-en-4-yl. Examples for $C_3$-$C_6$-cycloalkenyl are, apart those mentioned for $C_3$-$C_5$-cycloalkenyl, cyclohex-1-en-1-yl, cyclohex-1-en-3-yl, cyclohex-1-en-4-yl, cyclohexa-1,3-dien-1-yl, cyclohexa-1,3-dien-2-yl, cyclohexa-1,3-dien-5-yl, cyclohexa-1,4-dien-1-yl and cyclohexa-1,4-dien-3-yl. Examples for $C_3$-$C_8$-cycloalkenyl are, apart those mentioned for $C_3$-$C_6$-cycloalkenyl, cyclohept-1-en-1-yl, cyclohept-1-en-3-yl, cyclohept-1-en-4-yl, cyclohept-1-en-5-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl, cyclohepta-1,4-dien-6-yl, cyclooct-1-en-1-yl, cyclooct-1-en-3-yl, cyclooct-1-en-4-yl, cyclooct-1-en-5-yl, cyclocta-1,3-dien-1-yl, cyclocta-1,3-dien-2-yl, cyclocta-1,3-dien-5-yl, cyclocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,5-dien-1-yl and cycloocta-1,5-dien-3-yl.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy. $C_1$-$C_6$-Alkoxy is a linear or branched alkyl radical linked via an oxygen atom and having 1 to 6 carbon atoms. Examples are, apart those mentioned for $C_1$-$C_4$-alkoxy, pentyloxy and hexyloxy.

Fluorinated $C_1$-$C_6$-alkoxy is a straight-chain or branched alkoxy group having from 1 to 6, preferably 1 to 4 carbon atoms (=fluorinated $C_1$-$C_4$-alkoxy), in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.

$C_1$-$C_6$-Alkylthio is a $C_1$-$C_6$-alkyl group, as defined above, attached via a sulfur atom. Examples are methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

Fluorinated $C_1$-$C_6$-alkylthio is a fluorinated $C_1$-$C_4$-alkyl group, as defined above, attached via a sulfur atom. Examples are $SCH_2F$, $SCHF_2$, $SCF_3$, 2-fluoroethylthio, 2,2-difluoroethylthio, 2,2,2-trifluoroethylthio, $SC_2F_5$, 2-fluoropropylthio, 3-fluoropropylthio, 2,2-difluoropropylthio, 2,3-difluoropropylthio, 3,3,3-trifluoropropylthio, $SCH_2$—$C_2F_5$, $SCF_2$—$C_2F_5$, 1-($CH_2F$)-2-fluoroethylthio, 4-fluorobutylthio, 4-chlorobutylthio, 4-bromobutylthio or nonafluorobutylthio.

$C_1$-$C_6$-Alkylsulfinyl is a $C_1$-$C_6$-alkyl group, as defined above, attached via a sulfinyl [S(O)] group. Examples are methylsulfinyl, ethylsulfinyl, n-propylsulfinyl, 1-methylethylsulfinyl (isopropylsulfinyl), butylsulfinyl, 1-methylpropylsulfinyl (secbutylsulfinyl), 2-methylpropylsulfinyl (isobutylsulfinyl) or 1,1-dimethylethylsulfinyl (tert-butylsulfinyl).

Fluorinated $C_1$-$C_6$-alkylsulfinyl is a fluorinated $C_1$-$C_6$-alkyl group, as defined above, attached via a sulfinyl [S(O)] group. Examples are $S(O)CH_2F$, $S(O)CHF_2$, $S(O)CF_3$, 2-fluoroethylsulfinyl, 2,2-difluoroethylsulfinyl, 2,2,2-trifluoroethylsulfinyl, $S(O)C_2F_5$, 2-fluoropropylsulfinyl, 3-fluoropropylsulfinyl, 2,2-difluoropropylsulfinyl, 2,3-difluoropropylsulfinyl, 3,3,3-trifluoropropylsulfinyl, $S(O)CH_2$—$C_2F_5$, $S(O)CF_2$—$C_2F_5$, 1-($CH_2F$)-2-fluoroethylsulfinyl, 4-fluorobutylsulfinyl, or nonafluorobutylsulfinyl.

$C_1$-$C_6$-Alkylsulfonyl is a $C_1$-$C_6$-alkyl group, as defined above, attached via a sulfonyl [S(O)$_2$] group. Examples are methylsulfonyl, ethylsulfonyl, n-propylsulfonyl, 1-methylethylsulfonyl (isopropylsulfonyl), butylsulfonyl, 1-methylpropylsulfonyl (secbutylsulfonyl), 2-methylpropylsulfonyl (isobutylsulfonyl) or 1,1-dimethylethylsulfonyl (tert-butylsulfonyl).

Fluorinated $C_1$-$C_6$-alkylsulfonyl is a fluorinated $C_1$-$C_6$-alkyl group, as defined above, attached via a sulfonyl [S(O)$_2$] group. Examples are $S(O)_2CH_2F$, $S(O)_2CHF_2$, $S(O)_2CF_3$, 2-fluoroethylsulfonyl, 2,2-difluoroethylsulfonyl, 2,2,2-trifluoroethylsulfonyl, $S(O)_2C_2F_5$, 2-fluoropropylsulfonyl, 3-fluoropropylsulfonyl, 2,2-difluoropropylsulfonyl, 2,3-difluoropropylsulfonyl, 3,3,3-trifluoropropylsulfonyl, $S(O)_2CH_2$—$C_2F_5$, $S(O)_2CF_2$—$C_2F_5$, 1-($CH_2F$)-2-fluoroethylsulfonyl, 4-fluorobutylsulfonyl, or nonafluorobutylsulfonyl.

$C_3$-$C_8$-Cycloalkoxy is a $C_3$-$C_8$-cycloalkyl group, as defined above, linked via an oxygen atom. Examples are cyclopropoxy, cyclobutoxy, cyclopentoxy, cyclohexoxy, cycloheptoxy and cyclooctoxy.

Fluorinated $C_3$-$C_8$-cycloalkoxy is a fluorinated $C_3$-$C_8$-cycloalkyl group, as defined above, linked via an oxygen atom. Examples are 1-fluorocyclopropoxy, 2-fluorocyclopropoxy, 2,2-difluorocyclopropoxy, 1-fluorocyclobutoxy, 2-fluorocyclobutoxy, 3-fluorocyclobutoxy, 2,2-difluorocyclobutoxy, 3,3-difluorocyclobutoxy, 1-fluorocyclopentoxy, 2-fluorocyclopentoxy, 3-fluorocyclopentoxy, 2,2-difluorocyclopentoxy, 3,3-difluorocyclopentoxy, 1-fluorocyclohexoxy, 2-fluorocyclohexoxy, 3-fluorocyclohexoxy, 4-fluorocyclohexoxy, 2,2-difluorocyclohexoxy, 3,3-difluorocyclohexoxy, 4,4-difluorocyclohexoxy, 1-fluorocycloheptoxy, 2-fluorocycloheptoxy, 3-fluorocycloheptoxy, 4-fluorocycloheptoxy, 2,2-difluorocycloheptoxy, 3,3-difluorocycloheptoxy, 4,4-difluorocycloheptoxy, 1-fluorocyclooctoxy, 2-fluorocyclooctoxy, 3-fluorocyclooctoxy, 4-fluorocyclooctoxy, 2,2-difluorocyclooctoxy, 3,3-difluorocyclooctoxy, 4,4-difluorocyclooctoxy, and the like.

$C_1$-$C_6$-Alkylcarbonyl is a $C_1$-$C_6$-alkyl group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like.

Fluorinated $C_1$-$C_6$-alkylcarbonyl is a fluorinated $C_1$-$C_6$-alkyl group, as defined above, attached via a carbonyl [C(=O)] group. Examples are trifluoromethylcarbonyl, 2,2,2-trifluoroethylcarbonyl and the like.

Carboxyl is —COOH.

$C_1$-$C_6$-Alkoxycarbonyl is a $C_1$-$C_6$-alkoxy group, as defined above, attached via a carbonyl [C(=O)] group. Examples are methoxycarbonyl, ethoxycarbonyl, propoxycarbonyl, isopropoxycarbonyl, n-butoxycarbonyl and the like.

Fluorinated $C_1$-$C_6$-alkoxycarbonyl is a fluorinated $C_1$-$C_6$-alkoxy group, as defined above, attached via a carbonyl [C(=O)] group. Examples are trifluoromethoxycarbonyl, 2,2,2-trifluoroethoxycarbonyl and the like.

$C_1$-$C_6$-Alkylcarbonyloxy is a $C_1$-$C_6$-alkyl group, as defined above, attached via a carbonyloxy [C(=O)O] group. Examples are acetyloxy (methylcarbonyloxy), propionyloxy (ethylcarbonyloxy), propylcarbonyloxy, isopropylcarbonyloxy, nbutylcarbonyloxy and the like.

Fluorinated $C_1$-$C_6$-alkylcarbonyloxy is a fluorinated $C_1$-$C_6$-alkyl group, as defined above, attached via a carbonyloxy [C(=O)O] group. Examples are trifluoromethylcarbonyloxy, 2,2,2-trifluoroethylcarbonyloxy and the like.

Amino is —NH$_2$.

$C_1$-$C_6$-Alkylamino is a group —NH($C_1$-$C_6$-alkyl). Examples are methylamino, ethylamino, propylamino, isopropylamino, butylamino and the like.

Di-($C_1$-$C_6$-alkyl)amino" is a group —N($C_1$-$C_6$-alkyl)$_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

Aminocarbonyl is a group —C(=O)—NH$_2$.

$C_1$-$C_6$-Alkylaminocarbonyl is a group —C(=O)—N(H)$C_1$-$C_6$-alkyl. Examples are methylaminocarbonyl, ethylaminocarbonyl, propylaminocarbonyl, isopropylaminocarbonyl, butylaminocarbonyl and the like.

Di-($C_1$-$C_6$-alkyl)aminocarbonyl is a group —C(=O)—N($C_1$-$C_6$-alkyl)$_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

Phenyl-$C_1$-$C_2$-alkyl is a phenyl group bound via a $C_1$-$C_2$-alkyl group, as defined above. Examples are benzyl, phenyl-1-ethyl and phenyl-2-ethyl (phenethyl).

Examples for 5- or 6-membered heteroaromatic rings with 1, 2 or 3 heteroatoms selected from O, S and N as ring members are 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, oxadiozole-4-yl, oxadiozole-5-yl, [1,2,4]-oxadiozole-3-yl, [1,2,4]-oxadiozole-5-yl, [1,3,4]-oxadiozole-2-yl, [1,2,5]-oxadiozole-3-yl, thiadiozole-5-yl, [1,2,4]-thiadiozole-3-yl, [1,2,4]-thiadiozole-5-yl, [1,3,4]-thiadiozole-2-yl, [1,2,5]-thiadiozole-3-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl and [1,3,5]-triazin-2-yl.

A 3-, 4-, 5- or 6-membered saturated or partially unsaturated carbocyclic ring is not maximally unsaturated and is thus neither aromatic nor antiaromatic or homoaromatic. It is a $C_3$-$C_6$-cycloalkyl or $C_3$-$C_6$-cycloalkenyl ring, where cycloalkenyl is a monocyclic partially (not maximally) unsaturated carbocyclic ring. Examples are $C_3$-$C_6$-cycloalkyl rings, such as cyclopropyl, cyclobutyl, cyclopentyl and cyclohexyl, and $C_3$-$C_6$-cycloalkenyl rings, such as cycloprop-1-en-1-yl, cycloprop-1-en-3-yl, cyclobut-1-en-1-yl, cyclobut-1-en-3-yl, cyclopent-1-en-1-yl, cyclopent-1-en-3-yl, cyclopent-1-en-4-yl, cyclohex-1-en-1-yl, cyclohex-1-en-3-yl, cyclohex-1-en-4-yl, cyclohexa-1,3-dien-1-yl, cyclohexa-1,3-dien-2-yl, cyclohexa-1,3-dien-5-yl, cyclohexa-1,4-dien-1-yl and cyclohexa-1,4-dien-3-yl.

The term "3-, 4-, 5-, 6-, 7- or 8-membered saturated, partially unsaturated or maximum unsaturated heterocyclic ring containing 1, 2 or 3 heteroatoms or heteroatom groups selected from O, N, S, NO, SO and SO$_2$, as ring members" [wherein "maximum unsaturated" includes also "aromatic"] as used herein denotes monocyclic radicals, the monocyclic radicals being saturated, partially unsaturated or maximum unsaturated (including aromatic). 7-membered rings cannot be aromatic; they are homoaromatic if maximally unsaturated (3 double bonds). Maximally unsaturated 8-membered rings (4 double bonds) are not aromatic, either.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. Partially unsaturated rings contain less C—C and/or C—N and/or N—N double bonds than allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one 0 ring atom, these are not adjacent.

Examples of a 3-, 4-, 5-, 6-, 7- or 8-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl, azocan-1-, 2-, 3- or 4-yl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl, tetrahydro-1,4-dioxepinyl, 1,2,3,4,5,6-hexahydroazocine-1-, 2-, 3-, 4-, 5-, 6-, 7- or 8-yl and the like.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H[1,3]-diazepine and 1H-[1,4]-diazepine; and further azocin-1-, 2-, 3- or 4-yl and the like The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals $X^1$, $X^2$, $X^3$, $X^4$, $X^5$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

In a preferred embodiment, $X^1$ is N.

In a preferred embodiment, $X^2$ is N.

In a preferred embodiment, $X^3$, $X^4$ and $X^5$ are CH.

In particular, $X^1$ and $X^2$ are N and $X^3$, $X^4$ and $X^5$ are CH, so that the scaffold of compounds I is a quinazolin-4-one ring.

In a preferred embodiment, $R^1$ is $C_1$-$C_4$-alkyl which carries a group —C(=O)$R^4$; more preferably $C_1$-$C_2$-alkyl which carries a group —C(=O)$R^4$; and is in particular —$CH_2$—C(=O)$R^4$.

In one preferred embodiment, $R^4$ is $OR^8$, where $R^8$ has one of the above general or, in particular, one of the below preferred meanings. In particular, $R^8$ is selected from hydrogen, $C_1$-$C_4$-alkyl and fluorinated $C_1$-$C_4$-alkyl; and is specifically hydrogen or methyl.

In another more preferred embodiment, $R^4$ is $NR^9R^{10}$, where $R^9$ and $R^{10}$ have one of the above general or, in particular, one of the below preferred meanings.

Preferably, $R^9$ and $R^{10}$, independently of each other, are selected from hydrogen, $C_1$-$C_6$-alkyl, fluorinated $C_1$-$C_6$-alkyl, $C_2$-$C_4$-alkenyl, fluorinated $C_2$-$C_4$-alkenyl, $C_2$-$C_4$-alkynyl, fluorinated $C_2$-$C_4$-alkynyl, $C_3$-$C_8$-cycloalkyl, fluorinated $C_3$-$C_8$-cycloalkyl and $C_3$-$C_8$-cycloalkyl-$C_1$-$C_4$-alkyl. More preferably, $R^9$ is selected from hydrogen and $C_1$-$C_4$-alkyl; and $R^{10}$ is selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl and $C_3$-$C_6$-cycloalkyl-$C_1$-$C_4$-alkyl. In particular, $R^9$ is selected from hydrogen and methyl, and is specifically hydrogen, and $R^{10}$ is selected from hydrogen, $C_1$-$C_6$-alkyl, fluorinated $C_1$-$C_6$-alkyl, $C_3$-$C_6$-cycloalkyl, and $C_3$-$C_6$-cycloalkyl-methyl and specifically from $C_1$-$C_6$-alkyl, fluorinated $C_1$-$C_6$-alkyl, cyclopropyl, and cyclopropyl-methyl.

In a preferred embodiment, $R^2$ is phenyl or a 6-membered heteroaromatic ring selected from pyridyl and pyrimidyl, where phenyl and the 6-membered heteroaromatic ring may carry 1, 2 or 3, in particular 1, substituents $R^5$, where $R^5$ has one of the above general, or, in particular one of the below preferred meanings. More preferably, $R^2$ is phenyl which may carry 1, 2 or 3, in particular 1, substituents $R^5$, and which in particular carries one radical $R^5$, where $R^5$ has one of the above general, or, in particular one of the below preferred meanings.

Preferably, each $R^5$ is independently selected from halogen, cyano, nitro, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$- alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkoxy, fluorinated $C_3$-$C_8$-cycloalkoxy, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl and di-($C_1$-$C_6$-alkyl)-aminocarbonyl. More preferably, each $R^5$ is independently selected from halogen, cyano, nitro, hydroxyl, $C_1$-$C_6$-alkyl, fluorinated $C_1$-$C_6$-alkyl, $C_1$-$C_6$-alkoxy and fluorinated $C_1$-$C_6$-alkoxy; and is in particular halogen.

If $R^2$ is phenyl which carries one radical $R^5$, this $R^5$ is preferably bound in meta-position, relative to the attachment point of $R^2$ to the remainder of the molecule.

Very specifically $R^2$ is 3-chlorophenyl.

The 3-, 4-, 5- or 6-membered saturated or partially unsaturated carbocyclic ring $R^3$ is a $C_3$-$C_6$-cycloalkyl or $C_3$-$C_6$-cycloalkenyl ring. Preferably, the cycloalkenyl ring contains only one C=C double bond. Examples therefor are as cyclopropenyl (e.g. cycloprop-1-en-1-yl, cycloprop-1-en-3-yl), cyclobutenyl (e.g. cyclobut-1-en-1-yl, cyclobut-1-en-3-yl), cyclopentenyl (e.g. cyclopent-1-en-1-yl, cyclopent-1-en-3-yl, cyclopent-1-en-4-yl), and cyclohexenyl (e.g. cyclohex-1-en-1-yl, cyclohex-1-en-3-yl, cyclohex-1-en-4-yl). Preferably, the 3-, 4-, 5- or 6-membered saturated or partially unsaturated carbocyclic ring $R^3$ carries one substituent $R^6$ and no substituents $R^2$.

More preferably, $R^3$ is $C_3$-$C_4$-cycloalkyl or $C_3$-$C_4$-cycloalkenyl, where $C_3$-$C_4$-cycloalkyl or $C_3$-$C_4$-cycloalkenyl carries one substituent $R^6$ (and no substituents $R^2$). In particular, $R^3$ is $C_3$-$C_4$-cycloalkyl or cyclobutenyl (cyclobut-1-en-1-yl or cyclobut-1-en-3-yl), where $C_3$-$C_4$-cycloalkyl or cyclobutenyl carries one substituent $R^6$ (and no substituents $R^2$). In the $C_3$-$C_4$-cycloalkyl or $C_3$-$C_4$-cycloalkenyl ring, $R^6$ is preferably bound in 3-position, relative to the 1-position of the attachment point of $R^3$ to the remainder of the molecule (indeed, correctly speaking, in the $C_3$-cycloalkyl (=cyclopropyl) or $C_3$-cycloalkenyl (=cyclopropenyl) ring $R^6$ is preferably bound in 2-position).

$R^6$ is preferably $C_1$-$C_4$-alkyl which carries a radical —$NR^{11}R^{12}$, more preferably $C_1$-$C_2$-alkyl which carries a radical —$NR^{11}R^{12}$, and in particular —$CH_2$—$NR^{11}R^{12}$ or —$CH_2CH_2$—$NR^{11}R^{12}$, where $R^{11}$ and $R^{12}$ have one of the above general or, in particular, one of the below preferred meanings.

Preferably, $R^{11}$ and $R^{12}$, independently of each other, are selected from hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, phenyl, phenyl-$C_1$-$C_2$-alkyl and a 3-, 4-, 5-, 6-, 7- or 8-membered saturated, partially unsaturated or maximally unsaturated heterocyclic ring containing 1, 2 or 3 heteroatoms or heteroatom groups selected from O, S, N, NO, SO and $SO_2$ as ring members, where phenyl, phenyl-$C_1$-$C_2$-alkyl and the heterocyclic ring may carry one or more radicals $R^{13}$; or $R^{11}$ and $R^{12}$, together with the nitrogen atom they are bound to, form a 3-, 4-, 5-, 6-, 7- or 8-membered saturated or partially unsaturated heterocyclic ring, where the heterocyclic ring may additionally contain 1 or 2 heteroatoms or heteroatom groups selected from O, S, N, NO, SO and $SO_2$ as ring members, and where the heterocyclic ring may carry 1, 2, 3 or 4 radicals $R^{13}$; where $R^{13}$ has one of the above general or, in particular, one of the below preferred meanings.

More preferably, $R^{11}$ and $R^{12}$, independently of each other, are selected from hydrogen, $C_1$-$C_6$-alkyl and fluorinated $C_1$-$C_6$-alkyl; or $R^{11}$ and $R^{12}$, together with the nitrogen atom they are bound to, form a 3-, 4-, 5-, 6-, 7- or 8-membered saturated or partially unsaturated heterocyclic ring, where the heterocyclic ring may additionally contain 1 or 2 heteroatoms or heteroatom groups selected from O, S, N, NO, SO and $SO_2$ as ring members, and where the heterocyclic ring may carry 1, 2, 3 or 4 radicals $R^{13}$; where $R^{13}$ has one of the above general or, in particular, one of the below preferred meanings.

Even more preferably, $R^{11}$ and $R^{12}$, independently of each other, are selected from hydrogen and $C_1$-$C_6$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom or heteroatom group selected from O, S, N, NO, SO and $SO_2$ as ring member, and where the heterocyclic ring may carry 1, 2, 3 or 4 radicals $R^{13}$; where $R^{13}$ has one of the above general or, in particular, one of the below preferred meanings.

In particular, the 4-, 5-, 6- or 7-membered saturated or partially unsaturated heterocyclic ring N-bound ring formed by $R^{11}$ and $R^{12}$ together with the nitrogen atom they are bound to is selected from azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl, 1,2-diazepan-1-yl, 1,3-diazepan-1-yl, 1,4-diazepan-1-yl, 1,2-oxazepan-4-yl, 1,3-oxazepan-4-yl, 1,4-oxazepan-4-yl, 1,2,3,4-tetrahydropyridin-1-yl, 1,2,3,6-tetrahydropyridin-1-yl and 1,4-dihydropyridin-1-yl; and especially from azetidin-1-yl, pyrrolidin-1-yl, piperidin-1-yl, morpholin-4-yl, thiomorpholin-4-yl, azepan-1-yl, 1,4-oxazepan-4-yl and 1,2,3,6-tetrahydropyridin-1-yl. The heterocyclic ring may carry 1, 2, 3 or 4 radicals $R^{13}$; where $R^{13}$ has one of the above general or, in particular, one of the below preferred meanings.

Specifically, $R^{11}$ and $R^{12}$, independently of each other, are $C_1$-$C_4$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom selected from O and S as ring member, and where the heterocyclic ring may carry 1, 2, 3 or 4 radicals $R^{13}$.

In particular, such 4-, 5-, 6- or 7-membered saturated or partially unsaturated heterocyclic ring N-bound rings formed by $R^{11}$ and $R^{12}$ together with the nitrogen atom they are bound to and optionally additionally containing one heteroatom or heteroatom group selected from O and S as ring member are selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, azepan-1-yl, 1,2-oxazepan-4-yl, 1,3-oxazepan-4-yl, 1,4-oxazepan-4-yl, 1,2,3,4-tetrahydropyridin-1-yl, 1,2,3,6-tetrahydropyridin-1-yl and 1,4-dihydropyridin-1-yl; and especially from azetidin-1-yl, pyrrolidin-1-yl, piperidin-1-yl, morpholin-4-yl, thiomorpholin-4-yl, azepan-1-yl, 1,4-oxazepan-4-yl and 1,2,3,6-tetrahydropyridin-1-yl. The heterocyclic ring may carry 1, 2, 3 or 4 radicals $R^{13}$; where $R^{13}$ has one of the above general or, in particular, one of the below preferred meanings.

Preferably, each $R^{13}$ is independently selected from halogen, cyano, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkyl-$C_1$-$C_4$-alkyl, $C_1$-$C_6$-alkoxy and fluorinated $C_1$-$C_6$-alkoxy; or two radicals $R^{13}$ bound to the same carbon ring atom together a group =O or =S;

or two radicals $R^{13}$ bound to the same carbon ring atom (i.e. two geminally bound radicals $R^{13}$) may form together with this carbon ring atom a 3-, 4-, 5- or 6-membered saturated ring (thus forming a spiro system), where the ring may contain 1 or 2 heteroatoms or heteroatom-containing groups selected from O, S, N, NO, SO and $SO_2$ as ring members;

or two non-geminal radicals $R^{13}$ form together a group —$(CH_2)_k$—, where k is 1, 2, 3 or 4. Preferably, the two non-geminal radicals $R^{13}$ are non-vicinal, too.

More preferably, each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 3-, 4-, 5- or 6-membered saturated ring, where the ring may contain 1 or 2 heteroatoms or heteroatom-containing groups selected from O, S, N, NO, SO and $SO_2$ as ring members; or two non-geminal radicals $R^{13}$ form together a group —$(CH_2)_k$—, where k is 1, 2, 3 or 4, and where preferably the two non-geminal radicals $R^{13}$ are non-vicinal, too.

In particular, each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 4- or 6-membered saturated ring, where the ring may contain 1 heteroatom or heteroatom-containing group selected from O, S, N, NO, SO and $SO_2$ as ring member; or two non-geminal radicals $R^{13}$ form together a group —$(CH_2)_k$—, where k is 1 or 2, and where preferably the two non-geminal radicals $R^{13}$ are non-vicinal, too.

Specifically, each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 4- or 6-membered saturated heterocyclic ring, where the heterocyclic ring contains 1 oxygen atom as ring member; or two non-geminal radicals $R^{13}$ form together a group —$(CH_2)_k$—, where k is 1 or 2, and where preferably the two non-geminal radicals $R^{13}$ are non-vicinal, too.

Examples for N-bound rings formed by $R^{11}$ and $R^{12}$ together with the nitrogen atom they are bound two wherein two radicals $R^{13}$ bound to the same carbon ring atom may form together with this carbon ring atom a 3-, 4-, 5- or 6-membered saturated ring, where the ring may contain 1 or 2 heteroatoms or heteroatom-containing groups selected from O, S, N, NO, SO and $SO_2$ as ring members, are 2-aza-spiro[3.3]heptan-2-yl, 2,6-diaza-spiro[3.3]heptan-2-yl, 2-oxa-6-aza-spiro[3.3]heptan-6-yl, 2-thia-6-aza-spiro[3.3]heptan-6-yl, 2-oxo-2-thia-6-aza-spiro[3.3]heptan-6-yl, 2,2-dioxo-2-thia-6-aza-spiro[3.3]heptan-6-yl, 2-aza-spiro[3.5]nonan-2-yl, 2,7-diaza-spiro[3.5]nonan-2-yl, 7-oxa-2-aza-spiro[3.5]nonan-2-yl, 7-thia-2-aza-spiro[3.5]nonan-2-yl, 7-oxo-7-thia-2-aza-spiro[3.5]nonan-2-yl, 7,7-dioxo-7-thia-2-aza-spiro[3.5]nonan-2-yl, 3-aza-spiro[5.5]undecan-3-yl, 3,9-diaza-spiro[5.5]undecan-3-yl, 3-oxa-9-aza-spiro[5.5]undecan-3-yl, 3-thia-9-aza-spiro[5.5]undecan-3-yl and 3,3-di-oxo-3-thia-9-aza-spiro[5.5]undecan-3-yl. Among these, preference is given to 2-aza-spiro[3.3]heptan-2-yl, 2,6-diaza-spiro[3.3]heptan-2-yl, 2-oxa-6-aza-spiro[3.3]heptan-6-yl, 2-aza-spiro[3.5]nonan-2-yl, 2,7-diaza-spiro[3.5]nonan-2-yl and 7-oxa-2-aza-spiro[3.5]nonan-2-yl. The N-bound rings formed by $R^{11}$ and $R^{12}$ together with the nitrogen atom may carry further radicals $R^{13}$. These further radicals $R^{13}$ are preferably selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy.

Examples for N-bound rings formed by $R^{11}$ and $R^{12}$ together with the nitrogen atom they are bound two wherein two non-geminal (and non-vivinal) radicals $R^{13}$ form together a group —$(CH_2)_k$—, where k is 1, 2, 3 or 4, are 6-azabicyclo[3.1.1.]heptan-6-yl, 3,6-diazabicyclo[3.1.1.]heptan-6-yl, 3-oxa-6-azabicyclo[3.1.1]heptan-6-yl, 8-azabicyclo[3.2.1]octan-8-yl, 3,8-diazabicyclo[3.2.1]octan-8-yl, 3-oxa-8-azabicyclo[3.2.1]octan-8-yl, 3-azabicyclo[2.2.1.]heptan-3-yl, 2,5-diazabicyclo[2.2.1.]heptan-2-yl, 2-oxa-5-azabicyclo[2.2.1]heptan-5-yl, 3-azabicyclo[2.2.2]octan-3-yl, 2,5-diazabicyclo[2.2.2]octan-2-yl, 2-oxa-5-azabicyclo[2.2.2]octan-5-yl, and the like. Among these, preference is given to 6-azabicyclo[3.1.1.]heptan-6-yl, 8-azabicyclo[3.2.1]octan-8-yl, 3-azabicyclo[2.2.1.]heptan-3-yl and 3-azabicyclo[2.2.2]octan-3-yl. These rings may carry further radicals $R^{13}$. These further radicals $R^{13}$ are preferably selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy.

Preferably, each $R^{14}$ is independently selected from F, Cl, cyano, hydroxyl, methyl, $CHF_2$, $CF_3$, methoxy, $OCHF_2$ and $OCF_3$.

Preferably, each $R^{15}$ is independently selected from cyano, hydroxyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl and phenyl; and $R^{15}$ as a substituent on a cycloaliphatic ring is additionally selected from $C_1$-$C_6$-alkyl and fluorinated $C_1$-$C_6$-alkyl. More preferably, each $R^{15}$ is independently selected from cyano, hydroxyl, $C_3$-$C_6$-cycloalkyl, fluorinated $C_3$-$C_6$-cycloalkyl, $C_1$-$C_6$-alkoxy, fluorinated $C_1$-$C_6$-alkoxy and phenyl; and $R^{15}$ as a substituent on a cycloaliphatic ring is additionally selected from $C_1$-$C_6$-alkyl and fluorinated $C_1$-$C_6$-alkyl.

In a specific embodiment, the compound of formula I is a compound of formula IA

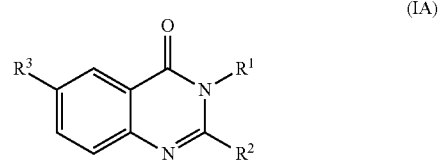

(IA)

wherein $R^1$, $R^2$ and $R^3$ have one of the above general or, in particular, one of the above preferred definitions. In particular, $R^1$ is —$CH_2$—$C(=O)R^4$, wherein $R^4$ has one of the above general or, in particular, one of the above preferred definitions; and $R^2$ is phenyl which carries 1 radical $R^5$ in meta-position, wherein $R^5$ has one of the above general or, in particular, one of the above preferred definitions and is specifically Cl.

The invention preferably relates to compounds of the formula IA in which
- $R^1$ is $C_1$-$C_2$-alkyl which carries a group —C(=O)$R^4$;
- $R^2$ is phenyl which carries one substituent $R^5$;
- $R^3$ is $C_3$-$C_4$-cycloalkyl or $C_3$-$C_4$-cycloalkenyl, where $C_3$-$C_4$-cycloalkyl or $C_3$-$C_4$-cycloalkenyl carries one substituent $R^6$;
- $R^4$ is $OR^8$ or $NR^9R^{10}$;
- $R^5$ is selected from halogen, cyano, nitro, hydroxyl, $C_1$-$C_6$-alkyl, fluorinated $C_1$-$C_6$-alkyl, $C_1$-$C_6$-alkoxy and fluorinated $C_1$-$C_6$-alkoxy;
- $R^6$ is $C_1$-$C_4$-alkyl which carries a radical —$NR^{11}R^{12}$;
- $R^8$ is hydrogen, $C_1$-$C_4$-alkyl or fluorinated $C_1$-$C_4$-alkyl;
- $R^9$ and $R^{10}$, independently of each other, are selected from hydrogen, $C_1$-$C_6$-alkyl, fluorinated $C_1$-$C_6$-alkyl, $C_2$-$C_4$-alkenyl, fluorinated $C_2$-$C_4$-alkenyl, $C_2$-$C_4$-alkynyl, fluorinated $C_2$-$C_4$-alkynyl, $C_3$-$C_8$-cycloalkyl, fluorinated $C_3$-$C_8$-cycloalkyl and $C_3$-$C_8$-cycloalkyl-$C_1$-$C_4$-alkyl;
- $R^{11}$ and $R^{12}$, independently of each other, are selected from hydrogen, $C_1$-$C_6$-alkyl and fluorinated $C_1$-$C_6$-alkyl; or $R^{11}$ and $R^{12}$, together with the nitrogen atom they are bound to, form a 3-, 4-, 5-, 6-, 7- or 8-membered saturated or partially unsaturated heterocyclic ring, where the heterocyclic ring may additionally contain 1 or 2 heteroatoms or heteroatom groups selected from O, S, N, NO, SO and $SO_2$ as ring members, and where the heterocyclic ring may carry 1, 2, 3 or 4 radicals $R^{13}$; and
- each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 3-, 4-, 5- or 6-membered saturated ring, where the ring may contain 1 or 2 heteroatoms or heteroatom-containing groups selected from O, S, N, NO, SO and $SO_2$ as ring members; or two non-geminal radicals $R^{13}$ form together a group —$(CH_2)_k$—, where k is 1, 2, 3 or 4.

The invention more preferably relates to compounds of the formula IA in which
- $R^1$ is —$CH_2$—C(=O)$R^4$;
- $R^2$ is phenyl which carries substituent $R^5$ bound in meta-position;
- $R^3$ is $C_3$-$C_4$-cycloalkyl or cyclobutenyl, where $C_3$-$C_4$-cycloalkyl or cyclobutenyl carries one substituent $R^6$;
- $R^4$ is $OR^8$ or $NR^9R^{10}$;
- $R^5$ is selected from halogen, cyano, nitro, hydroxyl, $C_1$-$C_6$-alkyl, fluorinated $C_1$-$C_6$-alkyl, $C_1$-$C_6$-alkoxy and fluorinated $C_1$-$C_6$-alkoxy, and in particular from halogen;
- $R^6$ is $C_1$-$C_2$-alkyl which carries a radical —$NR^{11}R^{12}$;
- $R^8$ is hydrogen or $C_1$-$C_4$-alkyl;
- $R^9$ is selected from hydrogen and $C_1$-$C_4$-alkyl;
- $R^{10}$ is selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl and $C_3$-$C_6$-cycloalkyl-$C_1$-$C_4$-alkyl;
- $R^{11}$ and $R^{12}$, independently of each other, are selected from hydrogen and $C_1$-$C_6$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom or heteroatom group selected from O, S, N, NO, SO and $SO_2$ as ring member, and where the heterocyclic ring may carry 1, 2, 3 or 4 radicals $R^{13}$; and
- each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 3-, 4-, 5- or 6-membered saturated ring, where the ring may contain 1 or 2 heteroatoms or heteroatom-containing groups selected from O, S, N, NO, SO and $SO_2$ as ring members; or two non-geminal radicals $R^{13}$ form together a group —$(CH_2)_k$—, where k is 1, 2, 3 or 4, and where preferably the two non-geminal radicals $R^{13}$ are non-vicinal, too.

In particular, the invention relates to compounds of the formula IA in which
- $R^1$ is —$CH_2$—C(=O)$R^4$;
- $R^2$ is 3-chlorophenyl;
- $R^3$ is $C_3$-$C_4$-cycloalkyl or cyclobut-1-en-1-yl, where $C_3$-$C_4$-cycloalkyl or cyclobut-1-en-1-yl carries one substituent $R^6$, where $R^6$ is preferably bound in 3-position, relative to the 1-position of the attachment point of $R^3$ to the remainder of the molecule;
- $R^4$ is $OR^8$ or $NR^9R^{10}$;
- $R^6$ is —$CH_2$—$NR^{11}R^{12}$ or —$CH_2CH_2$—$NR^{11}R^{12}$;
- $R^8$ is hydrogen or methyl;
- $R^9$ is selected from hydrogen and methyl, and is specifically hydrogen;
- $R^{10}$ is selected from hydrogen, $C_1$-$C_6$-alkyl, fluorinated $C_1$-$C_6$-alkyl, $C_3$-$C_6$-cycloalkyl, and $C_3$-$C_6$-cycloalkyl-methyl;
- $R^{11}$ and $R^{12}$, independently of each other, are selected from hydrogen and $C_1$-$C_6$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom or heteroatom group selected from O, S, N, NO, SO and $SO_2$ as ring member, and where the heterocyclic ring may carry 1, 2, 3 or 4 radicals $R^{13}$; and
- each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 4- or 6-membered saturated ring, where the ring may contain 1 heteroatom or heteroatom-containing group selected from O, S, N, NO, SO and $SO_2$ as ring member; or two non-geminal radicals $R^{13}$ form together a group —$(CH_2)_k$—, where k is 1 or 2, and where preferably the two non-geminal radicals $R^{13}$ are non-vicinal, too.

Specifically, the invention relates to compounds of the formula IA in which
- $R^1$ is —$CH_2$—C(=O)$R^4$;
- $R^2$ is 3-chlorophenyl;
- $R^3$ is $C_3$-$C_4$-cycloalkyl or cyclobut-1-en-1-yl, where $C_3$-$C_4$-cycloalkyl or cyclobut-1-en-1-yl carries one substituent $R^6$, where $R^6$ is preferably bound in 3-position, relative to the 1-position of the attachment point of $R^3$ to the remainder of the molecule;
- $R^4$ is $NR^9R^{10}$;
- $R^6$ is —$CH_2$—$NR^{11}R^{12}$ or —$CH_2CH_2$—$NR^{11}R^{12}$;
- $R^9$ is hydrogen;
- $R^{10}$ is selected from $C_1$-$C_6$-alkyl, fluorinated $C_1$-$C_6$-alkyl, cyclopropyl, and cyclopropyl-methyl;
- $R^{11}$ and $R^{12}$, independently of each other, are $C_1$-$C_4$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom or heteroatom group selected from O and S as ring member, and where the heterocyclic ring may carry 1, 2, 3 or 4 radicals $R^{13}$; and each $R^{13}$ is independently selected from halogen, cyano, hydroxyl, $C_1$-$C_4$-alkyl, fluorinated $C_1$-$C_4$-alkyl, $C_1$-$C_4$-alkoxy and fluorinated $C_1$-$C_4$-alkoxy; or two radicals $R^{13}$ bound to the same carbon ring atom may form together with this carbon ring atom a 4- or 6-membered saturated heterocyclic ring, where the heterocyclic ring contains 1 oxygen atom as ring member; or two non-geminal radicals $R^{13}$ form together a group —$(CH_2)_k$—, where k is 1 or 2, and where preferably the two non-geminal radicals $R^{13}$ are non-vicinal, too.

Examples of preferred embodiments of the present invention are compounds of the formulae I.1 to I.50 and the N-oxides, stereoisomers and the pharmaceutically acceptable salts thereof, in which $R^{5a}$, $R^{5b}$ and $R^{5c}$ are hydrogen or have one of the above general or preferred meanings of $R^5$, Q is —$NR^{11}R^{12}$, where $R^{11}$ and $R^{12}$ have one of the above general or preferred meanings, and Y is CH or N. In particular, preferred compounds are the individual compounds compiled in the tables 1 to 4100 below. Moreover, the meanings mentioned below for the individual variables in the tables are per se, independently of the combination in which they are mentioned, a particularly preferred embodiment of the substituents in question.

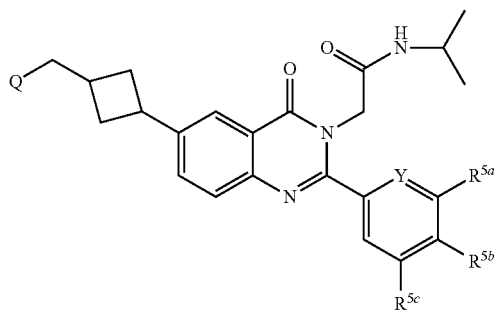

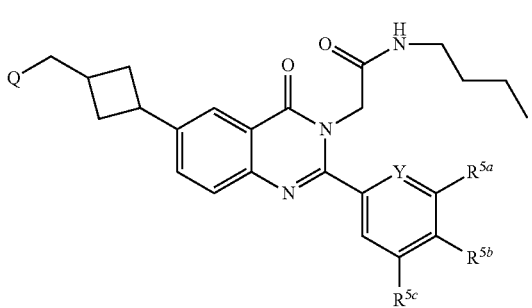

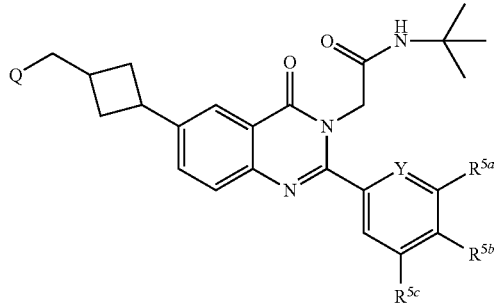

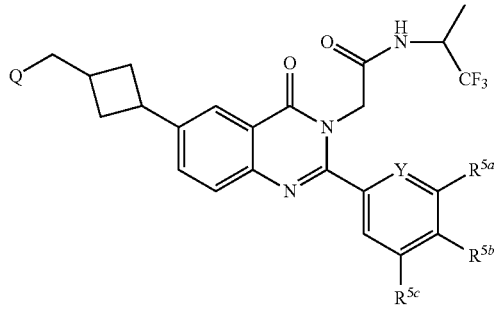

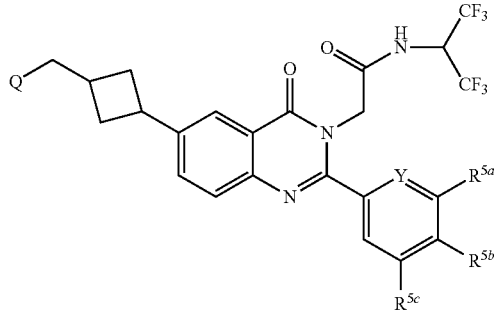

-continued

I.9
I.10
I.11
I.12
I.13
I.14
I.15
I.16
I.17
I.18

-continued
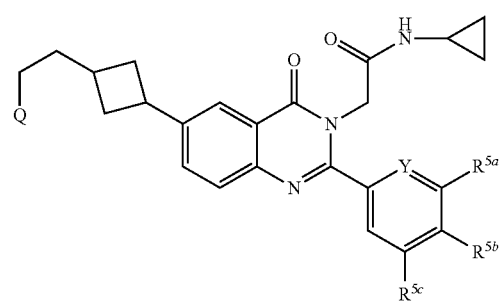 I.19
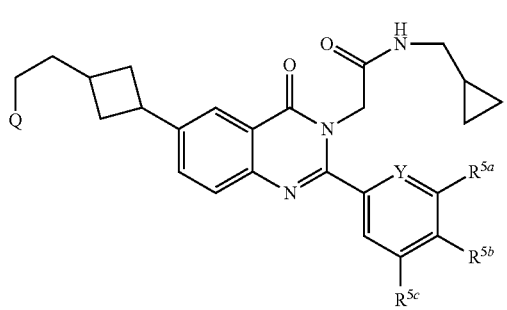 I.20
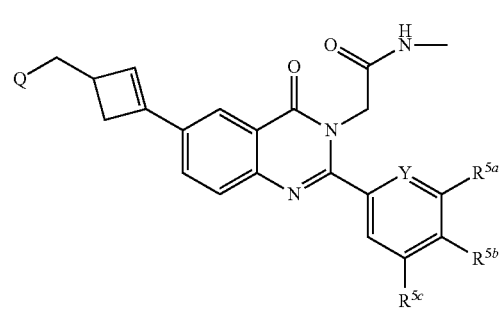 I.21
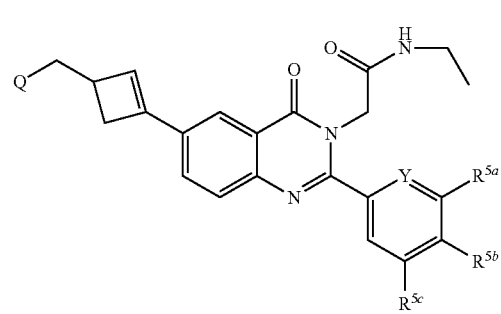 I.22
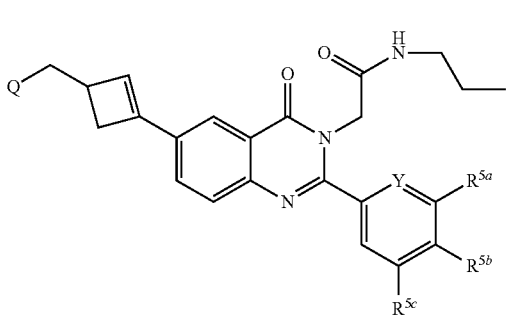 I.23
-continued
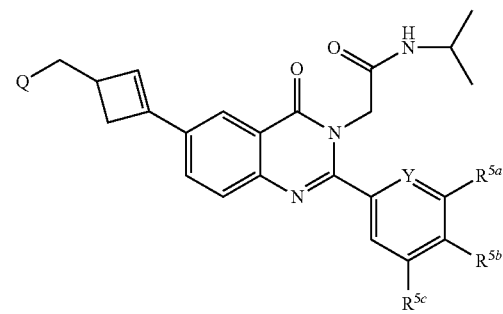 I.24
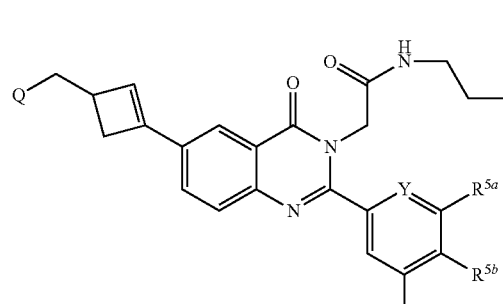 I.25
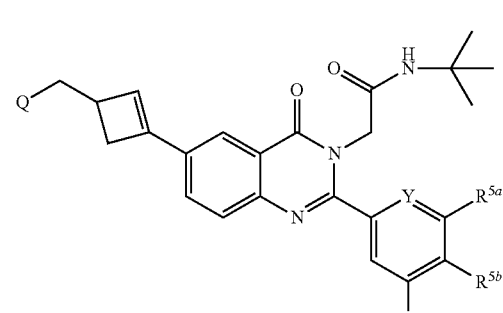 I.26
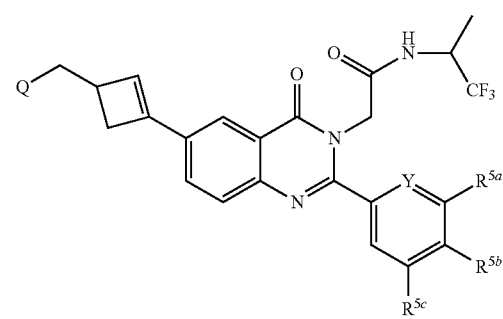 I.27
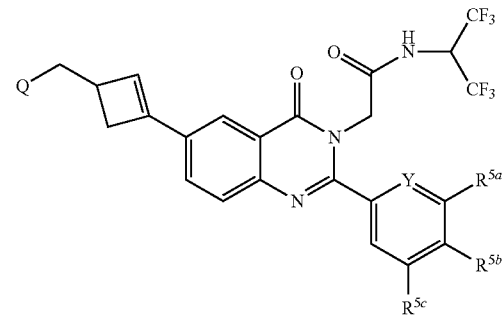 I.28

I.29
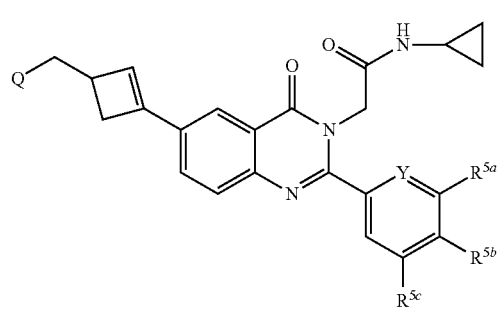
I.30
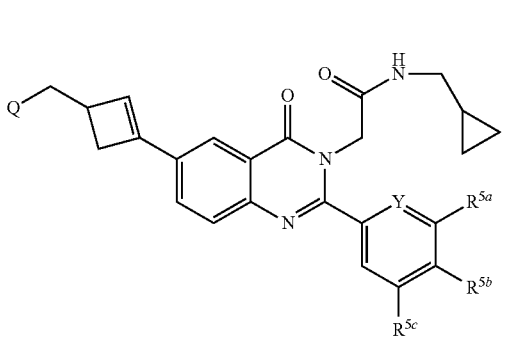
I.31
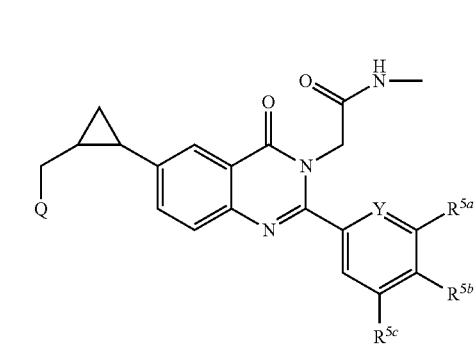
I.32
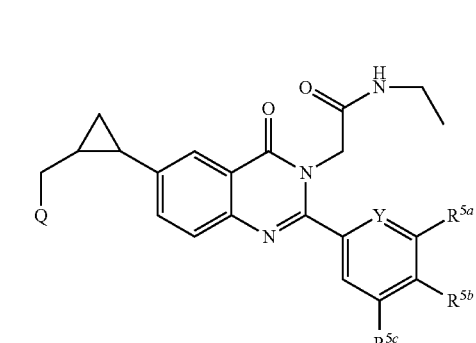
I.33
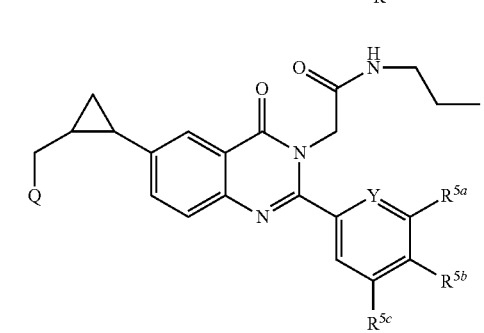
I.34
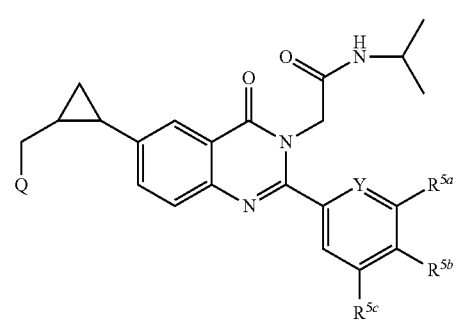
I.35
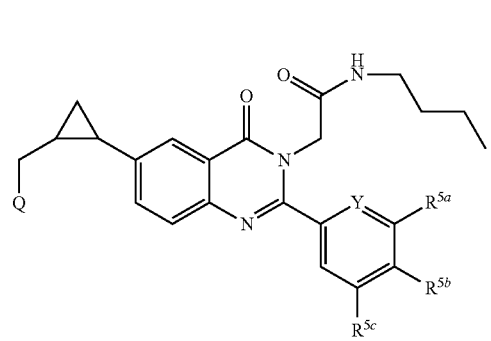
I.36
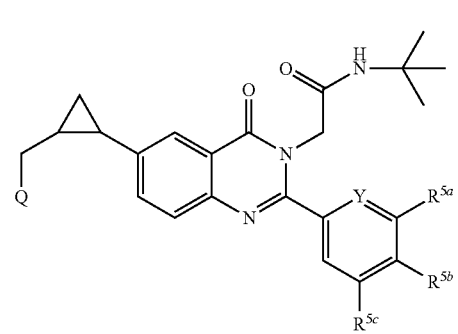
I.37
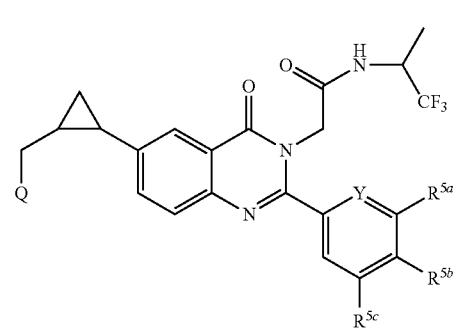
I.38
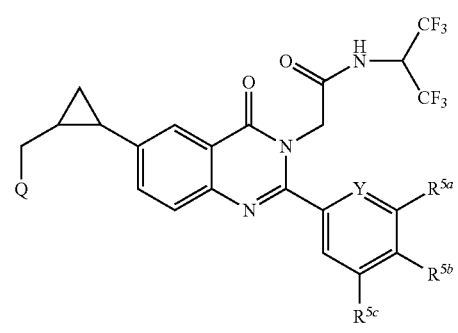

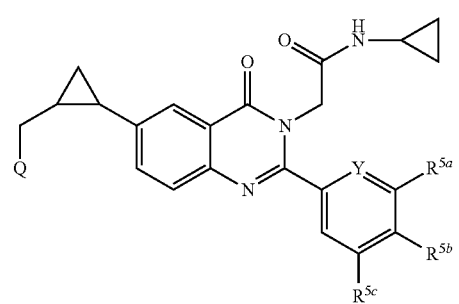
I.39
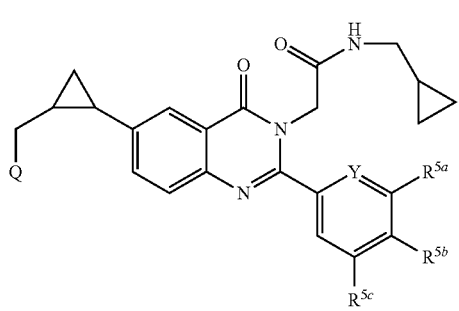
I.40
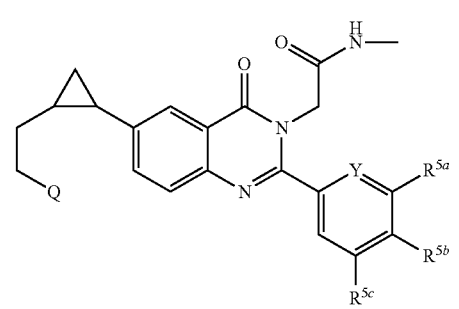
I.41
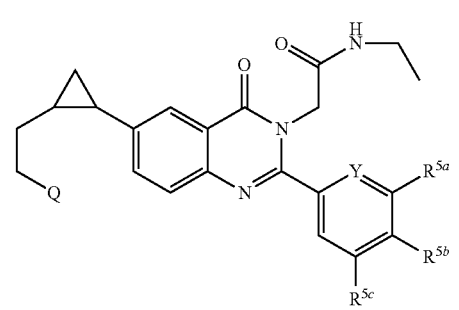
I.42
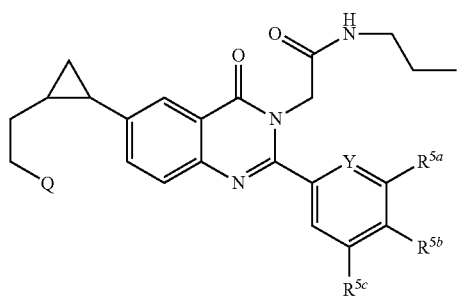
I.43
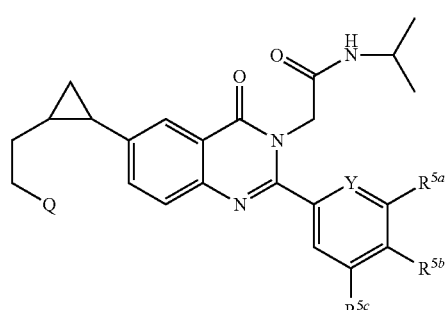
I.44
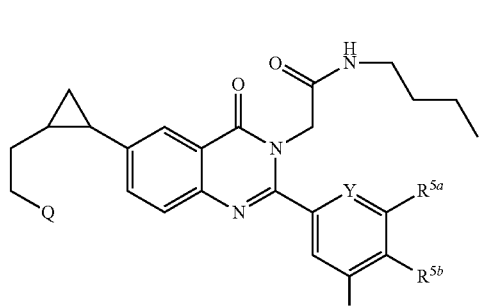
I.45
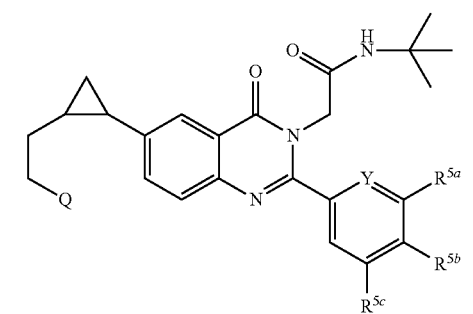
I.46
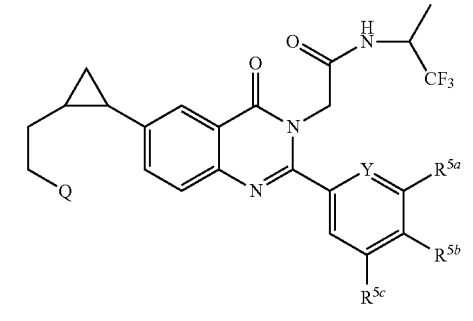
I.47
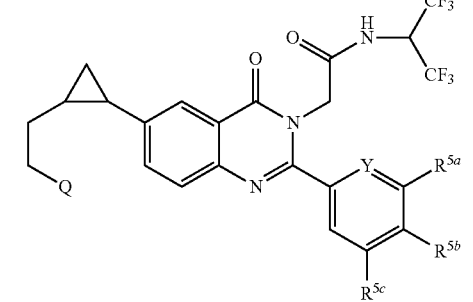
I.48

I.49

I.50

Table 1
Compounds of the formula I.1 in which Y is CH, Q is —N(CH$_3$)$_2$, and R$^{5a}$, R$^{5b}$ and R$^{5c}$ for a compound corresponds in each case to one row of Table A Table 2
Compounds of the formula I.1 in which Y is CH, Q is —N(CH$_2$CH$_3$)$_2$, and R$^{5a}$, R$^{5b}$ and R$^{5c}$ for a compound corresponds in each case to one row of Table A Table 3
Compounds of the formula I.1 in which Y is CH, Q is Q.1 (see below), and R$^{5a}$, R$^{5b}$ and R$^{5c}$ for a compound corresponds in each case to one row of Table A Table 4
Compounds of the formula I.1 in which Y is CH, Q is Q.2 (see below), and R$^{5a}$, R$^{5b}$ and R$^{5c}$ for a compound corresponds in each case to one row of Table A Table 5
Compounds of the formula I.1 in which Y is CH, Q is Q.3 (see below), and R$^{5a}$, R$^{5b}$ and R$^{5c}$ for a compound corresponds in each case to one row of Table A Table 6
Compounds of the formula I.1 in which Y is CH, Q is Q.4 (see below), and R$^{5a}$, R$^{5b}$ and R$^{5c}$ for a compound corresponds in each case to one row of Table A Table 7
Compounds of the formula I.1 in which Y is CH, Q is Q.5 (see below), and R$^{5a}$, R$^{5b}$ and R$^{5c}$ for a compound corresponds in each case to one row of Table A Table 8
Compounds of the formula I.1 in which Y is CH, Q is Q.6 (see below), and R$^{5a}$, R$^{5b}$ and R$^{5c}$ for a compound corresponds in each case to one row of Table A Table 9
Compounds of the formula I.1 in which Y is CH, Q is Q.7 (see below), and R$^{5a}$, R$^{5b}$ and R$^{5c}$ for a compound corresponds in each case to one row of Table A Table 10
Compounds of the formula I.1 in which Y is CH, Q is Q.8 (see below), and R$^{5a}$, R$^{5b}$ and R$^{5c}$ for a compound corresponds in each case to one row of Table A Table 11
Compounds of the formula I.1 in which Y is CH, Q is Q.9 (see below), and R$^{5a}$, R$^{5b}$ and R$^{5c}$ for a compound corresponds in each case to one row of Table A Table 12
Compounds of the formula I.1 in which Y is CH, Q is Q.10 (see below), and R$^{5a}$, R$^{5b}$ and R$^{5c}$ for a compound corresponds in each case to one row of Table A Table 13
Compounds of the formula I.1 in which Y is CH, Q is Q.11 (see below), and R$^{5a}$, R$^{5b}$ and R$^{5c}$ for a compound corresponds in each case to one row of Table A Table 14
Compounds of the formula I.1 in which Y is CH, Q is Q.12 (see below), and R$^{5a}$, R$^{5b}$ and R$^{5c}$ for a compound corresponds in each case to one row of Table A Table 15
Compounds of the formula I.1 in which Y is CH, Q is Q.13 (see below), and R$^{5a}$, R$^{5b}$ and R$^{5c}$ for a compound corresponds in each case to one row of Table A Table 16
Compounds of the formula I.1 in which Y is CH, Q is Q.14 (see below), and R$^{5a}$, R$^{5b}$ and R$^{5c}$ for a compound corresponds in each case to one row of Table A Table 17
Compounds of the formula I.1 in which Y is CH, Q is Q.15 (see below), and R$^{5a}$, R$^{5b}$ and R$^{5c}$ for a compound corresponds in each case to one row of Table A Table 18
Compounds of the formula I.1 in which Y is CH, Q is Q.16 (see below), and R$^{5a}$, R$^{5b}$ and R$^{5c}$ for a compound corresponds in each case to one row of Table A Table 19
Compounds of the formula I.1 in which Y is CH, Q is Q.17 (see below), and R$^{5a}$, R$^{5b}$ and R$^{5c}$ for a compound corresponds in each case to one row of Table A Table 20
Compounds of the formula I.1 in which Y is CH, Q is Q.18 (see below), and R$^{5a}$, R$^{5b}$ and R$^{5c}$ for a compound corresponds in each case to one row of Table A Table 21
Compounds of the formula I.1 in which Y is CH, Q is Q.19 (see below), and R$^{5a}$, R$^{5b}$ and R$^{5c}$ for a compound corresponds in each case to one row of Table A Table 22
Compounds of the formula I.1 in which Y is CH, Q is Q.20 (see below), and R$^{5a}$, R$^{5b}$ and R$^{5c}$ for a compound corresponds in each case to one row of Table A Table 23
Compounds of the formula I.1 in which Y is CH, Q is Q.21 (see below), and R$^{5a}$, R$^{5b}$ and R$^{5c}$ for a compound corresponds in each case to one row of Table A Table 24
Compounds of the formula I.1 in which Y is CH, Q is Q.22 (see below), and R$^{5a}$, R$^{5b}$ and R$^{5c}$ for a compound corresponds in each case to one row of Table A Table 25
Compounds of the formula I.1 in which Y is CH, Q is Q.23 (see below), and R$^{5a}$, R$^{5b}$ and R$^{5c}$ for a compound corresponds in each case to one row of Table A Table 26
Compounds of the formula I.1 in which Y is CH, Q is Q.24 (see below), and R$^{5a}$, R$^{5b}$ and R$^{5c}$ for a compound corresponds in each case to one row of Table A Table 27
Compounds of the formula I.1 in which Y is CH, Q is Q.25 (see below), and $R^{5a}$, $R^{5b}$ and $R^{5c}$ for a compound corresponds in each case to one row of Table A Table 28
Compounds of the formula I.1 in which Y is CH, Q is Q.26 (see below), and $R^{5a}$, $R^{5b}$ and $R^{5c}$ for a compound corresponds in each case to one row of Table A Table 29
Compounds of the formula I.1 in which Y is CH, Q is Q.27 (see below), and $R^{5a}$, $R^{5b}$ and $R^{5c}$ for a compound corresponds in each case to one row of Table A Table 30
Compounds of the formula I.1 in which Y is CH, Q is Q.28 (see below), and $R^{5a}$, $R^{5b}$ and $R^{5c}$ for a compound corresponds in each case to one row of Table A Table 31
Compounds of the formula I.1 in which Y is CH, Q is Q.29 (see below), and $R^{5a}$, $R^{5b}$ and $R^{5c}$ for a compound corresponds in each case to one row of Table A Table 32
Compounds of the formula I.1 in which Y is CH, Q is Q.30 (see below), and $R^{5a}$, $R^{5b}$ and $R^{5c}$ for a compound corresponds in each case to one row of Table A Table 33
Compounds of the formula I.1 in which Y is CH, Q is Q.31 (see below), and $R^{5a}$, $R^{5b}$ and $R^{5c}$ for a compound corresponds in each case to one row of Table A Table 34
Compounds of the formula I.1 in which Y is CH, Q is Q.32 (see below), and $R^{5a}$, $R^{5b}$ and $R^{5c}$ for a compound corresponds in each case to one row of Table A Table 35
Compounds of the formula I.1 in which Y is CH, Q is Q.33 (see below), and $R^{5a}$, $R^{5b}$ and $R^{5c}$ for a compound corresponds in each case to one row of Table A Table 36
Compounds of the formula I.1 in which Y is CH, Q is Q.34 (see below), and $R^{5a}$, $R^{5b}$ and $R^{5c}$ for a compound corresponds in each case to one row of Table A Table 37
Compounds of the formula I.1 in which Y is CH, Q is Q.35 (see below), and $R^{5a}$, $R^{5b}$ and $R^{5c}$ for a compound corresponds in each case to one row of Table A Table 38
Compounds of the formula I.1 in which Y is CH, Q is Q.36 (see below), and $R^{5a}$, $R^{5b}$ and $R^{5c}$ for a compound corresponds in each case to one row of Table A Table 39
Compounds of the formula I.1 in which Y is CH, Q is Q.37 (see below), and $R^{5a}$, $R^{5b}$ and $R^{5c}$ for a compound corresponds in each case to one row of Table A Table 40
Compounds of the formula I.1 in which Y is CH, Q is Q.38 (see below), and $R^{5a}$, $R^{5b}$ and $R^{5c}$ for a compound corresponds in each case to one row of Table A Table 41
Compounds of the formula I.1 in which Y is CH, Q is Q.39 (see below), and $R^{5a}$, $R^{5b}$ and $R^{5c}$ for a compound corresponds in each case to one row of Table A Tables 42 to 82
Compounds of the formula I.1 in which Y is N, Q is as defined in tables 1 to 41, and $R^{5a}$, $R^{5b}$ and $R^{5c}$ for a compound corresponds in each case to one row of Table A Tables 83 to 164
Compounds of the formula I.2 in which Y and Q are as defined in tables 1 to 82, and $R^{5a}$, $R^{5b}$ and $R^{5c}$ for a compound corresponds in each case to one row of Table A Tables 165 to 246
Compounds of the formula I.3 in which Y and Q are as defined in tables 1 to 82, and $R^{5a}$, $R^{5b}$ and $R^{5c}$ for a compound corresponds in each case to one row of Table A Tables 247 to 328
Compounds of the formula I.4 in which Y and Q are as defined in tables 1 to 82, and $R^{5a}$, $R^{5b}$ and $R^{5c}$ for a compound corresponds in each case to one row of Table A Tables 329 to 410
Compounds of the formula I.5 in which Y and Q are as defined in tables 1 to 82, and $R^{5a}$, $R^{5b}$ and $R^{5c}$ for a compound corresponds in each case to one row of Table A Tables 411 to 492
Compounds of the formula I.6 in which Y and Q are as defined in tables 1 to 82, and $R^{5a}$, $R^{5b}$ and $R^{5c}$ for a compound corresponds in each case to one row of Table A Tables 493 to 574
Compounds of the formula I.7 in which Y and Q are as defined in tables 1 to 82, and $R^{5a}$, $R^{5b}$ and $R^{5c}$ for a compound corresponds in each case to one row of Table A Tables 575 to 656
Compounds of the formula I.8 in which Y and Q are as defined in tables 1 to 82, and $R^{5a}$, $R^{5b}$ and $R^{5c}$ for a compound corresponds in each case to one row of Table A Tables 657 to 738
Compounds of the formula I.9 in which Y and Q are as defined in tables 1 to 82, and $R^{5a}$, $R^{5b}$ and $R^{5c}$ for a compound corresponds in each case to one row of Table A Tables 739 to 820
Compounds of the formula I.10 in which Y and Q are as defined in tables 1 to 82, and $R^{5a}$, $R^{5b}$ and $R^{5c}$ for a compound corresponds in each case to one row of Table A Tables 821 to 902
Compounds of the formula I.11 in which Y and Q are as defined in tables 1 to 82, and $R^{5a}$, $R^{5b}$ and $R^{5c}$ for a compound corresponds in each case to one row of Table A Tables 903 to 984
Compounds of the formula I.12 in which Y and Q are as defined in tables 1 to 82, and $R^{5a}$, $R^{5b}$ and $R^{5c}$ for a compound corresponds in each case to one row of Table A Tables 985 to 1066
Compounds of the formula I.13 in which Y and Q are as defined in tables 1 to 82, and $R^{5a}$, $R^{5b}$ and $R^{5c}$ for a compound corresponds in each case to one row of Table A Tables 1067 to 1148
Compounds of the formula I.14 in which Y and Q are as defined in tables 1 to 82, and $R^{5a}$, $R^{5b}$ and $R^{5c}$ for a compound corresponds in each case to one row of Table A Tables 1149 to 1230
Compounds of the formula I.15 in which Y and Q are as defined in tables 1 to 82, and $R^{5a}$, $R^{5b}$ and $R^{5c}$ for a compound corresponds in each case to one row of Table A Tables 1231 to 1312
Compounds of the formula I.16 in which Y and Q are as defined in tables 1 to 82, and $R^{5a}$, $R^{5b}$ and $R^{5c}$ for a compound corresponds in each case to one row of Table A Tables 1313 to 1394
Compounds of the formula I.17 in which Y and Q are as defined in tables 1 to 82, and $R^{5a}$, $R^{5b}$ and $R^{5c}$ for a compound corresponds in each case to one row of Table A Tables 1395 to 1476
Compounds of the formula I.18 in which Y and Q are as defined in tables 1 to 82, and $R^{5a}$, $R^{5b}$ and $R^{5c}$ for a compound corresponds in each case to one row of Table A Tables 1477 to 1558

Compounds of the formula I.19 in which Y and Q are as defined in tables 1 to 82, and $R^{5a}$, $R^{5b}$ and $R^{5c}$ for a compound corresponds in each case to one row of Table A Tables 1559 to 1640

Compounds of the formula I.20 in which Y and Q are as defined in tables 1 to 82, and $R^{5a}$, $R^{5b}$ and $R^{5c}$ for a compound corresponds in each case to one row of Table A Tables 1641 to 1722

Compounds of the formula I.21 in which Y and Q are as defined in tables 1 to 82, and $R^{5a}$, $R^{5b}$ and $R^{5c}$ for a compound corresponds in each case to one row of Table A Tables 1723 to 1804

Compounds of the formula I.22 in which Y and Q are as defined in tables 1 to 82, and $R^{5a}$, $R^{5b}$ and $R^{5c}$ for a compound corresponds in each case to one row of Table A Tables 1805 to 1886

Compounds of the formula I.23 in which Y and Q are as defined in tables 1 to 82, and $R^{5a}$, $R^{5b}$ and $R^{5c}$ for a compound corresponds in each case to one row of Table A Tables 1887 to 1968

Compounds of the formula I.24 in which Y and Q are as defined in tables 1 to 82, and $R^{5a}$, $R^{5b}$ and $R^{5c}$ for a compound corresponds in each case to one row of Table A Tables 1969 to 2050

Compounds of the formula I.25 in which Y and Q are as defined in tables 1 to 82, and $R^{5a}$, $R^{5b}$ and $R^{5c}$ for a compound corresponds in each case to one row of Table A Tables 2051 to 2132

Compounds of the formula I.26 in which Y and Q are as defined in tables 1 to 82, and $R^{5a}$, $R^{5b}$ and $R^{5c}$ for a compound corresponds in each case to one row of Table A Tables 2133 to 2214

Compounds of the formula I.27 in which Y and Q are as defined in tables 1 to 82, and $R^{5a}$, $R^{5b}$ and $R^{5c}$ for a compound corresponds in each case to one row of Table A Tables 2215 to 2296

Compounds of the formula I.28 in which Y and Q are as defined in tables 1 to 82, and $R^{5a}$, $R^{5b}$ and $R^{5c}$ for a compound corresponds in each case to one row of Table A Tables 2297 to 2378

Compounds of the formula I.29 in which Y and Q are as defined in tables 1 to 82, and $R^{5a}$, $R^{5b}$ and $R^{5c}$ for a compound corresponds in each case to one row of Table A Tables 2379 to 2460

Compounds of the formula I.30 in which Y and Q are as defined in tables 1 to 82, and $R^{5a}$, $R^{5b}$ and $R^{5c}$ for a compound corresponds in each case to one row of Table A Tables 2461 to 2542

Compounds of the formula I.31 in which Y and Q are as defined in tables 1 to 82, and $R^{5a}$, $R^{5b}$ and $R^{5c}$ for a compound corresponds in each case to one row of Table A Tables 2543 to 2624

Compounds of the formula I.32 in which Y and Q are as defined in tables 1 to 82, and $R^{5a}$, $R^{5b}$ and $R^{5c}$ for a compound corresponds in each case to one row of Table A Tables 2625 to 2706

Compounds of the formula I.33 in which Y and Q are as defined in tables 1 to 82, and $R^{5a}$, $R^{5b}$ and $R^{5c}$ for a compound corresponds in each case to one row of Table A Tables 2707 to 2788

Compounds of the formula I.34 in which Y and Q are as defined in tables 1 to 82, and $R^{5a}$, $R^{5b}$ and $R^{5c}$ for a compound corresponds in each case to one row of Table A Tables 2789 to 2870

Compounds of the formula I.35 in which Y and Q are as defined in tables 1 to 82, and $R^{5a}$, $R^{5b}$ and $R^{5c}$ for a compound corresponds in each case to one row of Table A Tables 2871 to 2952

Compounds of the formula I.36 in which Y and Q are as defined in tables 1 to 82, and $R^{5a}$, $R^{5b}$ and $R^{5c}$ for a compound corresponds in each case to one row of Table A Tables 2953 to 3034

Compounds of the formula I.37 in which Y and Q are as defined in tables 1 to 82, and $R^{5a}$, $R^{5b}$ and $R^{5c}$ for a compound corresponds in each case to one row of Table A Tables 2461 to 3116

Compounds of the formula I.38 in which Y and Q are as defined in tables 1 to 82, and $R^{5a}$, $R^{5b}$ and $R^{5c}$ for a compound corresponds in each case to one row of Table A Tables 3117 to 3198

Compounds of the formula I.39 in which Y and Q are as defined in tables 1 to 82, and $R^{5a}$, $R^{5b}$ and $R^{5c}$ for a compound corresponds in each case to one row of Table A Tables 3199 to 3280

Compounds of the formula I.40 in which Y and Q are as defined in tables 1 to 82, and $R^{5a}$, $R^{5b}$ and $R^{5c}$ for a compound corresponds in each case to one row of Table A Tables 3281 to 3362

Compounds of the formula I.41 in which Y and Q are as defined in tables 1 to 82, and $R^{5a}$, $R^{5b}$ and $R^{5c}$ for a compound corresponds in each case to one row of Table A Tables 3363 to 3444

Compounds of the formula I.42 in which Y and Q are as defined in tables 1 to 82, and $R^{5a}$, $R^{5b}$ and $R^{5c}$ for a compound corresponds in each case to one row of Table A Tables 3445 to 3526

Compounds of the formula I.43 in which Y and Q are as defined in tables 1 to 82, and $R^{5a}$, $R^{5b}$ and $R^{5c}$ for a compound corresponds in each case to one row of Table A Tables 3527 to 3608

Compounds of the formula I.44 in which Y and Q are as defined in tables 1 to 82, and $R^{5a}$, $R^{5b}$ and $R^{5c}$ for a compound corresponds in each case to one row of Table A Tables 3609 to 3690

Compounds of the formula I.45 in which Y and Q are as defined in tables 1 to 82, and $R^{5a}$, $R^{5b}$ and $R^{5c}$ for a compound corresponds in each case to one row of Table A Tables 3691 to 3772

Compounds of the formula I.46 in which Y and Q are as defined in tables 1 to 82, and $R^{5a}$, $R^{5b}$ and $R^{5c}$ for a compound corresponds in each case to one row of Table A Tables 3773 to 3854

Compounds of the formula I.47 in which Y and Q are as defined in tables 1 to 82, and $R^{5a}$, $R^{5b}$ and $R^{5c}$ for a compound corresponds in each case to one row of Table A Tables 3855 to 3936

Compounds of the formula I.48 in which Y and Q are as defined in tables 1 to 82, and $R^{5a}$, $R^{5b}$ and $R^{5c}$ for a compound corresponds in each case to one row of Table A Tables 3936 to 4018

Compounds of the formula I.49 in which Y and Q are as defined in tables 1 to 82, and $R^{5a}$, $R^{5b}$ and $R^{5c}$ for a compound corresponds in each case to one row of Table A Tables 4019 to 4100

Compounds of the formula I.50 in which Y and Q are as defined in tables 1 to 82, and $R^{5a}$, $R^{5b}$ and $R^{5c}$ for a compound corresponds in each case to one row of Table A Q.1 to Q.39:

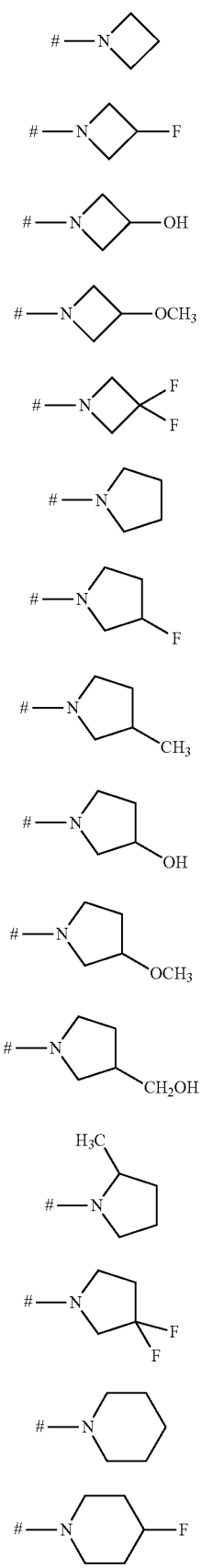
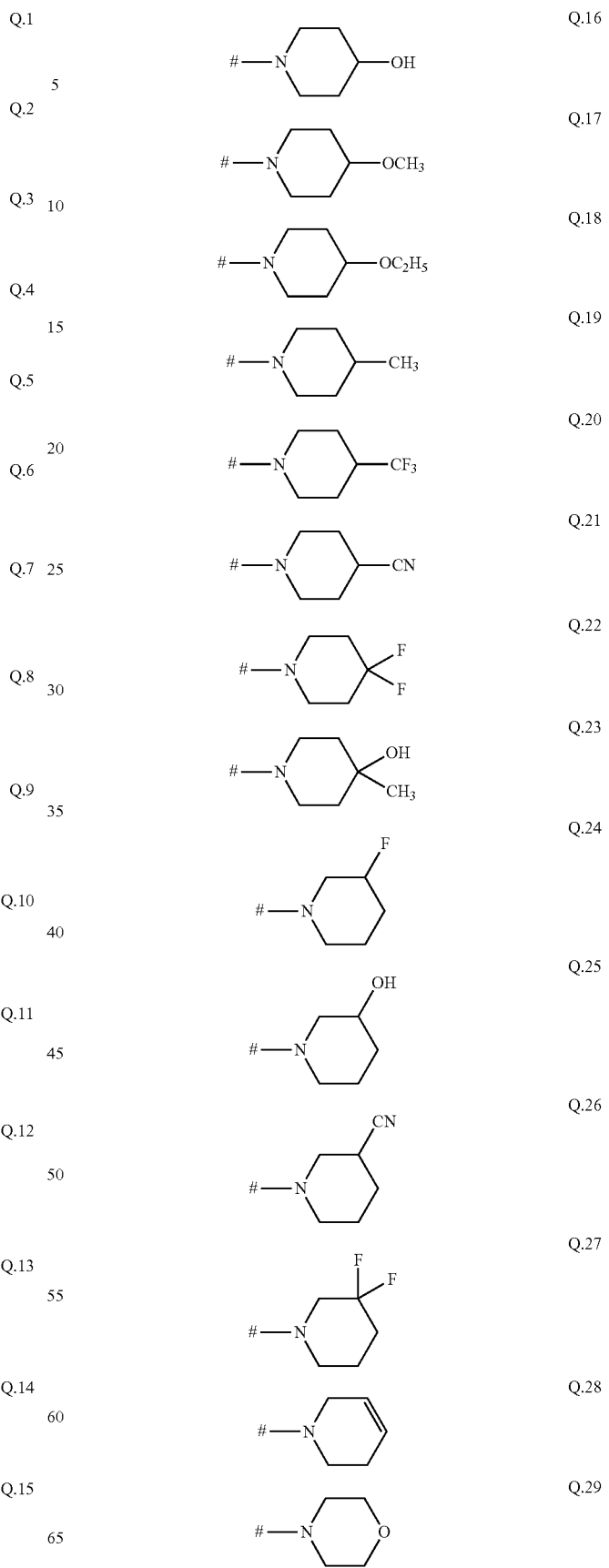

-continued

Q.30 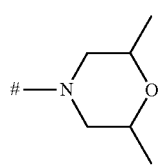

Q.31 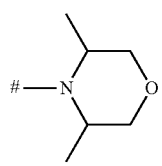

Q.32 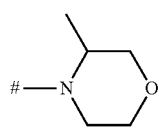

Q.32 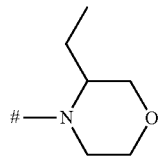

Q.33 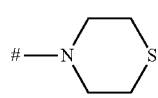

Q.34 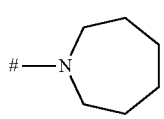

Q.35 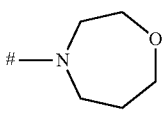

Q.36 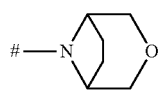

Q.37 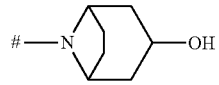

Q.38 

Q.39 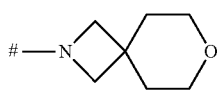

\# is the attachment point to the remainder of the molecule.

TABLE A

| No. | $R^{5a}$ | $R^{5b}$ | $R^{5c}$ |
| --- | --- | --- | --- |
| A-1. | H | H | H |
| A-2. | Cl | H | H |
| A-3. | F | H | H |
| A-4. | Br | H | H |
| A-5. | CN | H | H |
| A-6. | $CH_3$ | H | H |
| A-7. | $C_2H_5$ | H | H |
| A-8. | $CH_2CH_2CH_3$ | H | H |
| A-9. | $CH(CH_3)_2$ | H | H |
| A-10. | $CHF_2$ | H | H |
| A-11. | $CF_3$ | H | H |
| A-12. | $OCH_3$ | H | H |
| A-13. | $OC_2H_5$ | H | H |
| A-14. | $OCHF_2$ | H | H |
| A-15. | $OCF_3$ | H | H |
| A-16. | Cl | F | H |
| A-17. | Cl | H | $OCF_3$ |
| A-18. | $OCH_3$ | F | H |
| A-19. | $OCH_3$ | H | $OCH_3$ |
| A-20. | H | H | Cl |
| A-21. | H | H | F |
| A-22. | H | H | Br |
| A-23. | H | H | CN |
| A-24. | H | H | $CH_3$ |
| A-25. | H | H | $C_2H_5$ |
| A-26. | H | H | $CH_2CH_2CH_3$ |
| A-27. | H | H | $CH(CH_3)_2$ |
| A-28. | H | H | $CHF_2$ |
| A-29. | H | H | $CF_3$ |
| A-30. | H | H | $OCH_3$ |
| A-31. | H | H | $OC_2H_5$ |
| A-32. | H | H | $OCHF_2$ |
| A-33. | H | H | $OCF_3$ |
| A-34. | H | F | Cl |
| A-35. | $OCF_3$ | H | Cl |
| A-36. | H | F | $OCH_3$ |
| A-37. | —O—$CH_2CH_2$—O— | | H |
| A-38. | H | —O—$CH_2CH_2$—O— | |

Among the above compounds preference is given to compounds I.1 to I.10 and the stereoisomers thereof.

In a specific embodiment, the compounds I are selected from the compounds specified in the examples, either as a free base or in form of a pharmaceutically acceptable salt, an N-oxide or a stereoisomer or the racemate or any mixture of stereoisomers thereof.

The compounds I of the invention have a stereogenic center at the carbon atom forming the attachment point of $R^3$ to the remainder of the molecule (to be more precise to the fused ring system with ring members $X^1$ to $X^5$), as well as at the carbon atom in ring $R^3$ carrying $R^6$. Depending on the substitution pattern of ring $R^3$, the compounds of the invention may be present as essentially pure diastereomers (Z/E isomers) or as mixtures of diastereomers. "Essentially pure diastereomers" means here that one diastereomer is contained in at least 85% by weight, preferably at least 90% by weight, in particular at least 95% by weight, relative to the overall weight of all diastereomers. If ring $R^3$ does not contain a mirror plane, the diastereomers themselves may be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. "Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

Examples of synthetic routes for preparing the oxindole derivatives of the invention are described below.

The precursors of the compounds of the invention can be prepared, for example, by using methods described in WO 2006/095014, WO 2008/033764, WO 2008/071779, WO2010/037123, WO 2011/045258 or WO 2012/154760, and the preparation is outlined by way of example in synthesis schemes 1 to 7. If not indicated otherwise, the variables in these synthetic schemes have the same meanings as in formula I.

Compound 1, in which Z is Br, I or triflate ($CF_3SO_2O$), is converted into a boronic ester, such as the tetramethyldioxaborolane 2 shown in scheme 1 below. The tetramethyldioxaborolane group is suitably introduced using 4,4,4',4', 5,5,5',5'-octamethyl-2,2'-bis(1,3,2-dioxaborolane) in the presence of a Pd compound, e.g. $PdCl_2$(dppf), and a base, e.g. a carbonate, such as $Na_2CO_3$, $K_2CO_3$ or $Cs_2CO_3$; an acetate, e.g. sodium acetate; pyridine, and the like. Other boronic ester groups can e.g. be introduced e.g. by metallating 1 (i.e. replacing Z by a metal, e.g. Li; e.g. by reaction of 1 with n-butyllithium or methyllithium) and then reacting the metallated compound with a boronic ester $B(OR)_3$, wherein R is $C_1$-$C_4$-alkyl; especially isopropyl, or boronic acid. The boronic ester or acid 2 (or other analogous boronic esters not shown in scheme 1) is then reacted with triflate 3 in a Suzuki reaction to 4. In 3, PG is an oxygen-protective group, especially a silyl protective group, such as trimethylsilyl (TMS), triethylsilyl (TES), triisopropylsilyl (TIPS), tert-butyldimethylsilyl (TBDMS) or tert-butyldiphenylsilyl (TBDPS); A is $C_1$-$C_4$-alkylene or fluorinated $C_1$-$C_4$-alkylene, G is $C_3$-$C_6$-cycloalkenylene with a double bond in 1-position, relative to the 1-position of OTf and Tf is triflate ($CF_3SO_2$). The reaction is carried in the presence of a palladium compound and a base, such as $Na_2CO_3$, $K_2CO_3$ or $Cs_2CO_3$; an acetate, e.g. sodium acetate; pyridine, and the like. Instead of the triflate 3, the corresponding bromide or iodide can be used (instead of OTf in 3: Br or I). Deprotection of 4 yields 5. The deprotection agent depends on the protective group PG used. For example, TMS can be removed with KF in acetic acid; TES with trifluoroacetic acid in water/THF, HF or pyridinium hydrofluoride in pyridine, and TIPS, TBDMS and TBDPS with acetic acid in water/THF, pyridinium tosylate in methanol, trifluoroacetic acid in water, HF in acetonitrile, pyridinium hydrofluoride in THF or tetrabutylammoniumfluoride in THF. Mesylation of 5 (Ms=$CH_3S(\equiv O)_2$), e.g. by reaction with methansulfonyl chloride in the presence of a base, such as triethylamine, diisopropylethyl amine or pyridine, yields 6, which is then reacted with amine 7, suitably in the presence of a base, e.g. a carbonate, such as $Na_2CO_3$, $K_2CO_3$ or $Cs_2CO_3$; an acetate, e.g. sodium acetate; pyridine, and the like. In the resulting compound I, G is a cycloalkenyl substituent. This can be hydrogenated to the corresponding saturated cycloalkyl ring G, e.g. by hydrogenation in the presence of a suitable catalyst, such as Pt, Ni and the like. Especially if A is methylene or fluorinated methylene and $NR^{11}R^{12}$ is bulky, e.g. is an N-bound ring, hydrogenation generally yields as a major product a cycloalkyl ring G in which A-$NR^{11}R^{12}$ and the scaffold (i.e. the fused ring system containing $X^1$ to $X^5$ as ring members) are bound cis to each other.

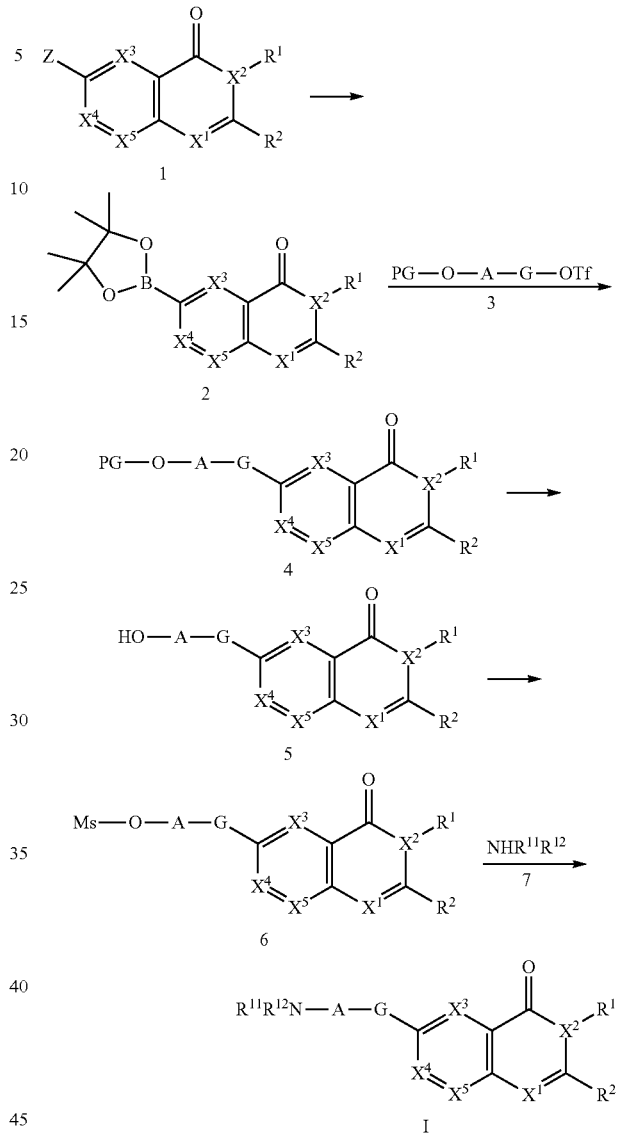

Scheme 1

Compounds I, wherein G is 1,2-cyclopropylene and A is $CH_2CH_2$ (termed compounds I' in the following) can moreover be synthesized as shown in scheme 2 below. Compound 1, wherein Z is Cl, Br or I, is reacted with butenol 8 in a Heck reaction in the presence of a palladium catalyst, such as Pd(II)acetate or Pd(II)chloride, and a phosphorous ligand, e.g. triphenylphosphine, tri-o-tolylphosphine, dppf etc., and a base, e.g. pyridine, triethylamine, diisopropylethylamine and the like, in a polar aprotic solvent, such as acetonitrile, to 9. Oxidative cleavage of the exocyclic double bond of 9 to the aldehyde 10 can be accomplished with sodium or potassium periodate in combination with osmium tetroxide or sodium or potassium periodate in combination with sodium or potassium permanganate or with chromic acid. 10 is then reacted with 4-methylbenzenesulfonylhydrazide 11 to the hydrazone 12 in the presence of a base, e.g. a carbonate, such as $Na_2CO_3$, $K_2CO_3$ or $Cs_2CO_3$; an acetate, e.g. sodium acetate; pyridine, and the like. Reaction of 12 with the butadienyl ester 13, wherein R is methyl or ethyl, in the presence of a base, e.g. a carbonate, such as $Na_2CO_3$, $K_2CO_3$ or $Cs_2CO_3$; an acetate, e.g. sodium acetate; pyridine, and the like, yields 14, which is hydrolyzed with a suitable base, especially a hydroxide, such as LiOH, NaOH or KOH, to 15. Reaction with amine 7, suitably in the presence of a base, e.g. a carbonate, such as $Na_2CO_3$, $K_2CO_3$ or $Cs_2CO_3$; an acetate, e.g. sodium acetate; pyridine, and the like, finally yields I'.

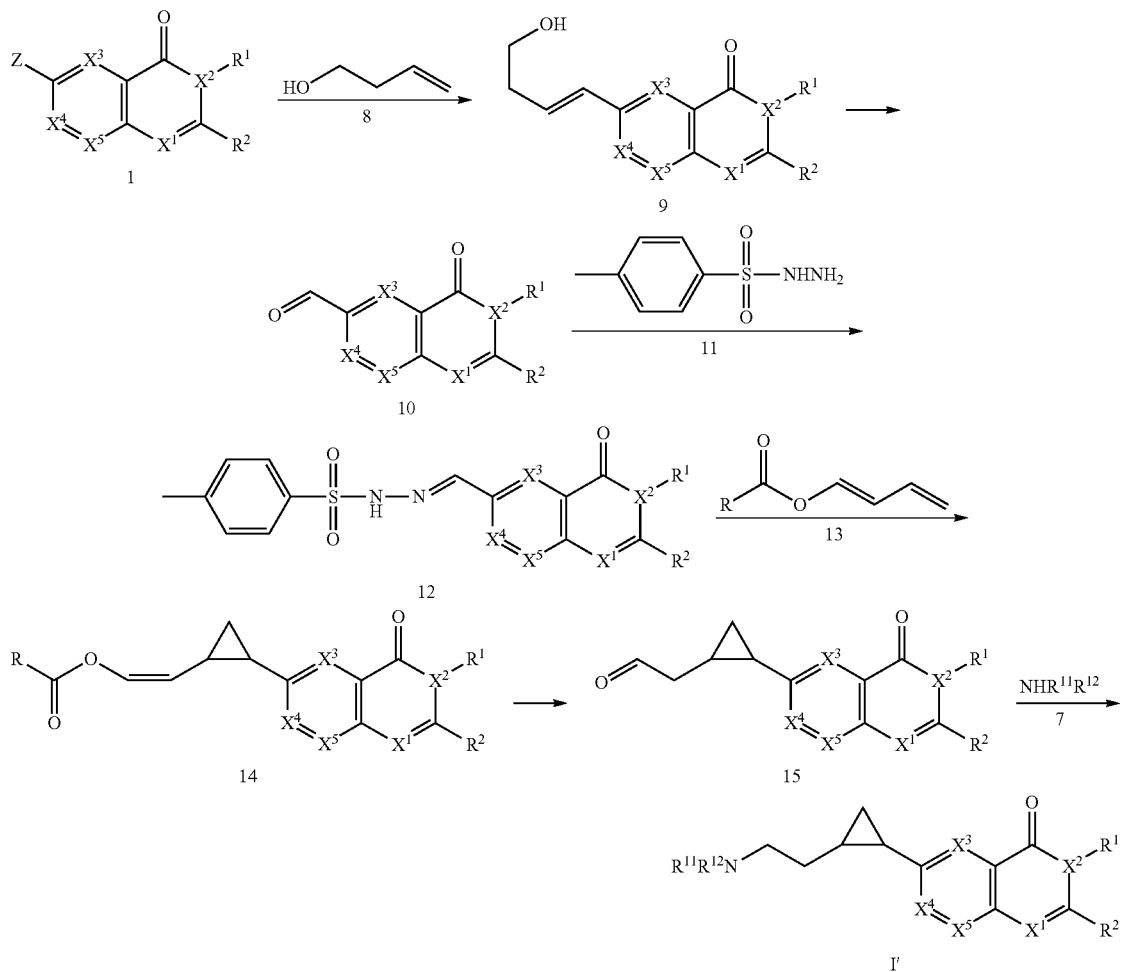

Compounds I, wherein G is 1,2-cyclopropylene and A is $CH_2$ (termed compounds I" in the following) can moreover be synthesized as shown in scheme 3 below. The hydrazone 12 is reacted with the acrylic ester 16, wherein R is methyl or ethyl, to 17. The reaction is generally carried out in the presence of a base, e.g. a carbonate, such as $Na_2CO_3$, $K_2CO_3$ or $Cs_2CO_3$; an acetate, e.g. sodium acetate; pyridine, and the like, at elevated temperature, e.g. under reflux. Suitably, a solvent with a high boiling point, preferably with a boiling point of at least 80° C., in particular at least 100° C., e.g. dioxane, dimethylsulfoxide or diethylene glycol, is used. Ester 17 is then reduced to alcohol 18. Suitable reduction agents are for example lithium aluminium hydride (LAH) or diisobutylaluminium hydride (DIBAL-H) under reaction conditions typically used for these complex hydrides, e.g. low temperatures, e.g. at most −20° C., preferably at most −50° C., in particular at most −70° C., and non-coordinating solvents, e.g. dichloromethane, toluene or hexene. Alternatively, Bouveault Blanc reaction conditions (sodium ethanol) can be used. Oxidation of the alcohol 18 yields the aldehyde 19. Suitable oxidation agents are Dess-Martin-periodinane, Cr(VI) reagents, such as $CrO_3$ (generally in pyridine), pyridiniumchlorochromate or pyridiniumdichromate, dimethylsulfoxide in combination with oxalylchloride and triethylamine (Swern oxidation) or tetramethylpiperidin-nitroxyl (TEMPO). Alternatively, ester 17 can be reduced carefully to the aldehyde 19 using suitable conditions, such as DIBAL-H under mild conditions (low temperature below −70° C., short reaction time) or LiAlH(O-tert-butyl)$_3$. Reaction with amine 7, suitably in the presence of a base, e.g. a carbonate, such as $Na_2CO_3$, $K_2CO_3$ or $Cs_2CO_3$; an acetate, e.g. sodium acetate; pyridine, and the like, finally yields I".

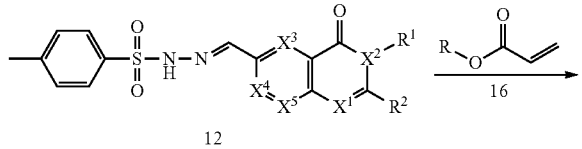

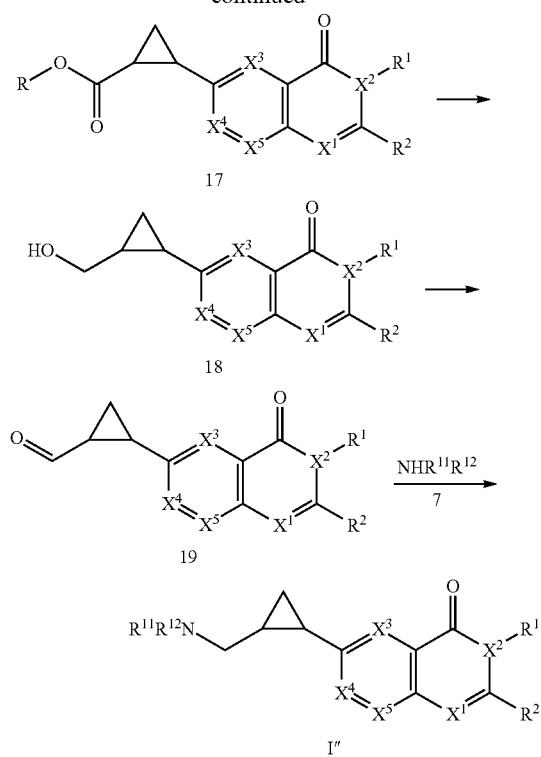

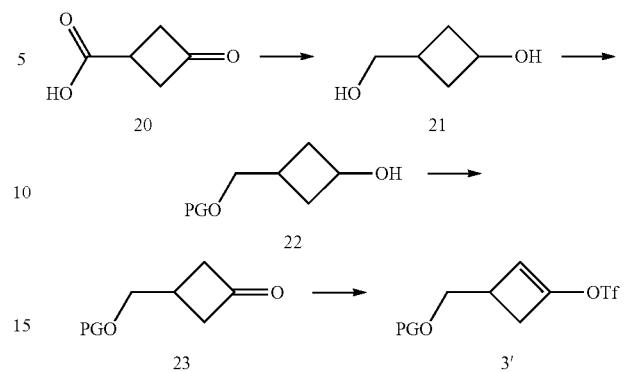

Compounds 3 wherein G is 1,3-cyclobutylene and A is $CH_2CH_2$ (termed below compound 3″) can be synthesized as shown in scheme 5 below. Butenol 24 is protected as described above, e.g. by reaction with trimethylsilyl chloride, triethylsilyl chloride, triisopropylsilyl chloride, tert-butyldimethylsilyl chloride or tert-butyldiphenylsilyl chloride. Reaction of 25 with trichloracetyl chloride in the presence of Zn or Cu—Zn alloy gives 26. This reaction corresponds to [2+2] cycloaddition, as trichloracetyl chloride reacts in situ in the presence of Zn or Cu—Zn alloy to dichloroketene which reacts in turn in a [2+2] cycloaddition with the C=C double bond of 25. The chloro atoms of 26 are removed with Zn in acetic acid to give 27. Deprotonation of the latter with a strong non-nucleophilc base, such as lithium bis(trimethylsilyl)amide (LiHMDS; lithium hexamethyldisilazide) or lithiumdiisopropylamide (LDA), followed by reaction with a triflate-introducing agent, such as 1,1,1-trifluoro-N-phenyl-N-((trifluoromethyl)sulfonyl)methanesulfonamide, yields 3″.

Compounds 3 can be synthesized as shown in schemes 4 or 5 below. 3-Oxocyclobutanecarboxylic acid 20 is reduced to the alcohol 21. Suitable reduction agents are those listed above for the reduction of ester 17 to alcohol 18, and further also boranes, such as diborane, borane adducts, such as $BH_3.DMS$ (dimethylsulfide) or $BH_3.THF$ (tetrahydrofuran) or $BH_3$.diethylether. Protection with PG yields 22. PG is an oxygen-protective group, especially a silyl protective group, such as trimethylsilyl (TMS), triethylsilyl (TES), triisopropylsilyl (TIPS), tert-butyldimethylsilyl (TBDMS) or tert-butyldiphenylsilyl (TBDPS). These are generally introduced by reacting 21 with the respective silyl chloride, i.e. trimethylsilyl chloride, triethylsilyl chloride, triisopropylsilyl chloride, tert-butyldimethylsilyl chloride or tert-butyldiphenylsilyl chloride. The reaction is generally carried out in the presence of a base. Suitable bases are listed above. In order to favor protection of only the aliphatic OH group, the reaction can be carried out kinetically controlled, i.e. at rather low temperatures, e.g. at a temperature below 10° C., e.g. at about 0° C., for a rather short reaction time. Oxidation to the cyclobutanone 23 is accomplished with a suitable oxidation agent, such as those listed above, i.e. Dess-Martin-periodinane, Cr(VI) reagents, such as $CrO_3$ (generally in pyridine), pyridiniumchlorochromate or pyridiniumdichromate, dimethylsulfoxide in combination with oxalylchloride and triethylamine (Swern oxidation) or tetramethylpiperidin-nitroxyl (TEMPO). Deprotonation of 23 with a strong non-nucleophilc base, such as lithium bis(trimethylsilyl)amide (LiHMDS; lithium hexamethyldisilazide) or lithium-diisopropylamide (LDA), followed by reaction with a triflate-introducing agent, such as 1,1,1-trifluoro-N-phenyl-N-((trifluoromethyl)sulfonyl)methanesulfonamide, yields 3′; i.e. a compound 3 wherein G is cyclobut-1-enyl and A is $CH_2$.

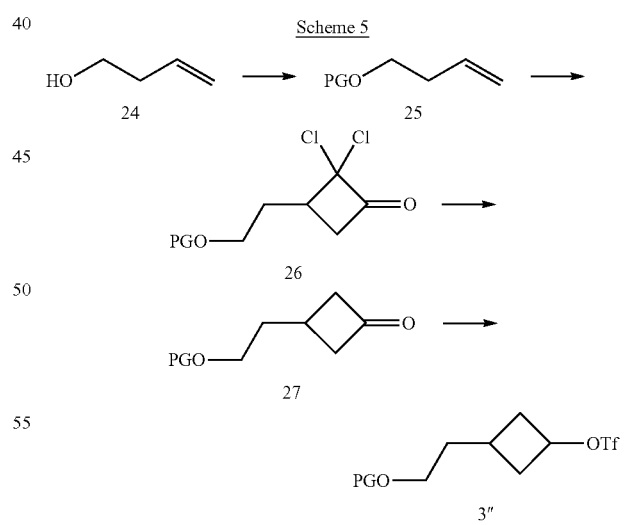

Compounds 1, wherein $X^1$ and $X^2$ are N (termed compounds 1′), can be produced as shown in scheme 6 below. Amidation of 28 with amine 29 can be carried out by heating and removal of reaction water, but is preferably carried out by activation of the acid group in 28 with oxalylchloride [$(COCl)_2$] or thionylchloride ($SOCl_2$) to the respective acid chloride, followed by reaction with amine 29. Alternatively, amidation is carried out in the presence of a coupling reagent. Suitable coupling reagent (activators) are well known and are for instance selected from carbodiimides, such as DCC (dicyclohexylcarbodiimide) and DIC (diisopropylcarbodiimide), benzotriazole derivatives, such as HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate), HCTU (1H-benzotriazolium-1-[bis(dimethylamino)methylene]-5-chloro tetrafluoroborate) and 2-(3H-[1,2,3]triazolo[4,5-b]pyridin-3-yl)-1,1,3,3-tetramethylisouronium hexafluorophosphate(V); and phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate). Generally, the activator is used in excess. The benzotriazole and phosphonium coupling reagents are generally used in a basic medium. Reaction of amide 30 with 31, wherein X is a halogen atom, such as Cl or Br, in the presence of a base yields 32. Suitable bases are listed above. Intramolecular condensation using a suitable base such as lithium, sodium or potassium hydroxide yields 1'.

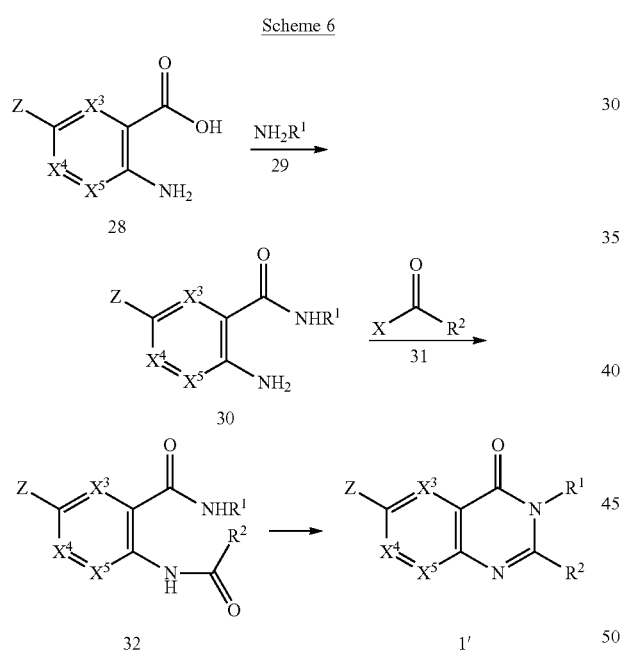

Scheme 6

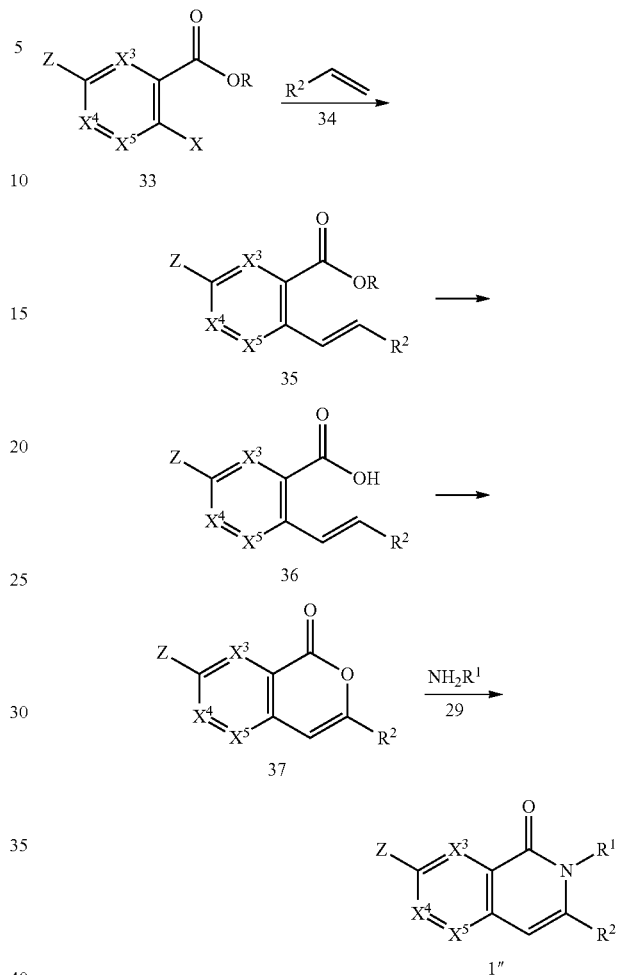

Scheme 7

Compounds 1, wherein $X^1$ is CH and $X^2$ is N (termed compounds 1″), can be produced in analogy to the method described in WO 2008/033764 and as shown in scheme 7 below. Heck reaction of 33, wherein X is a halogen atom, especially Cl or Br, and 34 in the presence of a palladium catalyst, such as Pd(II)acetate or Pd(II)chloride, and a phosphorous ligand, e.g. triphenylphosphine, tri-o-tolylphosphine, dppf etc., and a base, e.g. pyridine, triethylamine, diisopropylethylamine and the like, in a polar aprotic solvent, such as acetonitrile, gives 35. This is hydrolyzed either under acidic or basic conditions. The resulting acid 36 is cyclized to the compound 37 using a palladium catalyst, such as bis(acetonitrile)dichloropalladium(II), and an oxidizing agent, such as p-benzoquinone. Heating with amine 29 yields the isoquinolonone 1″.

Compounds 1, wherein $X^1$, $X^2$, $X^3$, $X^4$ and $X^5$ are CH (termed compounds 1‴), Z is Cl or Br and $R^1$ is —$CH_2$—$(CH_2)_n$. —C(O)OH with n being 0, 1, 2 or 3, can be prepared as shown in scheme 8 below. Reaction of ketone 38, in which n is 0, 1, 2 or 3, with sulfur and morpholine yields the corresponding thiomorpholide 39, in which n is 0, 1, 2 or 3. Typical reactions conditions are those of the Kindler modification of the Willgerodt-Kindler reaction (see e.g. M. Mujahid Alam, Srinivas R. Adapa, 2003, Synthetic Communications: An International Journal for Rapid Communication of Synthetic Organic Chemistry, 33:1, 59-63, DOI: 10.1081/SCC-120015559). Basic hydrolysis of 39 followed by acidification yields 1‴.

Scheme 8

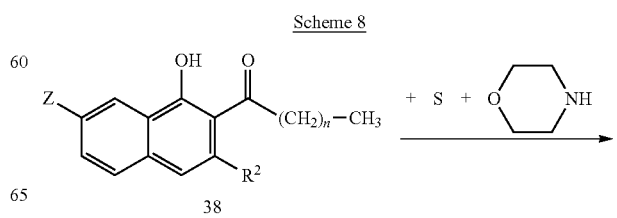

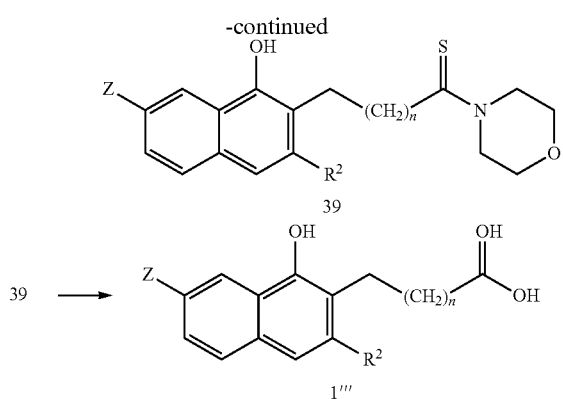

Compounds 1, wherein $X^1$, $X^2$, $X^3$, $X^4$ and $X^5$ are CH (termed compounds 1''''), Z is Cl or Br and $R^1$ is $(CH_2)_m$—$C(O)NR^9R^{10}$ with m being 1, 2, or 3 can be prepared as shown in scheme 9 below. Carbamate 40, in which m is 1, 2, 3 or 4, is reacted with a strong lithium base such as lithium diisopropylamine, phenyllithium or butyllithium, followed by acidic work-up to yield 1''''. Typical reactions conditions are those of the anionic Fries rearrangement (see e.g. A. V. Kalinin, M. A. J. Miah, S. Chattopadhyay, M. Tsukazaki, M. Wicki, T. Nguen, A. L. Coelho, M. Kerr and V. Snieckus, Synlett, 839 (1997)).

Scheme 9

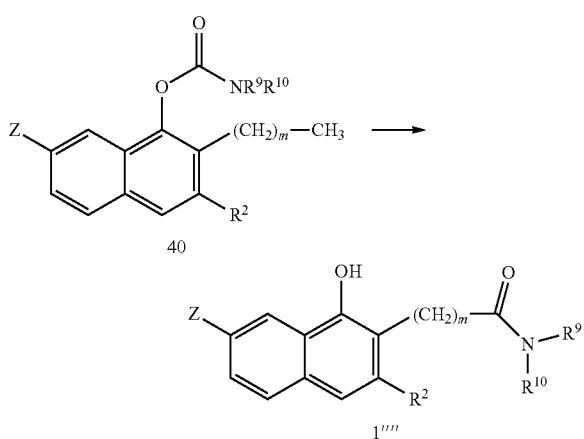

Compounds I where in $R^1$ the radical $R^4$ is OH can be converted into compounds I wherein $R^4$ is —$NR^9R^{10}$ by customary amidation reactions using $NHR^9R^{10}$ as amine Suitable amidation conditions are those described above for the amidation of 28. It is of course also possible to amidate precursors of compounds I.

The sequence of reaction steps can be varied. For example the cycloalkenylene ring G can be hydrogenated yet in compounds 4, 5 or 6, if compounds I with G being cycloalkylene are to be produced via the route shown in scheme 1.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the unlabeled compounds according to the invention might naturally include certain amounts of these respective isotopes. Therefore, when referring to compounds I, wherein at least one of the atoms has been replaced by its stable, non-radioactive isotope, it will be understood that the isotope is present in a higher amount than would naturally occur.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as D2SO4/D2O. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

Affective disorders have been related to excessive vasopressin function. Therefore, treatment with compounds targeting the vasopressin system, such as vasopressin antagonists are likely to benefit patients suffering from affective disorders (see for example Surget A., Belzung C., Involvement of vasopressin in affective disorders, Eur. J. Pharm. 2008, 583, 340-349). Affective disorders (mood disorders) include depressive disorders, anxiety disorders, obsessive-compulsive and related disorders, trauma and stressor-related disorders as well as bipolar and related disorders. V1b antagonist have been shown to have anti-drug abuse effects and reduce drug withdrawal effect (see e.g. Zhou Y., Leri F., Cummins E., Hoeschele M., Kreek M. J., Involvement of arginine vasopressin and V1b receptor in heroin withdrawal and heroin seeking precipitated by stress and by heroin. Neuropsychopharmacology, 2008, 33, 226-236). Therefore, compounds targeting the vasopressin system, such as vasopressin antagonists, are thought to be effective for treatment of substance-related and addictive disorders. V1b receptors play a role in a range of emotional responses such as aggression. Attenuating V1b receptor function genetically or with antagonist reduces aggressive behavior (Blanchard R. J., Griebel G., Farrokhi C., Markham C., Yang M., Blanchard D. C., AVP V1b selective antagonist SSR149415 blocks aggressive behaviors in hamsters. Pharmacol. Biochem. Behav. 2005, 80, 189-194; Wersinger S. R., Ginns E. I., O'Carroll A. M., Lolait S. J., Young W. S., III, Vasopressin V1b receptor knockout reduces aggressive behavior in male mice. Mol. Psychiatry, 2002, 7, 975-984). Therefore, attenuating V1b antagonists functioning is likely to reduce aggression and agitation in disorders such as Alzheimer's disease and schizophrenia and other psychiatric and neurological disorders in which aggressive behavior occurs, such as Alzheimer's disease, schizophrenia, bipolar disorder, frontal lobe injuries or substance use disorders.

High cortisol levels have been correlated to reduced cognitive performance in elderly and AD (Alzheimer's disease) patients, and such correlations are more pronounced in subjects carrying the APOϵ4 allele, which is a risk factor for AD (see for example Lee B. K., Glass T. A., Wand G. S., McAtee M. J., Bandeen-Roche K., Bolla K. I., Schwartz B. S., Apolipoprotein e genotype, cortisol, and cognitive function in community-dwelling older adults. Am. J. Psychiatry 2008, 165, 1456-1464). Furthermore, increased plasma cortisol has been associated with more rapid disease progression in AD patients. Animal studies show an interaction between glucocorticoids and AD pathology, including amyloid precursor protein and tau accumulation (see for example Budas G., Coughlan C. M., Seckl J. R., Breen K. C., The effect of corticosteroids on amyloid beta precursor protein/amyloid precursor-like protein expression and processing in vivo. Neurosci. Lett., 1999, 276, 61-64). Cognitive performance can be impaired by stress or exposure to high doses of corticosterone in laboratory animals (for review see Roozendaal B., Systems mediating acute glucocorticoid effects on memory consolidation and retrieval. Prog. Neuropsychopharmacol. Biol. Psychiatry, 2003, 27, 1213-1223). Therefore, lowering cortisol by treatment with V1b antagonist may enhance cognition or prevent/slow down the pathology or cognitive decline Alzheimer's disease patients and in patients with other cognitive impairment such as schizophrenia and depression.

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition; as well as to compounds of the invention of the formula I or of an N-oxide, a stereoisomer or of pharmaceutically acceptable salts thereof for the treatment and/or prophylaxis of the above-listed diseases. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness; as well as to compounds of the invention of the formula I or of an N-oxide, a stereoisomer or of pharmaceutically acceptable salts thereof for the treatment and/or prophylaxis of the above-listed diseases.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders, anxiety disorders, obsessive-compulsive and related disorders, trauma and stressor-related disorders, and bipolar and related disorders. Depressive disorders include for example dysthymic disorders, major depression, seasonal depression, treatment-resistant depression disorders, disruptive mood dysregulation disorder, premenstrual dysphoric disorder, substance/medication-induced depressive disorder, depressive disorder due to another medical condition, or childhood onset mood disorders. Anxiety disorders include for example phobias, specific phobias, general anxiety disorders, panic disorders, drug withdrawal-induced anxiety disorders, separation anxiety disorder, selective mutism, social anxiety disorder, agoraphobia, substance/medication-induced anxiety disorder and anxiety disorder due to another medical condition. Obsessive-compulsive and related disorders include for example obsessive-compulsive disorder, body dysmorphic disorder, hoarding disorder, trichotillomania, excoriation disorder, substance/medication-induced obsessive-compulsive and related disorder and other specified obsessive-compulsive and related disorders. Trauma and stressor-related disorders include for example reactive attachment disorder, disinhibited social engagement disorder, post-traumatic stress disorder, acute stress disorder, adjustment disorder and other specified trauma- and stressor-related disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, specific phobias, post-traumatic anxiety disorders, panic anxiety disorders, obsessive-compulsive anxiety disorders, acute stress-dependent anxiety disorders, drug withdrawal-induced anxiety disorders, separation anxiety disorder, selective mutism, social anxiety disorder, agoraphobia, substance/medication-induced anxiety disorder and anxiety disorder due to another medical condition and social phobia. The compounds of the invention of the formula I and their N-oxides, a stereoisomers or pharmaceutically acceptable salts or the pharmaceutical composition of the invention can likewise be employed for the treatment of obsessive-compulsive and related disorders, including, for example, obsessive-compulsive disorder, body dysmorphic disorder, hoarding disorder, trichotillomania, excoriation disorder, substance/medication-induced obsessive-compulsive and related disorder and other specified obsessive-compulsive and related disorders. The compounds of the invention of the formula I and their N-oxides, a stereoisomers or pharmaceutically acceptable salts or the pharmaceutical composition of the invention can likewise be employed for the treatment of trauma and stressor-related disorders, including, for example, reactive attachment disorder, disinhibited social engagement disorder, post-traumatic stress disorder, acute stress disorder, adjustment disorder and other specified trauma- and stressor-related disorders.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions selected from Alzheimer's disease, schizophrenia, bipolar disorder, frontal lobe injuries and substance use disorders.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders; as well as to compounds of the invention of the formula I or of an N-oxide, a stereoisomer or of pharmaceutically acceptable salts thereof for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders; as well as to compounds of the invention of the formula I or of an N-oxide, a stereoisomer or of pharmaceutically acceptable salts thereof for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders; as well as to compounds of the invention of the formula I or of an N-oxide, a stereoisomer or of pharmaceutically acceptable salts thereof for the treatment and/or prophylaxis of depressive disorders. In the case of depressive disorders, specific mention is to be made of childhood onset mood disorders, i.e. depressive moods having their onset in childhood, but also of major depression, seasonal depression, bipolar and related disorders, dysthymic disorders, disruptive mood dysregulation disorder, premenstrual dysphoric disorder, substance/medication-induced depressive disorder, and depressive disorder due to another medical condition, and especially of major depression and seasonal depression as well as of the depressive phases of bipolar disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors; as well as to compounds of the invention of the formula I or of an N-oxide, a stereoisomer or of pharmaceutically acceptable salts thereof for the treatment and/or prophylaxis of the above-listed diseases. To be more precise, the present invention relates to the use of compounds of the invention of the formula I or of an N-oxide, a stereoisomer or pharmaceutically acceptable salts thereof for the manufacture of a medicament for the treatment and/or prophylaxis of substance-related and addictive disorders such as substance use disorder, substance-induced disorder, alcohol use disorder, alcohol intoxication, alcohol withdrawal, unspecified alcohol-related disorder, caffeine intoxication, caffeine withdrawal, unspecified caffeine disorder, *cannabis* use disorder, *cannabis* withdrawal, unspecified *cannabis*-related disorder, phencyclidine use disorder, other hallucinogen use disorders, phencyclidine intoxication, other hallucinogen disorders, hallucinogen persisting perception disorder, unspecified phencyclidine disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, unspecified tobacco-related disorder, other (or unknown) substance use disorders, other (or unknown) substance intoxication, other (or unknown) substance withdrawal, other (or unknown) substance related disorder and gambling disorder; as well as to compounds of the invention of the formula I or of an N-oxide, a stereoisomer or of pharmaceutically acceptable salts thereof for the treatment and/or prophylaxis of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis; as well as to compounds of the invention of the formula I or of an N-oxide, a stereoisomer or of pharmaceutically acceptable salts thereof for the treatment and/or prophylaxis of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain; as well as to compounds of the invention of the formula I or of an N-oxide, a stereoisomer or of pharmaceutically acceptable salts thereof for the treatment and/or prophylaxis of the above-listed disorders. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient in need thereof.

Concerning the definition of vasopressin-related diseases, reference is made to the above statements made in context with the use according to the invention. Thus, preferred embodiments of the method of the invention correspond to preferred embodiments of the use according to the invention.

The patient to be treated prophylactically or therapeutically with the method of the invention is preferably a mammal, for example a human or a nonhuman mammal or a nonhuman transgenic mammal Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, stereoisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis schemes 1 to 4, are explained in greater detail merely by way of example using the given examples without being exclusively restricted to synthesis routes 1 to 4 or analogous methods.

EXPERIMENTAL SECTION

| Abbreviations used: | |
|---|---|
| rt | room temperature (20-25° C.) |
| h | hour(s) |
| min | minute(s) |
| d | day(s) |
| quant. | quantitative |
| eq. | equivalent(s) |
| conc. | concentrated |
| TLC | thin layer chromatography |
| RP | reversed phase |
| aq. | aqueous |
| sat. | saturated |
| ACN | acetonitrile |
| DCM | dichloromethane |
| DIPEA | diisopropylethyl amine |
| DMF | dimethylformamide |
| DMSO | dimethyl sulfoxide |
| EA or EtOAc | ethyl acetate |
| Et$_3$N | triethyl amine |
| EtOH | ethanol |
| MeOH | methanol |
| MeOD | deuteromethanol |
| OAc | acetate |
| PE | petrol ether |
| Pd(PPh$_3$)$_4$ | tetrakis(triphenyl-phosphine)palladium(0) |
| TBAF | tetrabutylammonium fluoride |
| TFA | trifluoroacetic acid |
| THF | tetrahydrofuran |
| p: | pseudo (for example pt pseudo triplet) |
| b: | broad (for example bs broad singlet) |
| s: | singlet |
| d: | doublet |
| t: | triplet |
| m: | multiplet |
| dd: | doublet of doublets |
| dt: | doublet of triplets |
| tt: | triplet of triplets |

LC-MS was recorded on Agilent 1200 HPLC/6110 SQ system by the following conditions:
Method A:
Mobile Phase: A: Water (0.05% TFA) B: ACN (0.05% TFA)
Gradient: 5% B for 0.1 min, increase to 95% B within 0.7 min, 95% B for 0.9 min, back to 5% B within 0.01 min.
Flow Rate: 3.0 mL/min
Column: Zorbax SB-C18 Rapid Resolution HT, 4.6*30 mm, 1.8 μm
Column Temperature: 45° C.
Method B:
Mobile Phase: A: Water (10 mM NH$_4$HCO$_3$) B: ACN
Gradient: 5% B for 0.2 min, increase to 95% B within 1.2 min, 95% B for 1.6 min, back to 5% B within 0.01 min.
Flow Rate: 1.8 mL/min
Column: XBridge C18, 4.6*50 mm, 3.5 μm
ColumnTemperature: 50° C.
Method C:
Mobile Phase: A: Water (10 mM NH$_4$HCO$_3$) B: ACN
Gradient: 5% for 0.2 min, increase to 95% B within 1.7 min, 95% B for 1.4 min, back to 5% B within 0.01 min
Flow Rate: 2.1 mL/min
Column: XBridge C18, 4.6*50 mm, 3.5 μm
Column Temperature: 50° C.

Method D:
Mobile Phase: A: Water (0.01% TFA) B: ACN (0.01% TFA)
Gradient: 5% B increase to 95% B within 1.2 min, 95% B for 1.3 min, back to 5% B within 0.01 min
Flow Rate: 2.0 mL/min
Column: XBridge C18, 4.6*50 mm, 3.5 μm
Column Temperature: 50° C.
Method E:
Mobile Phase: A: Water (10 mM NH$_4$HCO$_3$) B: ACN
Gradient: 5% B increase to 95% B within 1.3 min, 95% B for 1.5 min, back to 5% B within 0.01 min.
Flow Rate: 1.8 mL/min
Column: XBridge C18, 4.6*50 mm, 3.5 μm
ColumnTemperature: 50° C.
Method F:
Mobile phase: A: Water (0.01% TFA) B: ACN (0.01% TFA)
Gradient was 5% B for 0.2 min, and to 95% B within 1.7 min then with a hold at 95% B for 1.3 min, back to 5% B within 0.01 min.
Flow Rate: 2.3 mL/min.
Column: XBridge C18, 4.6*50 mm, 3.5 μm
Method G:
Mobile phase: A: Water (10 mM NH$_4$HCO$_3$) B: ACN
Gradient was 5% B for 0.2 min, and to 95% B within 1.7 min then with a hold at 95% B for 1.3 min, back to 5% B within 0.01 min.
Flow Rate: 2.3 mL/min.
Column: XBridge C18, 4.6*50 mm, 3.5 μm.
Method H:
Mobile Phase: A: Water (0.01% TFA), B: ACN (0.01% TFA)
Gradient: 5% B for increase to 100% B within 1.2 min, 95% B for 1.3 min, back to 5% B within 0.01 min.
Flow Rate: 2.0 mL/min.
Column: SunFire C18, 4.6*50 mm, 3.5 μm
Column Temperature: 50° C.
Method I:
Mobile Phase: A: Water (0.01% TFA), B: ACN (0.01% TFA)
Gradient: 5% B for increase to 100% B within 0.8 min, 100% B for 0.9 min,
Flow Rate: 2.0 mL/min.
Column: ZORBAX SB-C18, 4.6*50 mm,
Column Temperature: 50° C.
Method K:
Mobile Phase: A: Water (0.05% TFA), B: ACN (0.05% TFA).
Gradient: 5% B for 0.1 min, and to 95% B within 0.7 min then with a hold at 95% B for 0.9 min, back to 5% B within 0.01 min
Flow Rate: 3.0 mL/min
Column: 4.6×30 mm Zorbax SB-C18 Rapid Resolution HT column (1.8 μm particles).

All mass spectra were taken under electrospray ionisation (ESI) methods.

I. Preparation of Compounds of Formula I

Example 1

2-(2-(3-Chlorophenyl)-4-oxo-6-(3-(piperidin-1-ylm-ethyl)cyclobut-1-en-1-yl)quinazolin-3(4H)-yl)-N-isopropylacetamide (Example 1: compound of formula I.24, wherein Q is Q.14, Y is CH, $R^{5a}$ is H, $R^{5b}$ is H and $R^{5c}$ is Cl)

1.1 2-Amino-5-bromo-N-[2-(isopropylamino)-2-oxoethyl]benzamide

A mixture of 2-(3H-[1,2,3]triazolo[4,5-b]pyridin-3-yl)-1,1,3,3-tetramethylisouronium hexafluorophosphate(V) (6.34 g, 16.66 mmol), 2-amino-N-isopropylacetamide (1.936 g, 16.66 mmol), DIPEA (3.64 mL, 20.83 mmol) and 2-amino-5-bromobenzoic acid (3.0 g, 13.89 mmol) in DCM (80 mL) was stirred at rt for about 4 h. The reaction mixture was washed with water. The organic layer was dried with $MgSO_4$, filtered, concentrated, and used in the next step directly without further purification.

LC-MS (Method C): m/z 314 [M+H]$^+$, RT: 1.613 min.

1.2 5-Bromo-2-(3-chlorobenzamido)-N-[2-(isopropylamino)-2-oxoethyl]benzamide A mixture of 2-amino-5-bromo-N-[2-(isopropylamino)-2-oxoethyl]benzamide (4.2 g, 13.41 mmol) and triethylamine (2.71 g, 26.8 mmol) in THF (120 mL) was stirred at 0° C. for 15 min. 3-Chlorobenzoyl chloride (3.52 g, 20.12 mmol) was added slowly. The reaction mixture was then warmed up to rt and stirring was continued for about 3 h. The reaction mixture was filtered, concentrated to dryness and the residue was recrystallized from MeOH to give white solid (6.0 g, yield: 94%).

LC-MS (Method B): m/z 452 [M+H]$^+$, RT: 1.874 min.

1.3 2-(6-Bromo-2-(3-chlorophenyl)-4-oxoquinazolin-3(4H)-yl)-N-isopropylacetamide Sodium hydroxide (0.265 g, 6.63 mmol) was added to 5-bromo-2-(3-chlorobenzamido)-N-(2-(isopropylamino)-2-oxoethyl)benzamide (1.0 g, 2.209 mmol) in MeOH (20 mL), and the mixture was stirred at 80° C. for 8 h. The mixture was then cooled and filtered. The title compound was collected as solid (0.46 g, yield: 47.9%).

LC-MS (Method B): m/z 434 [M+H]$^+$, RT: 1.845 min.

1.4 2-[2-(3-Chlorophenyl)-4-oxo-6-(4,4,5,5-tetramethyl-1,3,2-dioxaborolan-2-yl]quinazolin-3(4H)-yl]-N-isopropylacetamide A mixture of [1,1'-bis(diphenylphosphino)ferrocene]dichloropalladium(II) (0.673 g, 0.920 mmol), 2-(6-bromo-2-(3-chlorophenyl)-4-oxoquinazolin-3(4H)-yl)-N-isopropylacetamide (8.0 g, 18.40 mmol), 4,4,4',4',5,5,5',5'-octamethyl-2,2'-bi(1,3,2-dioxaborolane) (9.35 g, 36.8 mmol) and potassium acetate (5.42 g, 55.2 mmol) in dioxane (150 mL) was heated at 80° C. over night reflux under nitrogen. Then, the reaction mixture was filtered, concentrated and purified by silica-gel chromatography (EA/PE=1/2) to give the title product (5.7 g, yield: 62%).

LC-MS (Method D): m/z 482 [M+H]$^+$, RT: 1.892 min.
$^1$H-NMR (DMSO-d6, 400 MHz): 8.51 (s, 1H), 8.07 (dd, J=1.2 Hz, 8.0 Hz, 1H), 7.99 (d, J=7.2 Hz, 1H), 7.70-7.55 (m, 5H), 4.44 (s, 2H), 3.83-3.75 (m, 1H), 1.34 (s, 12H), 1.00 (d, J=6.4 Hz, 6H).

1.5 3-(Hydroxymethyl)cyclobutanol

A solution of 3-oxocyclobutanecarboxylic acid (10 g, 88 mmol) in THF (500 mL) was cooled to about −78° C. in a dry ice/acetone bath. $BH_3 \cdot DMS$ (borane dimethyl sulfide complex) (131 mL, 263 mmol) was added dropwise via syringe to the reaction. The resulting solution was stirred at rt for about 16 h. After completion of the reaction, the reaction was cooled to about 0° C. in an ice bath, and MeOH was added to quench the reaction. The solvent was removed under reduced pressure to give white oil. Purification by chromatography onto a silica gel column (elution with 5% MeOH/$CH_2Cl_2$) gave 3-(hydroxymethyl)cyclobutanol (8.8 g, yield: 98%).

LC-MS (Method D): RT: 1.341 min

1.6 3-(((tert-Butyldiphenylsilyl)oxy)methyl)cyclobutanol

A mixture of 3-(hydroxymethyl)cyclobutanol (6.7 g, 65.6 mmol), 4-(dimethylamino)pyridine (0.801 g, 6.56 mmol) and $Et_3N$ (18.29 mL, 131 mmol) in DCM (180 mL) was stirred at about 0° C. Then, tert-butyldiphenylsilyl chloride (18.87 mL, 73.5 mmol) was added slowly to the reaction. The resulting reaction was stirred at about 0° C. for about 2 h. LC-MS indicated complete conversion to the title compound. The solvent was removed under reduced pressure and the resulting solid was deposited onto silica gel and loaded onto a silica gel column and eluted with 5:1 hexane/EtOAc to give the title compound (10 g, yield: 44.3%).

LC-MS (Method E): m/z 341 [M+H]$^+$, RT: 2.33 min

1.7 3-(((tert-Butyldiphenylsilyl)oxy)methyl)cyclobutanone

To a solution of 3-(((tert-butyldiphenylsilyl)oxy)methyl)cyclobutanol (10 g, 29.4 mmol) in DCM (200 mL) was added Dess-Martin-periodinane (14.95 g, 35.2 mmol) at rt. The reaction mixture was stirred for about 1 h, dried and purified by chromatography on silica-gel (PE/EA=50/1) to give the title compound (6.2 g, yield: 60%).

$^1$H-NMR (CDCl$_3$, 400 MHz): 7.66-7.64 (m, 4H), 7.43-7.39 (m, 6H), 3.80 (d, J=5.6 Hz, 2H), 3.10-3.02 (m, 2H), 3.98-3.90 (m, 2H), 2.64-2.57 (m, 1H), 1.06 (s, 9H).

1.8 3-(((tert-Butyldiphenylsilyl)oxy)methyl)cyclobut-1-en-1-yl trifluoromethanesulfonate To a solution of 3-(((tert-butyldiphenylsilyl)oxy)methyl)cyclobutanone (2.0 g, 5.91 mmol) in THF (25 mL) was added lithium bis(trimethylsilyl)amide (7.68 mL, 7.68 mmol) at −78° C. The mixture was stirred for about 3 h and then, a solution of 1,1,1-trifluoro-N-phenyl-N-((trifluoromethyl)sulfonyl)methanesulfonamide (2.216 g, 6.20 mmol) in THF (25 mL) was added. The cooling bath was removed 30 minutes after completed addition, and the reaction mixture was stirred for 12 h at rt. The mixture was quenched with tert-butyl methyl ether (50 mL) and washed with 1 M aqueous NaOH solution (3×). The organic layers were dried. Purification by TLC (PE/EA=100/1) gave the title compound (0.75 g, yield: 27%).

LC-MS (Method D): RT: 2.68 min.
$^1$H-NMR (CDCl$_3$, 400 MHz): 7.65-7.60 (m, 5H), 7.43-7.30 (m, 5H), 5.42 (s, 1H), 3.69 (d, J=6.0 Hz, 2H), 2.94 (dd, J=4.4 Hz, 13.6 Hz, 1H), 2.79-2.75 (m, 1H), 2.55 (d, J=13.6 Hz, 1H), 1.06 (s, 9H).

1.9 2-(6-(3-(((tert-butyldiphenylsilyl)oxy)methyl)cyclobut-1-en-1-yl)-2-(3-chlorophenyl)-4-oxo-quinazolin-3(4H)-yl)-N-isopropylacetamide A mixture of 3-(((tert-butyldiphenylsilyl)oxy)methyl)cyclobut-1-en-1-yl trifluoromethanesulfonate (1.003 g, 1.598 mmol), 2-[2-(3-chlorophenyl)-4-oxo-6-(4,4,5,5-tetramethyl-1,3,2-dioxaborolan-2-yl)quinazolin-3(4H)-yl]-N-isopropylacetamide (0.7 g, 1.453 mmol), $Na_2CO_3$ (0.385 g, 3.63 mmol) and Pd(PPh$_3$)$_4$ (0.084 g, 0.073 mmol) in toluene (35 mL) was stirred at 60° C. for 5 h. The reaction mixture was filtered through a pad of silica gel, and the solvent was removed under reduced pressure. The sample was deposited onto silica gel and loaded onto a silica gel column and eluted with 1:4 EtOAc/heptane to give the title compound (0.57 g, yield: 53.4%).

LC-MS (Method D): m/z 676 [M+H]+, RT: 2.46 min.
$^1$H-NMR (CDCl$_3$, 400 MHz): 8.19 (s, 1H), 7.81-7.26 (m, 16H), 6.45 (s, 1H), 5.67 (d, J=6.4 Hz, 1H), 4.49 (s, 2H), 4.1 (m, 1H), 3.82 (d, J=4.8 Hz, 1H), 3.07 (m, 1H), 2.93 (m, 1H), 2.50 (d, J=4.8 Hz, 1H), 1.17 (d, J=6.4 Hz, 6H), 1.06 (s, 9H).

1.10 2-[2-(3-Chlorophenyl)-6-(3-(hydroxymethyl)cyclobut-1-en-1-yl)-4-oxo-quinazolin-3(4H)-yl]-N-isopropylacetamide TBAF in THF (8.13 mL, 8.13 mmol) was dissolved in THF (30 mL), stirred and cooled to about −78° C. for about 20 min under nitrogen. Then, 2-[6-(3-(((tert-butyldiphenylsilyl)oxy)methyl)cyclobut-1-en-1-yl)-2-(3-chlorophenyl)-4-oxo-quinazolin-3(4H)-yl]-N-isopropylacetamide (1.1 g, 1.626 mmol) in THF (30 mL) was added dropwise. The cooling-bath was removed and the mixture stirred at rt for 3 h. The reaction mixture was concentrated, water was added and the mixture was extracted with DCM for 3 times. Purification of the organic layers by chromatography on silica-gel (DCM/MeOH=30/1) gave the title compound (0.38 g, yield: 50%).

LC-MS (Method D): m/z 438 [M+H]+, RT: 1.59 min.

1.11 [3-(2-(3-Chlorophenyl)-3-(2-(isopropylamino)-2-oxoethyl)-4-oxo-3,4-dihydroquinazolin-6-yl)cyclobut-2-en-1-yl]methyl methanesulfonate Methanesulfonyl chloride (145 mg, 1.267 mmol) was added dropwise into the mixture of triethylamine (0.347 mL, 2.53 mmol) and 2-[2-(3-chlorophenyl)-6-(3-(hydroxymethyl)cyclobut-1-en-1-yl)-4-oxo-quinazolin-3(4H)-yl]-N-isopropylacetamide (370 mg, 0.845 mmol) in DCM (100 mL) at 0° C. Then, the reaction mixture was stirred at rt for about 4 h. TLC indicated that the reaction was complete. The reaction mixture was diluted with sat. NaCl solution. The aqueous layer was extracted with methylene chloride (3×5 mL). The combined organic layers were dried over Na$_2$SO$_4$, filtered through a pad of celite and concentrated to give the yellow title compound (0.39 g, yield: 83%). This material was used directly without further purification.

LC-MS (Method D): m/z 516 [M+H]+, RT: 1.845 min.

1.12 2-[2-(3-Chlorophenyl)-4-oxo-6-(3-(piperidin-1-ylmethyl)cyclobut-1-en-1-yl)quinazolin-3(4H)-yl]-N-isopropylacetamide Under nitrogen, to a solution of [3-(2-(3-chlorophenyl)-3-(2-(isopropylamino)-2-oxoethyl)-4-oxo-3,4-dihydroquinazolin-6-yl)cyclobut-2-en-1-yl]methyl methanesulfonate (115 mg, 0.223 mmol) and piperidine (0.066 mL, 0.669 mmol) in acetonitrile (12 mL), K$_2$CO$_3$ (154 mg, 1.114 mmol) was added in one portion. The reaction was heated in a Biotage microwave at 80° C. for 6 h in microwave reactor. The reaction was monitored by LC-MS. After the reaction was completed, the reaction mixture was diluted with sat. NaCl solution. The reaction was extracted with DCM (3×20 mL). The combined organic layers were dried over Na$_2$SO$_4$, filtered through a Büchner funnel and concentrated to give the title compound as a yellow solid.

LC-MS (Method D): m/z 505 [M+H]+, RT: 1.972 min.

$^1$H-NMR (CDCl$_3$, 400 MHz): 8.17 (s, 1H), 7.82-7.45 (m, 7H), 6.51 (s, 1H), 5.60 (d, J=12.4 Hz, 1H), 4.49 (s, 2H), 4.12-4.08 (m, 1H), 3.12-3.02 (m, 2H), 2.64-2.47 (m, 6H), 1.47-1.26 (m, 6H), 1.17 (d, J=6.8 Hz, 6H).

Example 2 cis-2-[2-(3-chlorophenyl)-4-oxo-6-[3-(1-piperidylmethyl)cyclobutyl]quinazolin-3-yl]-N-isopropyl-acetamide (example 2a) and trans-2-[2-(3-chlorophenyl)-4-oxo-6-[3-(1-piperidylmethyl)cyclobutyl]quinazolin-3-yl]-N-isopropyl-acetamide (example 2b)

(Example 2a: compound of formula I.4, wherein Q is Q.14, Y is CH, R$^{5a}$ is H, R$^{5b}$ is H and R$^{5c}$ is Cl and where the substituents on the 1,3-cyclobutandiyl radical adopt the cisconfiguration)
(Example 2b: compound of formula I.4, wherein Q is Q.14, Y is CH, R$^{5a}$ is H, R$^{5b}$ is H and R$^{5c}$ is Cl and where the substituents on the 1,3-cyclobutandiyl radical adopt the trans-configuration)

A mixture of 2-[2-(3-chlorophenyl)-4-oxo-6-(3-(piperidin-1-ylmethyl)cyclobut-1-en-1-yl)quinazolin-3(4H)-yl]-N-isopropylacetamide (600 mg, 1.188 mmol) and Pt/C (150 mg, 10%) in MeOH (10 mL) was stirred at rt under hydrogen overnight. The reaction mixture was filtered and purified by chiral-HPLC to give 102 mg of the compound of example 2a and 25 mg of the compound of example 2b.

Conditions:
Instrument: Waters2767 (PHW-002)
Column: XBridge Prep C18 OBD, 30*100 mm, 5 μm
Mobile Phase A: Water (0.1% NH$_3$H$_2$O); B: ACN
Gradient 45-75% B in 9 min, stop at 12.7 min
Flow Rate 30.00 mL/min
Detective Wavelength 214/254 nm
Retention Time 6.5 min

Example 2a

LC-MS (Method E): m/z 507 [M+H]+, RT: 1.848 min.
$^1$H-NMR (DMSO-d6, 400 MHz): 8.11 (s, 1H), 7.69-7.41 (m, 6H), 5.59 (d, J=7.6 Hz, 1H), 4.48 (s, 2H), 4.12-4.04 (m, 1H), 3.57-3.49 (m, 1H), 2.64-2.59 (m, 3H), 2.46-2.39 (m, 6H), 1.87 (d, J=8.4 Hz, 2H), 1.61-1.45 (m, 4H), 1.44-1.40 (m, 2H), 1.17 (d, J=6.4 Hz, 6H).

Example 2b

LC-MS (Method E): m/z 507 [M+H]+, RT: 1.875 min
$^1$H-NMR (DMSO-d6, 400 MHz): 8.20 (s, 1H), 7.71-7.41 (m, 6H), 5.61 (d, J=7.6 Hz, 1H), 4.49 (s, 2H), 4.14-4.06 (m, 1H), 3.73-3.68 (m, 1H), 2.69-2.59 (m, 3H), 2.47-2.30 (m, 6H), 2.30-2.24 (m, 2H), 1.64-1.55 (m, 4H), 1.49-1.42 (m, 2H), 1.17 (d, J=6.4 Hz, 6H).

Example 3

2-[2-(3-Chlorophenyl)-4-oxo-6-[2-[2-(1-piperidyl)ethyl]cyclopropyl]quinazolin-3-yl]-N-isopropyl-acetamide (Example 3: compound of the formula I.44, wherein Q is Q.14, Y is CH, R$^{5a}$ is H, R$^{5b}$ is H and R$^{5c}$ is Cl)

3.1 Methyl 2-[[2-[(3-chlorobenzoyl)amino]-5-iodobenzoyl]amino]acetate

To a solution of methyl 2-[(2-amino-5-iodo-benzoyl)amino]acetate (20 g, 59.9 mmol) in 400 mL of THF was added triethylamine (16.69 mL, 120 mmol) and 3-chlorobenzoyl chloride (11.00 g, 62.9 mmol) dropwise at 0° C. The reaction mixture was stirred at 0° C. for 2 h. Solvent was evaporated and water was added to the residue. The mixture was extracted with EtOAc. The organic layer was washed with brine, dried over $Na_2SO_4$, filtered and concentrated to give the title compound (25.5 g, 53.9 mmol, 90% yield). LCMS (Method K): m/z 473.0 $[M+H]^+$, RT: 2.03 min.

3.2 2-[[2-[(3-Chlorobenzoyl)amino]-5-iodo-benzoyl]amino]acetic acid

To a solution of compound 3.1 (39 g, 83 mmol) in 600 mL of methanol was added 2M NaOH (250 mL). The mixture was stirred at rt for 3 h. Solvent was evaporated. 1N HCl was added to adjust the reaction mixture to pH=7. The precipitate was collected and dried to give the title compound (33 g, 72.0 mmol, 87% yield).
LCMS (Method G): m/z 459.0 $[M+H]^+$, RT: 1.49 min.

3.3 2-[(3-Chlorobenzoyl)amino]-5-iodo-N-[2-(isopropylamino)-2-oxo-ethyl]benzamide To a solution of compound 3.2 (22 g, 48.0 mmol) in 800 mL of DCM is added 1-[bis(dimethylamino)methylene]-1H-1,2,3-triazolo[4,5-b]pyridinium 3-oxid hexafluorophosphate (HATU, 18.97 g, 49.9 mmol) and DIPEA (12.57 mL, 72.0 mmol) at 0° C. followed by addition of propan-2-amine (4.93 ml, 57.6 mmol) dropwise. The reaction mixture was stirred at rt for 4 h. Water was added to quench the reaction. The precipitate was collected to give the title compound (21 g, 39.9 mmol, 83% yield) as a white solid.
LCMS (Method G): m/z 500 $[M+H]^+$, RT: 1.96 min

3.4 2-[2-(3-Chlorophenyl)-6-iodo-4-oxo-quinazolin-3-yl]-N-isopropyl-acetamide To a solution of compound 3.3 (25 g, 50.0 mmol) in 600 mL of DCM was added iodine (25.4 g, 100.0 mmol) and bis(trimethylsilyl)amine (41.9 mL, 200 mmol) dropwise via syringe. The reaction mixture was stirred at 40° C. for 5 h. After cooling to rt, 5% $Na_2S_2O_3$ solution was added at ice bath. The organic layer was separated and dried over anhydrous sodium sulfate, filtered and concentrated to give the title compound (14 g, 29.1 mmol, 58.1% yield) as a brown solid.
LCMS (Method G): ESI-MS: m/z: 482.0 $[M+H]^+$; RT=2.00 min.

3.5 2-[2-(3-Chlorophenyl)-6-[4-hydroxybut-1-enyl]-4-oxo-quinazolin-3-yl]-N-isopropyl-acetamide To a mixture of 2-[2-(3-chlorophenyl)-6-iodo-4-oxo-quinazolin-3-yl]-N-isopropylacetamide (3.8 g, 7.9 mmol), but-3-en-1-ol (0.86 g, 12 mmol) and triethylamine (2.02 g, 20 mmol) were added $Pd(OAc)_2$ (0.19 g, 0.8 mmol) and triphenylphosphine (0.62 g, 2.4 mmol) in $CH_3CN$ (30 mL). The mixture was stirred for 18 h at rt. After adding water (100 mL), the mixture was extracted with EtOAc (50 mL×3=150 mL), dried over $Na_2SO_4$, filtered and concentrated. The residue was purified by a silica gel column chromatography (eluting with: DCM:MeOH=40:1) to give the title compound (2.2 g, 5.2 mmol, 65% yield) as a pale yellow solid.
LC-MS (Method F).: m/z: 426.0 $[M+H]^+$; RT=1.80 min

3.6 2-[2-(3-Chlorophenyl)-6-formyl-4-oxo-quinazolin-3-yl]-N-isopropyl-acetamide To a solution of 2-[2-(3-chlorophenyl)-6-[4-hydroxybut-1-enyl]-4-oxo-quinazolin-3-yl]-N-isopropyl-acetamide (2.0 g, 4.8 mmol) and $NaIO_4$ (2.1 g, 9.6 mmol) in $THF/H_2O=2:1$ (150 mL) was added $OsO_4$ (100 mg, 0.39 mmol). The mixture was stirred for 18 h at rt. Then, water (100 mL) was added to the solution and the mixture was extracted with EtOAc (50 mL*3), dried over $Na_2SO_4$, filtered and concentrated. The residue was purified by a silica gel column chromatography (eluting with: DCM:MeOH=30:1) to give the title compound (2.1 g, 5.5 mmol, 80% yield) as a pale yellow solid.
LC-MS (Method G): m/z: 384.0 $[M+H]^+$; RT=1.13 min

3.7 2-[2-(3-Chlorophenyl)-4-oxo-6-[(p-tolylsulfonylhydrazono)methyl]quinazolin-3-yl]-N-isopropyl-acetamide To a solution of the compound of example 3.6 (1.73 g, 4.5 mmol) and 4-methylbenzenesulfonohydrazide (0.84 g, 4.5 mmol) in dioxane (10 mL) was added $K_2CO_3$ (0.94 g, 6.7 mmol). The mixture was stirred for 1 h at 70° C. in a microwave reactor. After water (100 mL) was added to the solution, the mixture was extracted with EtOAc (50 mL*3), dried over $Na_2SO_4$, filtered and concentrated. The residue was purified by a silica gel column chromatography (eluting with: DCM:MeOH=30:1) to give the title compound (2 g, 3.6 mmol, 80% yield) as a pale yellow solid.
LC-MS (Method G): m/z: 552.0 $[M+H]^+$; RT=1.20 min

3.8 [2-[2-[2-(3-Chlorophenyl)-3-[2-(isopropylamino)-2-oxo-ethyl]-4-oxo-quinazolin-6-yl]cyclopropyl]vinyl]acetate To a solution of buta-1,3-dienyl acetate (0.62 g, 3.9 mmol) and $K_2CO_3$ (0.16 g, 1.17 mmol) in dioxane (20 mL) was added slowly the compound of example 3.7 (0.431 g, 0.78 mmol) for 6 h. The mixture was allowed to stop at once. After water (100 mL) was added to the solution, the mixture was extracted with EtOAc (50 mL*3), dried over $Na_2SO_4$, filtered and concentrated. The residue was purified by a silica gel column chromatography (eluting with: DCM:MeOH=20:1) to give the title compound (7.5 mg, 0.015 mmol, 2% yield) as a pale yellow solid.
LC-MS (Method F): m/z: 480.0 $[M+H]^+$; RT=1.78 min

3.9 2-[2-(3-Chlorophenyl)-4-oxo-6-[2-(2-oxoethyl)cyclopropyl]quinazolin-3-yl]-N-isopropyl-acetamide To a solution of the compound of example 3.8 (7.3 mg, 0.015 mmol) in MeOH (2 mL) was added LiOH (1.45 mg, 0.061 mmol). The mixture was stirred for 1 h at rt. After water (2 mL) was added to the solution, the mixture was extracted with EtOAc (10 mL*3), dried over $Na_2SO_4$, filtered and concentrated to give the crude title compound (6 mg, 0.013 mmol, 90% yield) as a pale yellow solid, which was used in the next step without purification.
LC-MS (Method F): m/z: 438.0 $[M+H]^+$; RT=1.14 min.

3.10 2-[2-(3-Chlorophenyl)-4-oxo-6-[2-[2-(1-piperidyl)ethyl]cyclopropyl]quinazolin-3-yl]-N-isopropyl-acetamide To a solution of the compound of example 3.9 (5 mg, 0.011 mmol) and piperidine (1.02 mg, 0.012 mmol), acetic acid (catalytic amount) in 1,2-dichloroethane (2 mL) and $NaBH(OAc)_3$ (3.5 mg, 0.0165 mmol) were added. The mixture was stirred for 16 h at rt and then concentrated to the crude product. The residue was purified by prep-HPLC to give the title compound (3.5 mg, 0.0069 mmol, 60% yield) as a pale white solid.
Conditions for prep-HPLC:
Instrument: waters 2767 (PHW-004)
Column: XBridge Prep C18 OBD, 19*250 mm, 10 μm
Mobile Phase A: water (10 mmol/ml $NH_4HCO_3$); B: ACN
Gradient: 50-80% B in 9.0 min, stop at 12.7 min
Flow Rate: 30.00 mL/min
Detective Wavelength (nm): 214\254
RT: 7.38 min
LC-MS (Method F): m/z: 507.0 [M+H]$^+$; RT=1.47 min.
$^1$H NMR: (400 MHz, MeOD): δ 8.05-8.03 (m, 1H), 7.94-7.80 (m, 1H), 7.69-7.52 (m, 5H), 4.57 (s, 2H), 3.93-3.87 (m, 1H), 3.57-3.53 (m, 1H), 3.29-3.23 (m, 2H), 2.94-2.45 (m, 2H), 1.99-1.12 (m, 12H), 1.10 (d, J=6.4 Hz, 6H), 0.92-0.89 (m, 2H).

Example 4

2-[2-(3-Chlorophenyl)-4-oxo-6-[2-(1-piperidylmethyl)cyclopropyl]quinazolin-3-yl]-N-isopropyl-acetamide (Example 4: compound of the formula I.34, wherein Q is Q.14, Y is CH, $R^{5a}$ is H, $R^{5b}$ is H and $R^{5c}$ is Cl)

4.1 Ethyl 2-[2-(3-chlorophenyl)-3-[2-(isopropylamino)-2-oxo-ethyl]-4-oxo-quinazolin-6-yl]cyclopropanecarboxylate To a solution of the compound of example 3.7 (0.2 g, 0.36 mmol) and ethyl acrylate (0.15 g, 1.45 mmol) in dioxane (10 mL) was added $K_2CO_3$ (0.075 g, 0.54 mmol). The mixture was stirred for 1 h at 150° C. in a microwave reactor. After water (100 mL) was added to the solution, the mixture was extracted with EtOAc (50 mL*3=150 mL), dried over $Na_2SO_4$, filtered and concentrated. The residue was purified by prep-TLC (eluting with DCM:MeOH=20:1) to give the title compound (34 mg, 0.072 mmol, 20% yield) as a pale yellow solid.
LC-MS (Method H): m/z: 468.0 [M+H]$^+$; RT=1.71 min 4.2 2-[2-(3-Chlorophenyl)-6-[2-(hydroxymethyl)cyclopropyl]-4-oxo-quinazolin-3-yl]-N-isopropyl-acetamide To a solution of the compound of example 4.1 (33 mg, 0.069 mmol) in DCM (10 mL) was added diisobutylaluminium hydride (1.38 mL, 1.38 mmol) at −78° C. under $N_2$ atmosphere. The mixture was stirred at −78° C. for 3 h. After water (100 mL) was added to the solution, the mixture was extracted with EtOAc (50 mL*3), dried over $Na_2SO_4$, filtered and concentrated. The residue was purified by prep-TLC (eluting with: DCM: MeOH=40:1) to give the title compound (25 mg, 0.058 mmol, 85% yield) as a pale yellow solid.
LC-MS (Method I): m/z: 426.0 [M+H]$^+$; RT=1.54 min.

4.3 2-[2-(3-Chlorophenyl)-6-(2-formylcyclopropyl)-4-oxo-quinazolin-3-yl]-N-isopropyl-acetamide To a solution of compound of example 4.2 (25 mg, 0.058 mmol) in DCM (10 mL) was added Dess-Martin Periodinane (29.7 mg, 0.07 mmol). The mixture was stirred for 3 h at rt. Then, sat. aqueous $Na_2S_2O_3$ solution with $NaHCO_3$ (10 mL) was added to the solution. The mixture was extracted with EtOAc (10 mL*3), dried over $Na_2SO_4$, filtered and concentrated to give the crude title compound (21 mg, 0.049 mmol, 85% yield) as a pale yellow solid.
LC-MS (Method I): m/z: 424.0 [M+H]$^+$, RT=1.61 min.

4.4 2-[2-(3-Chlorophenyl)-4-oxo-6-[2-(1-piperidylmethyl)cyclopropyl]quinazolin-3-yl]-N-isopropyl-acetamide To a solution of compound of example 4.3 (20 mg, 0.047 mmol) and piperidine (4.2 mg, 0.052 mmol), acetic acid (catalytic amount) in 1,2-dichloroethane (4 mL) and $NaBH(OAc)_3$ (15 mg, 0.07 mmol) were added. The mixture was stirred for 16 h at rt. Then, the mixture was concentrated and the residue was purified by prep-HPLC to give the title compound (14.0 mg, 0.028 mmol, 60% yield) as a pale white solid. LC-MS (Method I): m/z: 493.0 [M+H]$^+$; RT=1.42 min
$^1$H NMR: (400 MHz, MeOD): 8.11-8.03 (m, 1H), 7.88-7.73 (m, 1H), 7.71-7.54 (m, 5H), 4.60 (s, 2H), 3.95-3.91 (m, 1H), 3.66-3.63 (m, 2H), 3.32-3.24 (m, 2H), 3.04-2.67 (m, 3H), 2.30-2.24 (m, 1H), 1.98-1.27 (m, 9H), 1.13 (d, J=6.4 Hz, 6H).

Example 5

Cis-methyl 2-[2-(3-chlorophenyl)-4-oxo-6-[3-(1-piperidylmethyl)cyclobutyl]quinazolin-3-yl]acetate (Example 5: compound of the formula I, wherein $X^1$=N, $X^2$=N, $X^3$=CH, $X^4$=CH, $X^5$=CH, $R^1$=$CH_2COOCH_3$, $R^2$=3-chlorophenyl and $R^3$ is 3-(1-piperidylmethyl)cyclobutyl and where the substituents on the 1,3-cyclobutandiyl radical adopt the cis configuration)

5.1 Methyl 2-(6-(3-(((tert-butyldiphenylsilyl)oxy)methyl)cyclobut-1-en-1-yl)-2-(3-chlorophenyl)-4-oxoquinazolin-3(4H)-yl)acetate A mixture of 3-(((tert-butyldiphenylsilyl)oxy)methyl)cyclobut-1-en-1-yl trifluoromethanesulfonate (4.88 g, 7.26 mmol) from example 1.8, methyl 2-(2-(3-chlorophenyl)-4-oxo-6-(4,4,5,5-tetramethyl-1,3,2-dioxaborolan-2-yl)quinazolin-3(4H)yl)acetate (3 g, 6.60 mmol) (prepared in analogy to the method described for the preparation of the compound of example 1.4 but starting from ethyl aminoacetate,), $Na_2CO_3$ (1.748 g, 16.49 mmol) and $Pd(PPh_3)_4$ (0.381 g, 0.330 mmol) in toluene/water (ratio: 4:1, (150 mL) was stirred at 60° C. for 24 h. The reaction mixture was filtered through a pad of silica gel, remove solvent under reduced pressure. The sample was deposited onto silica gel and loaded onto a silica gel column and eluted with 1/10 EtOAc/Heptane. The fractions were collected to give the title compound (1.5 g, yield: 32%). LC-MS (Method D): m/z [M+H]$^+$: 649, RT: 2.455 min.

5.2 cis-Methyl 2-(6-(3-(((tert-butyldiphenylsilyl)oxy)methyl)cyclobutyl)-2-(3-chlorophenyl)-4-oxo-quinazolin-3(4H)-yl)acetate A mixture of methyl 2-(6-(3-(((tert-butyldiphenylsilyl)oxy)methyl)cyclobut-1-en-1-yl)-2-(3-chlorophenyl)-4-oxo-quinazolin-3(4H)-yl)acetate (1.4 g, 2.156 mmol) and dihydroxypalladium (700 mg, 4.98 mmol) in 120 mL of MeOH was stirred at room temperature for 100 min under the atmosphere of hydrogen to give the title compound (0.5 g, yield: 35.2%) as the main product.
LCMS (Method D): m/z [M+H]$^+$: 651, RT: 2.63 min.

¹H-NMR (DMSO-d6, 400 MHz): 7.97 (s, 1H), 7.76-7.17 (m, 17H), 4.66 (m, 2H), 3.66 (m, 5H), 3.54-3.49 (m, 1H), 3.17 (s, 1H), 2.44-2.37 (m, 2H), 2.00-1.99 (m, 2H), 1.01 (s, 9H).

5.3 Cis-Methyl 2-[2-(3-chlorophenyl)-6-[3-(hydroxymethyl)cyclobutyl]-4-oxo-quinazolin-3-yl]acetate TBAF in THF (1.520 mL, 1.520 mmol) was dissolved in 15 mL of THF and then the compound of example 5.2 in 15 mL of THF was added dropwise at 0° C. under stirring. The cooling-bath was removed and the reaction mixture was stirred at rt for 2 h. The reaction mixture was concentrated and then EA was added. The reaction mixture was washed with sat. NaCl for 3 times. The organic layers were purified by chromatography on silica-gel (DCM/MeOH=30/1) to give the title compound (0.26 g, yield: 83%). LCMS (Method D): m/z [M+H]⁺: 413, RT: 1.677 min.

¹H-NMR (CDCl₃, 400 MHz): 8.06 (s, 1H), 7.62-7.60 (m, 2H), 7.37-7.35 (m, 4H), 4.57 (m, 2H), 3.70 (m, 3H), 3.58-3.49 (m, 3H), 2.50-2.49 (m, 3H), 1.92-1.90 (m, 2H).

5.4 Cis-methyl 2-[2-(3-chlorophenyl)-6-[3-(methylsulfonyloxymethyl)cyclobutyl]-4-oxo-quinazolin-3-yl]acetate Methanesulfonyl chloride (229 mg, 1.998 mmol) was added dropwise into the mixture of triethylamine (0.364 ml, 2.66 mmol) and the compound of example 5.3 in DCM (30 mL) at 0° C. The reaction mixture was stirred at rt for about 1 h. TLC indicated that the reaction was completely. The reaction mixture was diluted with sat. aq. NaCl solution. The aqueous layer was extracted with methylene chloride (3×20 mL). The combined organic layers were dried over Na₂SO₄, filtered through a pad of celite and concentrated to give a yellow solid which was used in the next step directly without further purification.

LCMS (Method D): m/z [M+H]⁺: 491, RT: 1.78 min.

5.5 Cis-Methyl 2-[2-(3-chlorophenyl)-4-oxo-6-[3-(1-piperidylmethyl)cyclobutyl]-quinazolin-3-yl]acetate A mixture of K₂CO₃ (507 mg, 3.67 mmol), the compound of example 5.4 (600 mg, 1.222 mmol) and piperidine (624 mg, 7.33 mmol) in ACN (15 mL) was heated in microwave oven at 80° C. for about 6 h. The mixture was extracted with ethyl acetate and water. The solution was concentrated to dryness to give the title compound (600 mg, 1.222 mmol) as a yellow solid.

LCMS (Method D): m/z [M+H]⁺: 480, RT: 1.47 min

Example 6 cis-2-(2-(3-Chlorophenyl)-4-oxo-6-(3-(piperidin-1-ylmethyl)cyclobutyl)quinazolin-3(4H)-yl)acetic acid (Example 6: compound of the formula I, wherein X¹=N, X²=N, X³=CH, X⁴=CH, X⁵=CH, R¹=CH₂COOH, R²=3-chlorophenyl and R³ is 3-(1-piperidylmethyl)cyclobutyl, and where the substituents on the 1,3-cyclobutandiyl radical adopt the cis configuration)

A mixture of the compound of example 5 (550 mg, 1.146 mmol) and lithium hydroxide (82 mg, 3.44 mmol) in 5 mL of MeOH and 2 ml of water was stirred at rt for 3 h. The solution was acidified with HCl (2 M). The solution was concentrated to dryness. The mixture was transferred in solution onto a silica gel column and eluted with 40% MeOH/CH₂Cl₂ and fractions were collected. The solution was concentrated to dryness to give the title compound.

LC-MS (Method D): m/z (M+H): 466, RT: 1.39 min.
¹H-NMR (MeOD, 400 MHz): 8.17 (s, 1H), 7.90-7.88 (m, 1H), 7.73-7.63 (m, 5H), 4.71 (m, 2H), 3.73 (m, 1H), 3.65-3.51 (m, 2H), 3.33 (m, 2H), 3.26 (m, 2H), 3.04-2.98 (m, 2H), 2.88-2.75 (m, 3H), 2.11-2.09 (m, 2H), 1.99-1.96 (m, 2H), 1.88-1.83 (m, 3H).

Example 7

Cis-2-[2-(3-Chlorophenyl)-6-[3-[(4-cyano-1-piperidyl)methyl]cyclobutyl]-4-oxo-quinazolin-3-yl]-N-isopropyl-acetamide (Example 7: compound of formula I.4, wherein Q is Q.21, Y is CH, R⁵ᵃ is H, R⁵ᵇ is H and R⁵ᶜ is Cl and where the substituents on the 1,3-cyclobutandiyl radical adopt the cis configuration)

7.1 Cis-2-[6-[3-[[tert-butyl(diphenyl)silyl]oxymethyl]cyclobutyl]-2-(3-chlorophenyl)-4-oxo-quinazolin-3-yl]-N-isopropyl-acetamide A mixture of compound of example 1.9 (1.7 g, 2.51 mmol), Pt/C (0.2 g) and H₂ (balloon) in MeOH was stirred for 8 h. The reaction mixture was filtered through a Büchner funnel and concentrated. The mixture was transferred neat onto a silica gel column and eluted with 5% MeOH/CH₂Cl₂. Fractions were collected and concentrated to give the title compound (0.5 g, 0.737 mmol, 29.3% yield).

LCMS (Method D): m/z 678 (M+H), RT: 2.45 min.
¹H-NMR (CDCl₃, 400 MHz): 8.07 (s, 1H), 7.68-7.38 (m, 17H), 5.60 (d, J=8.0 Hz, 1H), 4.49 (s, 1H), 4.09-4.05 (m, 1H), 3.64 (d, J=5.2 Hz, 2H), 3.56 (m, 1H), 2.58-2.42 (m, 3H), 2.06-2.03 (m, 2H), 1.15 (d, J=6.4 Hz, 6H), 1.06 (s, 9H).

7.2 Cis-2-[2-(3-chlorophenyl)-6-[3-(hydroxymethyl)cyclobutyl]-4-oxo-quinazolin-3-yl]-N-isopropyl-acetamide To a solution of compound of example 7.1 (0.6 g, 0.885 mmol) in THF (5 mL) was added TBAF (2.65 mL, 2.65 mmol) at 28° C. The reaction mixture was stirred for about 2 h and concentrated. The mixture was extracted with ethyl acetate and water. The combined organic layers were washed with brine, dried over Na₂SO₄, filtered, and concentrated under reduced pressure. The mixture was transferred in solution onto a silica gel column and eluted with 10% MeOH/CH₂Cl₂. Removal of the solvent under reduced pressure gave the title compound (0.3 g, 0.682 mmol, 77% yield) as a white solid. LCMS (Method D): m/z 440 [M+H]⁺, RT: 1.59 min.

¹H-NMR (DMSO-d₆, 400 MHz): 7.97 (s, 2H), 7.76-7.74 (m, 1H), 7.63-7.53 (m, 5H), 4.53 (m, 2H), 4.43 (s, 2H), 3.82-3.79 (m, 1H), 3.57-3.53 (m, 1H), 3.41-3.40 (m, 2H), 2.43-2.36 (m, 3H), 1.93-1.91 (m, 2H), 1.00 (d, J=6.4 Hz, 6H).

7.3 Cis-2-[2-(3-Chlorophenyl)-6-[3-[(4-cyano-1-piperidyl)methyl]cyclobutyl]-4-oxo-quinazolin-3-yl]-N-isopropyl-acetamide The title compound was prepared in two steps in analogy to steps 5.4 and 5.5 using 4-cyanopiperidine
ESI-MS: 535.20; [M]⁺=532.20; 266.60.

The compounds of examples 8 to 25 were prepared in an analogous manner as described in example 7.

Example 8 cis-2-[2-(3-Chlorophenyl)-4-oxo-6-[3-(thiomorpholinomethyl)cyclobutyl]quinazolin-3-yl]-N-isopropyl-acetamide (Example 8: compound of formula I.4, wherein Q is Q.33, Y is CH, $R^{5a}$ is H, $R^{5b}$ is H and $R^{5c}$ is Cl and where the substituents on the 1,3-cyclobutandiyl radical adopt the cis configuration)
ESI-MS: $[M+H]^+$=526.20; 525.20; 263.20

Example 9 cis-2-[2-(3-Chlorophenyl)-4-oxo-6-[3-(pyrrolidin-1-ylmethyl)cyclobutyl]quinazolin-3-yl]-N-isopropyl-acetamide (Example 9: compound of formula I.4, wherein Q is Q.6, Y is CH, $R^{5a}$ is H, $R^{5b}$ is H and $R^{5c}$ is Cl and where the substituents on the 1,3-cyclobutandiyl radical adopt the cis configuration)
ESI-MS: 496.20; 495.20; $[M]^+$=493.20; 247.20.

Example 10 cis-2-[2-(3-Chlorophenyl)-6-[3-[(4-methoxy-1-piperidyl)methyl]cyclobutyl]-4-oxo-quinazolin-3-yl]-N-isopropyl-acetamide (Example 10: compound of formula I.4, wherein Q is Q.17, Y is CH, $R^{5a}$ is H, $R^{5b}$ is H and $R^{5c}$ is Cl and where the substituents on the 1,3-cyclobutandiyl radical adopt the cis configuration)
ESI-MS: 540.20; $[M+H]^+$=538.20; 537.20; 269.20.

Example 11 cis-2-[2-(3-Chlorophenyl)-6-[3-[[(3R)-3-fluoropyrrolidin-1-yl]methyl]cyclobutyl]-4-oxo-quinazolin-3-yl]-N-isopropyl-acetamide (Example 11: R-enantiomer of the compound of formula I.4, wherein Q is Q.7, Y is CH, $R^{5a}$ is H, $R^{5b}$ is H and $R^{5c}$ is Cl and where the substituents on the 1,3-cyclobutandiyl radical adopt the cis configuration)
ESI-MS: 514.20; $[M+H]^+$=512.20; 511.20; 256.20.

Example 12 cis-2-[2-(3-Chlorophenyl)-6-[3-[(4,4-difluoro-1-piperidyl)methyl]cyclobutyl]-4-oxo-quinazolin-3-yl]-N-isopropyl-acetamide (Example 12: compound of formula I.4, wherein Q is Q.22, Y is CH, $R^{5a}$ is H, $R^{5b}$ is H and $R^{5c}$ is Cl and where the substituents on the 1,3-cyclobutandiyl radical adopt the cis configuration)
$^1$H NMR (CDCl$_3$, 600 MHz): 8.11 (s br., 1H), 7.69 (d, 1H), 7.65 (s, 1H), 7.64 (t, 1H), 7.56 (d, 1H), 7.44 (d, 1H), 7.42 (t, 1H), 5.56-5.59 (m br., 1H), 4.46-4.51 (m, 2H), 4.09 (sext., 1H), 3.56-3.62 (m br., 1H), 2.43-2.69 (m br., 7H), 1.85-2.10 (m br., 6H), 1.21-1.38 (m, 3H), 1.17 (d, 6H).

Example 13 cis-2-[2-(3-Chlorophenyl)-6-[3-(morpholinomethyl)cyclobutyl]-4-oxo-quinazolin-3-yl]-N-isopropyl-acetamide (Example 13: compound of formula I.4, wherein Q is Q.29, Y is CH, $R^{5a}$ is H, $R^{5b}$ is H and $R^{5c}$ is Cl and where the substituents on the 1,3-cyclobutandiyl radical adopt the cis configuration)
ESI-MS: 512.20; $[M]^+$=509.20; 255.60.

Example 14 cis-2-[2-(3-Chlorophenyl)-6-[3-[(3-cyano-1-piperidyl)methyl]cyclobutyl]-4-oxo-quinazolin-3-yl]-N-isopropyl-acetamide (Example 14: compound of formula I.4, wherein Q is Q.26, Y is CH, $R^{5a}$ is H, $R^{5b}$ is H and $R^{5c}$ is Cl and where the substituents on the 1,3-cyclobutandiyl radical adopt the cis configuration)
ESI-MS: 535.20; $[M+H]^+$=533.20; 532.20; 267.30; 266.70.

Example 15 cis-2-[2-(3-Chlorophenyl)-6-[3-(diethylaminomethyl)cyclobutyl]-4-oxo-quinazolin-3-yl]-N-isopropyl-acetamide (Example 15: compound of formula I.4, wherein Q is diethylamine, Y is CH, $R^{5a}$ is H, $R^{5b}$ is H and $R^{5c}$ is Cl and where the substituents on the 1,3-cyclobutandiyl radical adopt the cis configuration)
ESI-MS: 498.20; $[M+H]^+$=496.20; 495.20; 248.20.

Example 16 cis-2-[2-(3-Chlorophenyl)-6-[3-[ [(3S)-3-fluoropyrrolidin-1-yl]methyl]cyclobutyl]-4-oxo-quinazolin-3-yl]-N-isopropyl-acetamide (Example 16: S-enantiomer of the compound of formula I.4, wherein Q is Q.7, Y is CH, $R^{5a}$ is H, $R^{5b}$ is H and $R^{5c}$ is Cl and where the substituents on the 1,3-cyclobutandiyl radical adopt the cis configuration)
ESI-MS: 514.20; $[M]^+$=511.20; 256.20.

Example 17 cis-2-[2-(3-Chlorophenyl)-6-[3-(dimethylaminomethyl)cyclobutyl]-4-oxo-quinazolin-3-yl]-N-isopropyl-acetamide (Example 17: compound of formula I.4, wherein Q is dimethylamine, Y is CH, $R^{5a}$ is H, $R^{5b}$ is H and $R^{5c}$ is Cl and where the substituents on the 1,3-cyclobutandiyl radical adopt the cis configuration)
ESI-MS: 470.20; $[M+H]^+$=468.20; 467.20; 234.20.

Example 18 cis-2-[2-(3-Chlorophenyl)-6-[3-(3,6-dihydro-2H-pyridin-1-ylmethyl)cyclobutyl]-4-oxo-quinazolin-3-yl]-N-isopropyl-acetamide (Example 18: compound of formula I.4, wherein Q is Q.28, Y is CH, $R^{5a}$ is H, $R^{5b}$ is H and $R^{5c}$ is Cl and where the substituents on the 1,3-cyclobutandiyl radical adopt the cis configuration)
ESI-MS: 508.20; [M+H]$^+$=506.20; 505.20; 253.20.

Example 19 cis-2-[2-(3-Chlorophenyl)-6-[3-[(3-fluoroazetidin-1-yl)methyl]cyclobutyl]-4-oxo-quinazolin-3-yl]-N-isopropyl-acetamide (Example 19: compound of formula I.4, wherein Q is Q.2, Y is CH, $R^{5a}$ is H, $R^{5b}$ is H and $R^{5c}$ is Cl and where the substituents on the 1,3-cyclobutandiyl radical adopt the cis configuration)
ESI-MS: 500.20; [M+H]$^+$=498.20; 497.20; 249.20.

Example 20 cis-2-[2-(3-Chlorophenyl)-6-[3-[(4-ethoxy-1-piperidyl)methyl]cyclobutyl]-4-oxo-quinazolin-3-yl]-N-isopropyl-acetamide (Example 20: compound of formula I.4, wherein Q is Q.18, Y is CH, $R^{5a}$ is H, $R^{5b}$ is H and $R^{5c}$ is Cl and where the substituents on the 1,3-cyclobutandiyl radical adopt the cis configuration)
ESI-MS: [M+H]$^+$=552.30; 551.30; 504.20; 276.20;

Example 21 cis-2-[6-[3-(Azepan-1-ylmethyl)cyclobutyl]-2-(3-chlorophenyl)-4-oxo-quinazolin-3-yl]-N-isopropyl-acetamide (Example 21: compound of formula I.4, wherein Q is Q.34, Y is CH, $R^{5a}$ is H, $R^{5b}$ is H and $R^{5c}$ is Cl and where the substituents on the 1,3-cyclobutandiyl radical adopt the cis configuration)
ESI-MS: 524.20; [M]$^+$=521.20; 261.20.

Example 22 cis-2-[2-(3-Chlorophenyl)-6-[3-[(4-methyl-1-piperidyl)methyl]cyclobutyl]-4-oxo-quinazolin-3-yl]-N-isopropyl-acetamide (Example 22: compound of formula I.4, wherein Q is Q.19, Y is CH, $R^{5a}$ is H, $R^{5b}$ is H and $R^{5c}$ is Cl and where the substituents on the 1,3-cyclobutandiyl radical adopt the cis configuration)
ESI-MS: 524.30; [M+H]$^+$=522.30; 521.30; 261.20.

Example 23 cis-2-[2-(3-Chlorophenyl)-6-[3-[(3-hydroxy-8-azabicyclo[3.2.1]octan-8-yl)methyl]cyclobutyl]-4-oxo-quinazolin-3-yl]-N-isopropyl-acetamide (Example 23: Compound of formula I.4, wherein Q is Q.37, Y is CH, $R^{5a}$ is H, $R^{5b}$ is H and $R^{5c}$ is Cl and where the substituents on the 1,3-cyclobutandiyl radical adopt the cis configuration)
ESI-MS: 552.20; [M]$^+$=549.20; 275.20.

Example 24 cis-2-[2-(3-Chlorophenyl)-6-[3-[[(3S)-3-methylpyrrolidin-1-yl]methyl]cyclobutyl]-4-oxo-quinazolin-3-yl]-N-isopropyl-acetamide (Example 24: S-enantiomer of the compound of formula I.4, wherein Q is Q.8, Y is CH,
$R^{5a}$ is H, $R^{5b}$ is H and $R^{5c}$ is Cl and where the substituents on the 1,3-cyclobutandiyl radical adopt the cis configuration)
ESI-MS: 510.30; [M+H]$^+$=508.30; 507.30; 254.20.

Example 25 cis-2-[2-(3-Chlorophenyl)-6-[3-(1,4-oxazepan-4-ylmethyl)cyclobutyl]-4-oxo-quinazolin-3-yl]-N-isopropyl-acetamide (Example 25: Compound of formula I.4, wherein Q is Q.35, Y is CH, $R^{5a}$ is H, $R^{5b}$ is H and $R^{5c}$ is Cl and where the substituents on the 1,3-cyclobutandiyl radical adopt the cis configuration)
ESI-MS: 526.20; [M]$^+$=523.20; 262.20.

The compounds of examples 26 to 29 were prepared in an analogous manner as described above, starting from the compound of example 6. The amidation reaction was carried out in an analogous manner as described in example 6.

Example 26 cis-N-tert-Butyl-2-[2-(3-chlorophenyl)-4-oxo-6-[3-(1-piperidylmethyl)cyclobutyl]-quinazolin-3-yl]acetamide (Example 26: compound of formula I.6, wherein Q is Q.14, Y is CH, $R^{5a}$ is H, $R^{5b}$ is H and $R^{5c}$ is Cl and where the substituents on the 1,3-cyclobutandiyl radical adopt the cis configuration)
ESI-MS: 524.30; [M]$^+$=521.20; 261.20.

Example 27 cis-2-[2-(3-Chlorophenyl)-4-oxo-6-[3-(1-piperidylmethyl)cyclobutyl]quinazolin-3-yl]-N-cyclopropyl-acetamide (Example 27: compound of formula I.9, wherein Q is Q.14, Y is CH, $R^{5a}$ is H, $R^{5b}$ is H and $R^{5c}$ is Cl and where the substituents on the 1,3-cyclobutandiyl radical adopt the cis configuration)
ESI-MS: 508.20; [M]$^+$=505.20; 253.20.

Example 28 cis-2-[2-(3-Chlorophenyl)-4-oxo-6-[3-(1-piperidylmethyl)cyclobutyl]quinazolin-3-yl]-N-propyl-acetamide (Example 28: compound of formula I.3, wherein Q is Q.14, Y is CH, $R^{5a}$ is H, $R^{5b}$ is H and $R^{5c}$ is Cl and where the substituents on the 1,3-cyclobutandiyl radical adopt the cis configuration)

$^1$H NMR (CDCl$_3$, 600 MHz): 8.08 (s, 1H), 7.70 (d, 1H), 7.66 (t, 1H), 7.59 (d, 1H), 7.57 (d, 1H), 7.50 (d, 1H), 7.43 (t, 1H), 5.80 (s br., 1H), 4.53 (s, 2H), 3.42-3.70 (2 m, 1+2H), 3.27 (q, 2H), 3.01 (s br., 1H), 2.77 (br. s., 2H), 2.60 (m, 2H), 2.57 (s br., 2H), 1.96 & 1.92 (2 m, 3+2H), 0.93 (t, 2H).

Example 29 cis-2-[2-(3-Chlorophenyl)-4-oxo-6-[3-(1-piperidylmethyl)cyclobutyl]quinazolin-3-yl]-N-(cyclopropylmethyl)acetamide (Example 29: compound of formula I.10, wherein Q is Q.14, Y is CH, R$^{5a}$ is H, R$^{5b}$ is H and R$^{5c}$ is Cl and where the substituents on the 1,3-cyclobutandiyl radical adopt the cis configuration)

ESI-MS: 522.20; [M]$^+$=519.20; 261.00; 260.20.

The compounds of examples 30 to 44 were prepared in an analogous manner as described in example 7.

Example 30 cis-2-[2-(3-Chlorophenyl)-6-[3-[(4-fluoro-1-piperidyl)methyl]cyclobutyl]-4-oxo-quinazolin-3-yl]-N-isopropyl-acetamide (Example 30: compound of formula I.4, wherein Q is Q.15, Y is CH, R$^{5a}$ is H, R$^{5b}$ is H and R$^{5c}$ is Cl and where the substituents on the 1,3-cyclobutandiyl radical adopt the cis configuration)

ESI-MS: 528.20; [M+H]$^+$=526.20; 525.20; 263.20.

Example 31 cis-2-[2-(3-Chlorophenyl)-6-[3-(6-oxa-2-azaspiro[3.3]heptan-2-ylmethyl)cyclobutyl]-4-oxo-quinazolin-3-yl]-N-isopropyl-acetamide (Example 31: compound of formula I.4, wherein Q is Q.38, Y is CH, R$^{5a}$ is H, R$^{5b}$ is H and R$^{5c}$ is Cl and where the substituents on the 1,3-cyclobutandiyl radical adopt the cis configuration)

ESI-MS: [M+H]$^+$=522.20; 521.20; 261.20.

Example 32 cis-2-[2-(3-Chlorophenyl)-6-[3-[(4-hydroxy-1-piperidyl)methyl]cyclobutyl]-4-oxo-quinazolin-3-yl]-N-isopropyl-acetamide (Example 32: compound of formula I.4, wherein Q is Q.16, Y is CH, R$^{5a}$ is H, R$^{5b}$ is H and R$^{5c}$ is Cl and where the substituents on the 1,3-cyclobutandiyl radical adopt the cis configuration)

ESI-MS: 526.20; [M]$^+$=523.20; 262.20.

Example 33 cis-2-[2-(3-Chlorophenyl)-6-[3-[[(3R)-3-hydroxy-1-piperidyl]methyl]cyclobutyl]-4-oxo-quinazolin-3-yl]-N-isopropyl-acetamide (Example 33: R-enantiomer of the compound of formula I.4, wherein Q is Q.25, Y is CH, R$^{5a}$ is H, R$^{5b}$ is H and R$^{5c}$ is Cl and where the substituents on the 1,3-cyclobutandiyl radical adopt the cis configuration)

ESI-MS: 526.20; [M+H$^+$]=524.20; 523.20; 262.20.

Example 34 cis-2-[2-(3-Chlorophenyl)-6-[3-[[(3R)-3-methylpyrrolidin-1-yl]methyl]cyclobutyl]-4-oxo-quinazolin-3-yl]-N-isopropyl-acetamide (Example 34: R-enantiomer of the compound of formula I.4, wherein Q is Q.8, Y is CH, R$^{5a}$ is H, R$^{5b}$ is H and R$^{5c}$ is Cl and where the substituents on the 1,3-cyclobutandiyl radical adopt the cis configuration)

ESI-MS: 510.20; [M+H]$^+$=508.20; 507.20; 254.20.

Example 35 cis-2-[2-(3-Chlorophenyl)-6-[3-[(3-methoxyazetidin-1-yl)methyl]cyclobutyl]-4-oxo-quinazolin-3-yl]-N-isopropyl-acetamide (Example 35: compound of formula I.4, wherein Q is Q.4, Y is CH, R$^{5a}$ is H, R$^{5b}$ is H and R$^{5c}$ is Cl and where the substituents on the 1,3-cyclobutandiyl radical adopt the cis configuration)

ESI-MS: 512.20; [M+H]$^+$=510.20; 509.20; 255.20.

Example 36 cis-2-[2-(3-Chlorophenyl)-6-[3-[(4-hydroxy-4-methyl-1-piperidyl)methyl]cyclobutyl]-4-oxo-quinazolin-3-yl]-N-isopropyl-acetamide (Example 36: compound of formula I.4, wherein Q is Q.23, Y is CH, R$^{5a}$ is H, R$^{5b}$ is H and R$^{5c}$ is Cl and where the substituents on the 1,3-cyclobutandiyl radical adopt the cis configuration)

ESI-MS: 540.20; [M+H]$^+$=538.20; 537.20; 269.20.

Example 37 cis-2-[2-(3-Chlorophenyl)-6-[3-[ [(3S)-3-hydroxy-1-piperidyl]methyl]cyclobutyl]-4-oxo-quinazolin-3-yl]-N-isopropyl-acetamide (Example 37: S-enantiomer of the compound of formula I.4, wherein Q is Q.25, Y is CH, R$^{5a}$ is H, R$^{5b}$ is H and R$^{5c}$ is Cl and where the substituents on the 1,3-cyclobutandiyl radical adopt the cis configuration)

ESI-MS: 526.20; [M+H]$^+$=524.20; 523.20; 262.20.

Example 38 cis-2-[2-(3-Chlorophenyl)-4-oxo-6-[3-[[4-(trifluoromethyl)-1-piperidyl]methyl]cyclobutyl]quinazolin-3-yl]-N-isopropyl-acetamide (Example 38: compound of formula I.4, wherein Q is Q.20, Y is CH, R$^{5a}$ is H, R$^{5b}$ is H and R$^{5c}$ is Cl and where the substituents on the 1,3-cyclobutandiyl radical adopt the cis configuration)
ESI-MS: 578.40; [M+H]⁺=576.40; 575.40; 288.20.

Example 39 cis-2-[2-(3-Chlorophenyl)-6-[3-[(3-fluoro-1-piperidyl)methyl]cyclobutyl]-4-oxo-quinazolin-3-yl]-N-isopropyl-acetamide (Example 39: compound of formula I.4, wherein Q is Q.24, Y is CH, $R^{5a}$ is H, $R^{5b}$ is H and $R^{5c}$ is Cl and where the substituents on the 1,3-cyclobutandiyl radical adopt the cis configuration)
¹H NMR (CDCl₃, 600 MHz): δ=8.11 (s, 1H), 7.69 (d, 1H), 7.65 (s, 1H), 7.63 (t, 1H), 7.56 (d, 1H), 7.49 (d, 1H), 7.43 (t, 1H), 5.59 (d, 1H), 4.71 & 4.62 (2 br. s., 1H), 4.49 (s, 2H), 4.10 (sext, 1H), 3.54 (quint, 1H), 2.79 (br. s., 1H), 2.43-2.68 (m br., 5H), 2.31 (br. s., 1H), 1.83-1.91 (m, 2H), 1.52-1.83 (br. m, 6H), 1.18 (s, 6H).

Example 40 cis-2-[2-(3-Chlorophenyl)-6-[3-[(3-hydroxyazetidin-1-yl)methyl]cyclobutyl]-4-oxo-quinazolin-3-yl]-N-isopropyl-acetamide (Example 40: compound of formula I.4, wherein Q is Q.3, Y is CH, $R^{5a}$ is H, $R^{5b}$ is H and $R^{5c}$ is Cl and where the substituents on the 1,3-cyclobutandiyl radical adopt the cis configuration)
ESI-MS: 498.20; [M+H]⁺=496.40; 95.40; 248.20.

Example 41 cis-2-[2-(3-Chlorophenyl)-6-[3-(7-oxa-2-azaspiro[3.5]nonan-2-ylmethyl)cyclobutyl]-4-oxo-quinazolin-3-yl]-N-isopropyl-acetamide (Example 41: compound of formula I.4, wherein Q is Q.39, Y is CH, $R^{5a}$ is H, $R^{5b}$ is H and $R^{5c}$ is Cl and where the substituents on the 1,3-cyclobutandiyl radical adopt the cis configuration)
ESI-MS: 552.20; [M+H]⁺=550.20; 549.20.

Example 42 cis-2-[2-(3-Chlorophenyl)-6-[3-[[(2S,6R)-2,6-dimethylmorpholin-4-yl]methyl]cyclobutyl]-4-oxo-quinazolin-3-yl]-N-isopropyl-acetamide (Example 42: compound of formula I.4, wherein Q is (2S,6R)-2,6-dimethylmorpholin-4-yl, Y is CH, $R^{5a}$ is H, $R^{5b}$ is H and $R^{5c}$ is Cl and where the substituents on the 1,3-cyclobutandiyl radical adopt the cis configuration)
ESI-MS: 540.20; [M+H]⁺=538.20; 537.20.

Example 43 cis-2-[2-(3-Chlorophenyl)-6-[3-[(2,6-dimethylmorpholin-4-yl)methyl]cyclobutyl]-4-oxo-quinazolin-3-yl]-N-isopropyl-acetamide (Example 43: compound of formula I.4, wherein Q is Q.30, Y is CH, $R^{5a}$ is H, $R^{5b}$ is H and $R^{5c}$ is Cl and where the substituents on the 1,3-cyclobutandiyl radical adopt the cis configuration)
ESI-MS: 540.20; [M+H]⁺=538.20; 537.20; 269.20.

Example 44 cis-2-[2-(3-Chlorophenyl)-6-[3-[[(3R)-3-methylmorpholin-4-yl]methyl]cyclobutyl]-4-oxo-quinazolin-3-yl]-N-isopropyl-acetamide (Example 44: R-enantiomer of the compound of formula I.4, wherein Q is Q.32, Y is CH, $R^{5a}$ is H, $R^{5b}$ is H and $R^{5c}$ is Cl and where the substituents on the 1,3-cyclobutandiyl radical adopt the cis configuration)
¹H NMR (CDCl₃, 600 MHz): δ=8.11 (s, 1H), 7.69 (d, 1H), 7.65 (s, 1H), 7.62 (t, 1H), 7.56 (d, 1H), 7.49 (d, 1H), 7.43 (t, 1H), 5.58 (d, 1H), 4.49 (s, 2H), 4.10 (sext., 1H), 3.81 (br. s., 1H), 3.67 (br. s., 2H), 3.57 (m sym., 1H), 3.26 (br. s., 1H), 2.79 (br. d., 2H), 2.61 (br. s., 3H), 2.28-2.47 (br. m., 3H), 1.89 (br. m., 2H), 1.18 (d, 6H), 1.00 (s. br, 2H).

The compounds of examples 45 and 46 were prepared in analogy to the method described above starting from the compound of example 6.

Example 45 cis-2-[2-(3-Chlorophenyl)-4-oxo-6-[3-(1-piperidylmethyl)cyclobutyl]quinazolin-3-yl]-[(1S)-2,2,2-trifluoro-1-methyl-ethyl]acetamide (Example 45: S-enantiomer of the cis compound of formula I.7, wherein Q is Q.14, Y is CH, $R^{5a}$ is H, $R^{5b}$ is H and $R^{5c}$ is Cl and where the substituents on the 1,3-cyclobutandiyl radical adopt the cis configuration)
ESI-MS: 564.20; [M+H]⁺=562.20; 561.20; 282.20.

Example 46 cis-2-[2-(3-Chlorophenyl)-4-oxo-6-[3-(1-piperidylmethyl)cyclobutyl]quinazolin-3-yl]-N-[(1R)-2,2,2-trifluoro-1-methyl-ethyl]acetamide (Example 46: R-enantiomer of the cis-compound of formula I.7, wherein Q is Q.14, Y is CH, $R^{5a}$ is H, $R^{5b}$ is H and $R^{5c}$ is Cl and where the substituents on the 1,3-cyclobutandiyl radical adopt the cis configuration)

Example 47

2-[2-(3-Chlorophenyl)-4-oxo-6-[3-[2-(1-piperidyl)ethyl]cyclobut-2-en-1-yl]quinazolin-3-yl]-N-isopropyl-acetamide (Example 47: compound of formula I, where $X^1$=$X^2$=N; $X^3$=$X^4$=$X^5$=CH; $R^1$=CH₂C(O)NHCH(CH₃)₂; $R^2$=3-chlorophenyl; $R^3$ is 3-[2-(1-piperidyl)ethyl]cyclobut-2-en-1-yl 47.1 But-3-enoxy-tert-butyl-diphenyl-silane To a solution of but-3-en-1-ol (20 g, 0.28 mol), 1H-imidazole (28.3 g, 0.42 mmol) and N,N-dimethylpyridin-4-amine (3.4 g, 0.028 mol) in DCM (800 mL) was added tert-butyl(chloro)diphenylsilane (84.4 g, 0.31 mol). The mixture was stirred for 24 h at rt. After water (100 mL) was added to the solution, the mixture was extracted with EtOAc (50 mL*3), dried over Na₂SO₄, filtered and concentrated.

The residue was purified by prep-TLC (eluting with: DCM: MeOH=100:1) to give the title compound (68.8 g, 0.22 mol, 80% yield) as a pale with oil.

$^1$H NMR: (400 MHz, CDCl$_3$): δ 7.68-7.66 (m, 4H), 7.40-7.34 (m, 6H), 5.83-5.82 (m, 1H), 5.07-4.99 (m, 2H), 3.72 (t, J=6.8 Hz, 2H), 2.34-2.30 (m, 2H), 1.05 (s, 9H).

47.2 3-[2-[tert-Butyl(diphenyl)silyl]oxyethyl]-2,2-dichloro-cyclobutanone

To a solution of the compound of example 47.1 (6 g, 0.019 mol) and Cu—Zn (6.8 g, 0.038 mol) in diethyl ether (60 mL) was added 2,2,2-trichloroacetyl chloride (3.4 g, 0.019 mol). The mixture was stirred at 60° C. for 16 h. After water (100 mL) was added to the solution, the mixture was extracted with EtOAc (50 mL*3=150 mL), dried over Na$_2$SO$_4$, filtered and concentrated to give the crude title compound (crude 8 g) as a pale yellow oil, which was used in the next step without purification.

$^1$H NMR: (400 MHz, CDCl$_3$): δ 7.68-7.66 (m, 4H), 7.48-7.25 (m, 6H), 3.84-3.74 (m, 2H), 3.33-2.90 (m, 3H), 2.22-2.17 (m, 1H), 1.83-1.81 (m, 1H), 1.08 (s, 9H).

47.3 3-[2-[tert-Butyl(diphenyl)silyl]oxyethyl]cyclobutanone

To a solution of crude compound of example 47.2 (8 g) in CH$_3$COOH (24 mL) was added Zn (5.4 g, 0.097 mol). The mixture was stirred for 3 h at 60° C., filtered and concentrated. Water (100 mL) was added to the residue, the mixture was extracted with EtOAc (50 mL*3), dried over Na$_2$SO$_4$, filtered and concentrated to give the crude title compound (3.5 g, 0.01 mol, 51% yield) as a pale yellow oil.

$^1$H NMR: (400 MHz, CDCl$_3$): δ 7.74-7.66 (m, 4H), 3.73-3.70 (m, 2H), 3.16-3.10 (m, 2H), 2.70-2.50 (m, 2H), 2.22-2.17 (m, 1H), 1.85 (dd, J$_1$=2.0 Hz, J$_2$=6.8 Hz, 2H), 1H), 1.07 (s, 9H).

47.4 [3-[2-[tert-Butyl(diphenyl)silyl]oxyethyl]cyclobut-2-en-1-yl]trifluoromethanesulfonate To a solution of the compound of example 47.3 (0.5 g, 1.36 mmol) in THF (20 mL) was added lithium bis(trimethylsilyl)amide (1.36 mL, 1.36 mmol) at −78° C. The mixture was allowed to stir for 1 h at −78° C. Then, trifluoro-N-phenyl-N-(trifluoromethylsulfonyl)methanesulfonamide (0.48 g, 1.36 mmol) in THF (4 mL) was added to the solution at −78° C. The mixture was stirred for 16 h at −78° C. to rt. The mixture was concentrated. Then, 2-methoxy-2-methylpropane (50 mL) was added, the mixture was washed with NaOH (1N) and concentrated. The residue was purified by a silica gel column chromatograph (eluting with: PE:EA=75:1) to give the title crude compound (0.8 g) as a pale brown oil which was used in the next step without purification.

47.5 2-[6-[3-[2-[tert-Butyl(diphenyl)silyl]oxyethyl]cyclobut-2-en-1-yl]-2-(3-chlorophenyl)-4-oxo-quinazolin-3-yl]-N-isopropyl-acetamide To a solution of the crude compound of example 47.4 (0.8 g) and the compound of example 1.4 (0.99 g, 2.1 mmol) in toluene/water=4:1 (50 mL) was added Na$_2$CO$_3$ (5.8 g, 4.2 mmol) and Pd(PPh$_3$)$_4$ (100 mg, 0.021 mmol). The mixture was degassed via N$_2$ atmosphere for three times and allowed to stir for 16 h at 60° C.

The reaction mixture was poured into water (100 ml), extracted with EA (50 mL*3), and concentrated to give the crude title product. The residue was purified by a silica gel column chromatograph (eluting with: PE:EA=75:1) to give the title compound (215 mg, 0.47 mmol) as a pale white solid.

LCMS: ESI-MS: m/z: 690.0 [M+H]$^+$; RT=2.50 min (Method H).

47.6 2-[2-(3-Chlorophenyl)-6-[3-(2-hydroxyethyl)cyclobut-2-en-1-yl]-4-oxo-quinazolin-3-yl]-N-isopropyl-acetamide To a solution of the compound of example 47.5 (212 mg, 0.31 mmol) in THF (4 mL) was added TBAF (111 mg, 0.46 mmol). The mixture was stirred for 16 h at rt. Then, the mixture was concentrated to give the crude product. The residue was purified by a silica gel column chromatograph (eluting with: DCM:MeOH=10:1) to give the title compound (125 mg, 0.028 mmol, 90% yield) as a pale yellow oil.

LCMS: ESI-MS: m/z: 452.0 [M+H]$^+$; RT=1.62 min (Method H)

47.7 2-[3-[2-(3-Chlorophenyl)-3-[2-(isopropylamino)-2-oxo-ethyl]-4-oxo-quinazolin-6-yl]cyclobuten-1-yl]ethyl methanesulfonate The title compound was prepared in analogy to the method described in example 1.11 but the reaction mixture was stirred for 16 h at room temperature. The title compound was obtained as a pale white solid (yield: 80%) and was used in the next step without purification.

LCMS: ESI-MS: m/z: 530.0 [M+H]$^+$; RT=1.70 min (Method H).

$^1$H NMR: (400 MHz, CDCl$_3$): δ 8.17 (s, 1H), 7.80-7.26 (m, 6H), 6.52 (s, 1H), 5.66-5.60 (m, 0.55H), 34.49 (s, 1H), 3.66-3.63 (m, 2H), 4.37-4.33 (m, 1H), 4.07-4.06 (m, 1H), 3.14-3.10 (m, 1H), 3.09 (s, 3H), 2.05-2.03 (m, 1H), 1.40-1.24 (m, 4H), 1.18 (d, J=6.8 Hz, 6H).

47.8 2-[2-(3-Chlorophenyl)-4-oxo-6-[3-[2-(1-piperidyl)ethyl]cyclobut-2-en-1-yl]quinazolin-3-yl]-N-isopropyl-acetamide To a solution of the compound of example 47.7 (113 mg, 0.21 mmol), piperidine (18.2 mg, 0.21 mmol), and acetic acid (catalytic amount) in CH$_3$ (10 mL) was added K$_2$CO$_3$ (58 mg, 0.42 mmol). The mixture was stirred for 7 h at 80° C. in a microwave reactor. Then, the reaction mixture was concentrated to give the crude product. The residue was purified by a silica gel column chromatograph (eluting with: DCM:MeOH=10:1) to give the title compound (83 mg, 0.16 mmol, 75% yield) as a pale white solid.

LCMS: ESI-MS: m/z: 519.0 [M+H]$^+$; RT=1.18 min (Method I).

$^1$H NMR: (400 MHz, CDCl$_3$): δ 8.16 (s, 1H), 7.79-7.78 (m, 1H), 7.70-7.48 (m, 3H), 7.45-7.26 (m, 2H), 6.51 (s, 1H), 5.64 (d, J=8.0 Hz, 6H), 4.49 (s, 2H), 4.07-4.06 (m, 1H), 3.03-3.02 (m, 1H), 2.87-2.43 (m, 6H), 1.94-1.53 (m, 10H), 1.18 (d, J=6.8 Hz, 6H).

Example 48

2-[2-(3-Chlorophenyl)-4-oxo-6-[3-[2-(1-piperidyl)ethyl]cyclobutyl]quinazolin-3-yl]-N-isopropyl-acetamide (Example 48: compound of formula I.14, wherein Q is Q.14, Y is CH, R$^{5a}$ is H, R$^{5b}$ is H and R$^{5c}$ is Cl)

To a solution of the compound of example 47.8 (82.6 mg, 0.159 mmol) in MeOH (4 mL) was added Pd(OH)$_2$ (15 mg, 0.07 mmol). The mixture was degassed via N$_2$ atmosphere and then allowed to stir for 0.5 h at rt. The reaction mixture was filtered and concentrated. The obtained residue was purified by prep-HPLC to give the title compound (50 mg, 0.096 mmol, 60% yield) as a pale white solid, being a mixture of cis and trans isomers in the ratio of about 1.65:1.

LCMS: ESI-MS: m/z: 521.0 [M+H]$^+$; RT=1.14 min (Method E).

$^1$H NMR: (400 MHz, CDCl$_3$): δ 8.09-8.08 (m, 1H), 7.68-7.42 (m, 6H), 5.62-5.60 (m, 1H), 4.48 (s, 2H), 4.11-4.06 (m, 1H), 3.71-3.46 (m, 1H), 2.57-2.56 (m, 1H), 2.37-2.20 (m, 7H), 1.87-1.89 (m, 2H), 1.65-1.61 (m, 7H), 1.44-1.17 (m, 2H), 1.17 (d, J=6.8 Hz, 6H).

II. Determination of the Biological Activity

1. Vasopressin V1b Receptor Binding Assay:

Substances:

The test substances were dissolved in a concentration of 5 mM in 100% DMSO and further diluted to $5 \times 10^{-4}$ M to $5 \times 10^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (200 μl), membranes (26 μg protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 μM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:

Substances:

The test substances were dissolved in a concentration of 5 mM M in DMSO. Further dilution of these DMSO solutions took place as described for V1b.

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (200 μl), membranes (40 μg protein in incubation buffer) from CHO-K1 cells with stably expressed human V1a receptors (cell line hV1a_5_CHO) were incubated with 0.04 nM $^{125}$I-AVP (8-Arg-vasopressin, PerkinElmer NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 μM AVP (Fluka 94836). Duplicate determinations were carried out.

After incubation (60 minutes at room temperature), the samples were processed as described for V1b.

Analysis:

The binding parameters were calculated by nonlinear regression in SAS. The algorithms of the program operate in analogy to the LIGAND analysis program (Munson PJ and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Membrane Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. Cell lysates were then centrifuged at 750×g at 4° C. for 20 minutes, the residue was taken up in incubation buffer (50 mM Tris, 10 mM MgCl$_2$, 0.1% BSA, pH 7.4), and aliquots corresponding to 10$^7$ cells/ml were prepared. The aliquots were frozen at −80° C. until use.

Binding Assay:

On the day of the experiment, the cell lysate was thawed, homogenized, and diluted with incubation buffer (50 mM Tris, 10 mM MgCl$_2$, 0.1% BSA, pH 7.4) to the desired concentration. The reaction mixture of 0.200 ml was composed of cell lysate corresponding to $5 \times 10^4$ cells (HEK-293 cells expressing transiently human OT receptors) and 1 nM 3H-oxytocin (PerkinElmer NET858) in the presence of test substance (displacement experiment) or incubation buffer only (total binding). The nonspecific binding was determined in the presence of 1 µM oxytocin (Bachem AG, H2510). Determinations were carried out in duplicates. After 60 minutes incubation at room temperature, bound and free radioligand were separated by filtration under vacuum on GF/B UniFilter plates (Perkin Elmer #6005177) pre-incubated with 0.3% PEI. The bound radioactivity was determined by liquid scintillation measurement in a Microbeta (Perkin Elmer) plate counter.

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant human OT receptors was 7.6 nM and was used to calculate the Ki from competition binding experiments.

4. Determination of the Microsomal Half-Life

The metabolic stability of the compounds of the invention was determined in the following assay.

The test substances were incubated in a concentration of 0.5 µM as follows: 0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomolecular Screening, 2003, 453-462; Obach, D M D, 1999 vol 27. N 11, 1350-1359).

5. Methods for In Vitro Determination of the Cytochrome P450 (CYP) Inhibition

Luminescent Substrates for 2C9 and 3A4:

0.4 mg/ml human liver microsomes are preincubated with the test substances to be investigated (0-20 µM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 µM (or 50 µM) test substance in 50 mM potassium phosphate buffer for 5 min. The reaction is started with NADPH. After 30 min 4 µM midazolam (final concentration) are added, and incubation is continued for 10 min. 75 µl of the reaction solution are removed after 10 min, and stopped with 150 µl of acetonitrile solution.

Coincubation:

0.05 mg/ml microsomal protein (human liver microsomes) are preincubated with 4 µm midazolam (final concentration) and 0-10 µM (or 50 µM) test substance in 50 mM potassium phosphate buffer for 5 min. The reaction is started with NADPH. 75 µl of the reaction solution are removed after 10 min and stopped with 150 µl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in Mg/Ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and a good metabolic stability, measured as microsomal clearance.

The results are listed in table B. The numbers of the compounds refer to the synthesis examples.

TABLE B

| Ex. | $K_i$(h-V1b)* [nM] | $K_i$(h-V1a)/$K_i$(h-V1b) |
|---|---|---|
| 1 | + | +++ |
| 2a | ++ | +++ |
| 2b | + | +++ |
| 3 | + | ++ |
| 4 | + | +++ |
| 7 | + | +++ |
| 8 | +++ | +++ |
| 9 | + | +++ |
| 10 | ++ | +++ |
| 11 | ++ | +++ |
| 12 | ++ | +++ |
| 13 | ++ | +++ |
| 14 | ++ | +++ |
| 15 | + | +++ |
| 16 | ++ | +++ |
| 17 | + | +++ |
| 18 | ++ | +++ |
| 19 | ++ | +++ |
| 20 | + | +++ |
| 21 | ++ | +++ |
| 22 | ++ | +++ |

TABLE B-continued

| | | |
|---|---|---|
| 23 | ++ | +++ |
| 24 | + | +++ |
| 25 | ++ | +++ |
| 26 | +++ | +++ |
| 27 | + | +++ |
| 28 | + | +++ |
| 29 | + | +++ |
| 30 | ++ | +++ |
| 31 | ++ | +++ |
| 32 | + | +++ |
| 33 | ++ | +++ |
| 34 | ++ | +++ |
| 35 | + | +++ |
| 36 | ++ | +++ |
| 37 | ++ | +++ |
| 38 | ++ | +++ |
| 39 | ++ | +++ |
| 40 | ++ | +++ |
| 41 | ++ | +++ |
| 42 | ++ | +++ |
| 43 | + | +++ |
| 44 | ++ | +++ |
| 45 | ++ | +++ |
| 46 | + | ++ |

*h = human
Ex. = Example
Key:

| | $K_i$(h-V1b) | $K_i$(h-V1a)/$K_i$(h-V1b) |
|---|---|---|
| + | >10-100 nM | 10-<25 |
| ++ | 1-10 nM | 25-75 |
| +++ | <1 nM | >75 |

We claim:

1. A compound of the formula (I)

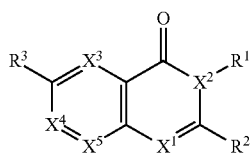

wherein $X^1$, $X^2$, $X^3$, $X^4$ and $X^5$, independently of each other, are N or CH;

$R^1$ is $C_1$-$C_4$-alkyl which carries a group —C(=O)$R^4$ or fluorinated $C_1$-$C_4$-alkyl which carries a group —C(=O)$R^4$;

$R^2$ is phenyl or a 5- or 6-membered heteroaromatic ring with 1, 2 or 3 heteroatoms selected from the group consisting of O, S and N as ring members, where phenyl or the 5- or 6-membered heteroaromatic ring may carry 1, 2 or 3 substituents $R^5$;

$R^3$ is a 3-, 4-, 5- or 6-membered saturated or partially unsaturated carbocyclic ring which carries one substituent $R^6$ and which may additionally carry 1 or 2 substituents $R^7$;

$R^4$ is $OR^8$ or —$NR^9R^{10}$;

each $R^5$ is independently halogen, cyano, nitro, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_3$-$C_8$-cycloalkoxy, fluorinated $C_3$-$C_8$-cycloalkoxy, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)-aminocarbonyl, phenyl, phenyl-$C_1$-$C_2$-alkyl, or a 3-, 4-, 5-, 6-, 7- or 8-membered saturated, partially unsaturated or maximally unsaturated heterocyclic ring containing 1, 2 or 3 heteroatoms or heteroatom groups selected from the group consisting of: O, S, N, NO, SO and $SO_2$ as ring members, where phenyl, phenyl-$C_1$-$C_2$-alkyl and the heterocyclic ring may carry one or more radicals $R^{13}$;
or
two radicals $R^5$, bound on adjacent ring atoms, form together with the ring atoms to which they are bound a saturated or unsaturated 3-, 4-, 5-, 6-, 7-, 8- or 9-membered ring, wherein the ring may contain 1 or 2 heteroatoms or heteroatom groups selected from the group consisting of O, S, N, NO, SO and $SO_2$ and/or 1 or 2 C=O groups as ring members, and wherein the ring may be substituted by one or more radicals $R^{13}$;

$R^6$ is $C_1$-$C_4$-alkyl which carries a radical —$NR^{11}R^{12}$ or fluorinated $C_1$-$C_4$-alkyl, which carries a radical —$NR^{11}R^{12}$;

each $R^7$ is independently halogen, cyano, hydroxyl, $C_1$-$C_4$-alkyl, fluorinated $C_1$-$C_4$-alkyl, $C_1$-$C_4$-alkoxy, or fluorinated $C_1$-$C_4$-alkoxy, or two radicals $R^7$ bound on the same carbon ring atom form together a group =O (oxo);

$R^8$ is hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; phenyl, phenyl-$C_1$-$C_2$-alkyl, or a 3-, 4-, 5-, 6-, 7- or 8-membered saturated, partially unsaturated or maximally unsaturated heterocyclic ring containing 1, 2 or 3 heteroatoms or heteroatom groups selected from the group consisting of: O, S, N, NO, SO and $SO_2$ as ring members, where phenyl, phenyl-$C_1$-$C_2$-alkyl and the heterocyclic ring may carry one or more radicals $R^{13}$;

$R^9$ and $R^{10}$, independently of each other, are hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_1$-$C_6$-alkoxy, fluorinated $C_1$-$C_6$-alkoxy, phenyl, phenyl-$C_1$-$C_2$-alkyl, or a 3-, 4-, 5-, 6-, 7- or 8-membered saturated, partially unsaturated or maximally unsaturated heterocyclic ring containing 1, 2 or 3 heteroatoms or heteroatom groups selected from the group consisting of: O, S, N, NO, SO and $SO_2$ as ring members, where phenyl, phenyl-$C_1$-$C_2$-alkyl and the heterocyclic ring may carry one or more radicals $R^{13}$;
or
$R^9$ and $R^{10}$, together with the nitrogen atom they are bound to, form a 3-, 4-, 5-, 6-, 7- or 8-membered saturated, partially unsaturated or maximally unsaturated heterocyclic ring, where the heterocyclic ring may additionally contain 1 or 2 heteroatoms or heteroatom groups selected from the group consisting of: O, S, N, NO, SO, $SO_2$ and C=O as ring members, and where the heterocyclic ring may carry 1, 2, 3 or 4 radicals $R^{13}$;

$R^{11}$ and $R^{12}$, independently of each other, are hydrogen, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, where the 8 last-mentioned aliphatic and cycloaliphatic radicals may carry one or more radicals $R^{15}$; $C_1$-$C_6$-alkoxy, fluorinated $C_1$-$C_6$-alkoxy, phenyl, phenyl-$C_1$-$C_2$-alkyl, or a 3-, 4-, 5-, 6-, 7- or 8-membered saturated, partially unsaturated or maximally unsaturated heterocyclic ring containing 1, 2 or 3 heteroatoms or heteroatom groups selected from the group consisting of: O, S, N, NO, SO and $SO_2$ as ring members, where phenyl, phenyl-$C_1$-$C_2$-alkyl and the heterocyclic ring may carry one or more radicals $R^{13}$; or $R^{11}$ and $R^{12}$, together with the nitrogen atom they are bound to, form a 3-, 4-, 5-, 6-, 7- or 8-membered saturated, partially unsaturated or maximally unsaturated heterocyclic ring, where the heterocyclic ring may additionally contain 1 or 2 heteroatoms or heteroatom groups selected from the group consisting of: O, S, N, NO, SO, $SO_2$ and C=O as ring members, and where the heterocyclic ring may carry 1, 2, 3 or 4 radicals $R^{13}$;

each $R^{13}$ is independently halogen, cyano, hydroxyl, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkyl-$C_1$-$C_4$-alkyl, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)-aminocarbonyl, phenyl, or phenyl-$C_1$-$C_2$-alkyl; or two radicals $R^{13}$ bound to the same carbon ring atom together a group =O or =S; or two radicals $R^{13}$ bound to the same carbon ring atom may form together with this carbon ring atom a 3-, 4-, 5-, 6-, 7- or 8-membered saturated, partially unsaturated or maximally unsaturated ring, where the ring may contain 1, 2, 3 or 4 heteroatoms or heteroatom-containing groups selected from the group consisting of O, S, N, NO, SO, $SO_2$ and C=O as ring members, and where the ring may be substituted with one or more substituents $R^{14}$; or two non-geminal radicals $R^{13}$ form together a group —$(CH_2)_k$—, where k is 1, 2, 3 or 4, where 1 or 2 hydrogen atoms in this group may be replaced by a methyl group; or two vicinal radicals $R^{13}$ form together a group —CH=CH—CH=CH—;

each $R^{14}$ is independently halogen, cyano, hydroxyl, $C_1$-$C_4$-alkyl, fluorinated $C_1$-$C_4$-alkyl, $C_1$-$C_4$-alkoxy, or fluorinated $C_1$-$C_4$-alkoxy; and each $R^{15}$ is independently cyano, hydroxyl, nitro, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, amino, $C_1$-$C_6$-alkylamino, di-($C_1$-$C_6$-alkyl)-amino, $C_1$-$C_6$-alkylcarbonyl, fluorinated $C_1$-$C_6$-alkylcarbonyl, carboxyl, $C_1$-$C_6$-alkoxycarbonyl, fluorinated $C_1$-$C_6$-alkoxycarbonyl, $C_1$-$C_6$-alkylcarbonyloxy, fluorinated $C_1$-$C_6$-alkylcarbonyloxy, aminocarbonyl, $C_1$-$C_6$-alkylaminocarbonyl, di-($C_1$-$C_6$-alkyl)-aminocarbonyl, phenyl, or a 3-, 4-, 5-, 6-, 7- or 8-membered saturated, partially unsaturated or maximally unsaturated heterocyclic ring containing 1, 2 or 3 heteroatoms or heteroatom groups selected from the group consisting of O, S, N, NO, SO and $SO_2$ as ring members, where phenyl, phenyl-$C_1$-$C_2$-alkyl and the heterocyclic ring may carry one or more radicals $R^{13}$; and $R^{15}$ as a substituent on a cycloaliphatic ring is additionally $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, or phenyl-$C_1$-$C_2$-alkyl, where the phenyl moiety in phenyl-$C_1$-$C_2$-alkyl may carry one or more radicals $R^{13}$;

or an N-oxide, stereoisomer, or a pharmaceutically acceptable salt thereof, or the compound of the formula I, wherein at least one of the atoms has been replaced by its stable, non-radioactive isotope.

2. The compound of claim 1, where $X^1$ is N.

3. The compound of claim 1, where $X^2$ is N.

4. The compound of claim 1, where $X^3$, $X^4$ and $X^5$ are CH.

5. The compound of claim 1, where $R^1$ is $C_1$-$C_4$-alkyl which carries a group —C(=O)$R^4$.

6. The compound of claim 1, where $R^4$ is $OR^8$, where $R^8$ is hydrogen, $C_1$-$C_4$-alkyl or fluorinated $C_1$-$C_4$-alkyl.

7. The compound of claim 1, where $R^4$ is $NR^9R^{10}$, where $R^9$ and $R^{10}$, independently of each other, are hydrogen, $C_1$-$C_6$-alkyl, fluorinated $C_1$-$C_6$-alkyl, $C_2$-$C_4$-alkenyl, fluorinated $C_2$-$C_4$-alkenyl, $C_2$-$C_4$-alkynyl, fluorinated $C_2$-$C_4$-alkynyl, $C_3$-$C_8$-cycloalkyl, fluorinated $C_3$-$C_8$-cycloalkyl, or $C_3$-$C_8$-cycloalkyl-$C_1$-$C_4$-alkyl.

8. The compound of claim 7, where $R^9$ is hydrogen or $C_1$-$C_4$-alkyl; and $R^{10}$ is hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, or $C_3$-$C_6$-cycloalkyl-$C_1$-$C_4$-alkyl.

9. The compound of claim 1, where $R^2$ is phenyl which may carry 1, 2 or 3 substituents $R^5$.

10. The compound of claim 9, where $R^2$ is phenyl which carries one substituent $R^5$ bound in meta-position.

11. The compound of claim 1, where each $R^5$ is independently halogen, cyano, nitro, hydroxyl, $C_1$-$C_6$-alkyl, fluorinated $C_1$-$C_6$-alkyl, $C_1$-$C_6$-alkoxy, or fluorinated $C_1$-$C_6$-alkoxy.

12. The compound of claim 1, where $R^3$ is $C_3$-$C_4$-cycloalkyl or $C_3$-$C_4$-cycloalkenyl which carries one substituent $R^6$.

13. The compound of claim 1, where $R^6$ is $C_1$-$C_4$-alkyl which carries a radical —$NR^{11}R^{12}$.

14. The compound of claim 1, where $R^{11}$ and $R^{12}$, independently of each other, are hydrogen, $C_1$-$C_6$-alkyl, or fluorinated $C_1$-$C_6$-alkyl; or $R^{11}$ and $R^{12}$, together with the nitrogen atom they are bound to, form a 3-, 4-, 5-, 6-, 7- or 8-membered saturated or partially unsaturated heterocyclic ring, where the heterocyclic ring may additionally contain 1 or 2 heteroatoms or heteroatom groups selected from the group consisting of: O, S, N, NO, SO and $SO_2$ as ring members, and where the heterocyclic ring may carry 1, 2, 3 or 4 radicals $R^{13}$.

15. The compound of claim 14, where $R^{11}$ and $R^{12}$, independently of each other, are hydrogen or $C_1$-$C_6$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom or heteroatom group selected from the group consisting of: O, S, N, NO, SO and $SO_2$ as ring member, and where the heterocyclic ring may carry 1, 2, 3 or 4 radicals $R^{13}$.

16. The compound of claim 15, where $R^{11}$ and $R^{12}$, independently of each other, are $C_1$-$C_4$-alkyl; or $R^{11}$ and $R^{12}$, together with the nitrogen atom they are bound to, form a 4-, 5-, 6- or 7-membered saturated or partially unsaturated heterocyclic ring, where the heterocyclic ring may additionally contain one heteroatom selected from the group consisting of: O and S as ring member, and where the heterocyclic ring may carry 1, 2, 3 or 4 radicals $R^{13}$.

17. The compound of claim 1, where each $R^{13}$ is independently halogen, cyano, hydroxyl, $C_1$-$C_4$-alkyl, fluorinated $C_1$-$C_4$-alkyl, $C_1$-$C_4$-alkoxy, or fluorinated $C_1$-$C_4$-alkoxy; or two radicals $R^{13}$ bound to the same carbon ring atom may form together with this carbon ring atom a 3-, 4-, 5- or 6-membered saturated ring, where the ring may contain 1 or 2 heteroatoms or heteroatom-containing groups selected from the group consisting of: O, S, N, NO, SO and $SO_2$ as ring members; or two non-geminal radicals $R^{13}$ form together a group —$(CH_2)_k$—, where k is 1, 2, 3 or 4.

18. The compound of claim 17, where each $R^{13}$ is independently halogen, cyano, hydroxyl, $C_1$-$C_4$-alkyl, fluorinated $C_1$-$C_4$-alkyl, $C_1$-$C_4$-alkoxy, or fluorinated $C_1$-$C_4$-alkoxy; or two radicals $R^{13}$ bound to the same carbon ring atom may form together with this carbon ring atom a 4- or 6-membered saturated heterocyclic ring, where the heterocyclic ring contains 1 oxygen atom as ring member; or two non-geminal radicals $R^{13}$ form together a group —$(CH_2)_k$—, where k is 1 or 2.

19. A compound selected from the group consisting of:
2-(2-(3-chlorophenyl)-4-oxo-6-(3-(piperidin-1-ylmethyl)cyclobut-1-en-1-yl)quinazolin-3(4H)-yl)-N-isopropylacetamide;
2-[2-(3-chlorophenyl)-4-oxo-6-[3-(1-piperidylmethyl)cyclobutyl]quinazolin-3-yl]-N-isopropyl-acetamide;
cis-2-[2-(3-chlorophenyl)-4-oxo-6-[3-(1-piperidylmethyl)cyclobutyl]quinazolin-3-yl]-N-isopropyl-acetamide;
trans-2-[2-(3-chlorophenyl)-4-oxo-6-[3-(1-piperidylmethyl)cyclobutyl]quinazolin-3-yl]-N-isopropyl-acetamide;
2-[2-(3-chlorophenyl)-4-oxo-6-[2-[2-(1-piperidyl)ethyl]cyclopropyl]quinazolin-3-yl]-N-isopropyl-acetamide;
cis-2-[2-(3-chlorophenyl)-4-oxo-6-[2-[2-(1-piperidyl)ethyl]cyclopropyl]quinazolin-3-yl]-N-isopropyl-acetamide;
trans-2-[2-(3-chlorophenyl)-4-oxo-6-[2-[2-(1-piperidyl)ethyl]cyclopropyl]quinazolin-3-yl]-N-isopropyl-acetamide;
2-[2-(3-chlorophenyl)-4-oxo-6-[2-(1-piperidylmethyl)cyclopropyl]quinazolin-3-yl]-N-isopropyl-acetamide;
cis-2-[2-(3-chlorophenyl)-4-oxo-6-[2-(1-piperidylmethyl)cyclopropyl]quinazolin-3-yl]-N-isopropyl-acetamide;
trans-2-[2-(3-chlorophenyl)-4-oxo-6-[2-(1-piperidylmethyl)cyclopropyl]quinazolin-3-yl]-N-isopropyl-acetamide;
methyl 2-[2-(3-chlorophenyl)-4-oxo-6-[3-(1-piperidylmethyl)cyclobutyl]quinazolin-3-yl]acetate;
cis-methyl 2-[2-(3-chlorophenyl)-4-oxo-6-[3-(1-piperidylmethyl)cyclobutyl]quinazolin-3-yl]acetate;
trans-methyl 2-[2-(3-chlorophenyl)-4-oxo-6-[3-(1-piperidylmethyl)cyclobutyl]quinazolin-3-yl]acetate;
2-[2-(3-chlorophenyl)-4-oxo-6-(3-(piperidin-1-ylmethyl)cyclobutyl]quinazolin-3(4H)-yl]acetic acid;
cis-2-[2-(3-chlorophenyl)-4-oxo-6-(3-(piperidin-1-ylmethyl)cyclobutyl]quinazolin-3(4H)-yl]acetic acid;
trans-2-[2-(3-chlorophenyl)-4-oxo-6-(3-(piperidin-1-ylmethyl)cyclobutyl]quinazolin-3(4H)-yl]acetic acid;
2-[2-(3-chlorophenyl)-6-[3-[(4-cyano-1-piperidyl)methyl]cyclobutyl]-4-oxo-quinazolin-3-yl]-N-isopropyl-acetamide;
cis-2-[2-(3-chlorophenyl)-6-[3-[(4-cyano-1-piperidyl)methyl]cyclobutyl]-4-oxo-quinazolin-3-yl]-N-isopropyl-acetamide;
trans-2-[2-(3-chlorophenyl)-6-[3-[(4-cyano-1-piperidyl)methyl]cyclobutyl]-4-oxo-quinazolin-3-yl]-N-isopropyl-acetamide;
2-[2-(3-chlorophenyl)-4-oxo-6-[3-(thiomorpholinomethyl)cyclobutyl]quinazolin-3-yl]-N-isopropyl-acetamide;
cis-2-[2-(3-chlorophenyl)-4-oxo-6-[3-(thiomorpholinomethyl)cyclobutyl]quinazolin-3-yl]-N-isopropyl-acetamide;
trans-2-[2-(3-chlorophenyl)-4-oxo-6-[3-(thiomorpholinomethyl)cyclobutyl]quinazolin-3-yl]-N-isopropyl-acetamide;
2-[2-(3-chlorophenyl)-4-oxo-6-[3-(pyrrolidin-1-ylmethyl)cyclobutyl]quinazolin-3-yl]-N-isopropyl-acetamide;
cis-2-[2-(3-chlorophenyl)-4-oxo-6-[3-(pyrrolidin-1-ylmethyl)cyclobutyl]quinazolin-3-yl]-N-isopropyl-acetamide;
trans-2-[2-(3-chlorophenyl)-4-oxo-6-[3-(pyrrolidin-1-ylmethyl)cyclobutyl]quinazolin-3-yl]-N-isopropyl-acetamide;
2-[2-(3-chlorophenyl)-6-[3-[(4-methoxy-1-piperidyl)methyl]cyclobutyl]-4-oxo-quinazolin-3-yl]-N-isopropyl-acetamide;
cis-2-[2-(3-chlorophenyl)-6-[3-[(4-methoxy-1-piperidyl)methyl]cyclobutyl]-4-oxo-quinazolin-3-yl]-N-isopropyl-acetamide;
trans-2-[2-(3-chlorophenyl)-6-[3-[(4-methoxy-1-piperidyl)methyl]cyclobutyl]-4-oxo-quinazolin-3-yl]-N-isopropyl-acetamide;
2-[2-(3-chlorophenyl)-6-[3-[[(3R)-3-fluoropyrrolidin-1-yl]methyl]cyclobutyl]-4-oxo-quinazolin-3-yl]-N-isopropyl-acetamide;
cis-2-[2-(3-chlorophenyl)-6-[3-[[(3R)-3-fluoropyrrolidin-1-yl]methyl]cyclobutyl]-4-oxo-quinazolin-3-yl]-N-isopropyl-acetamide;
trans-2-[2-(3-chlorophenyl)-6-[3-[[(3R)-3-fluoropyrrolidin-1-yl]methyl]cyclobutyl]-4-oxo-quinazolin-3-yl]-N-isopropyl-acetamide;
2-[2-(3-chlorophenyl)-6-[3-[(4,4-difluoro-1-piperidyl)methyl]cyclobutyl]-4-oxo-quinazolin-3-yl]-N-isopropyl-acetamide;
cis-2-[2-(3-chlorophenyl)-6-[3-[(4,4-difluoro-1-piperidyl)methyl]cyclobutyl]-4-oxo-quinazolin-3-yl]-N-isopropyl-acetamide;
trans-2-[2-(3-chlorophenyl)-6-[3-[(4,4-difluoro-1-piperidyl)methyl]cyclobutyl]-4-oxo-quinazolin-3-yl]-N-isopropyl-acetamide;
2-[2-(3-chlorophenyl)-6-[3-(morpholinomethyl)cyclobutyl]-4-oxo-quinazolin-3-yl]-N-isopropyl-acetamide;
cis-2-[2-(3-chlorophenyl)-6-[3-(morpholinomethyl)cyclobutyl]-4-oxo-quinazolin-3-yl]-N-isopropyl-acetamide;

trans-2-[2-(3-chlorophenyl)-6-[3-(morpholinomethyl)cyclobutyl]-4-oxo-quinazolin-3-yl]-N-isopropyl-acetamide;
2-[2-(3-chlorophenyl)-6-[3-[(3-cyano-1-piperidyl)methyl]cyclobutyl]-4-oxo-quinazolin-3-yl]-N-isopropyl-acetamide;
cis-2-[2-(3-chlorophenyl)-6-[3-[(3-cyano-1-piperidyl)methyl]cyclobutyl]-4-oxo-quinazolin-3-yl]-N-isopropyl-acetamide;
trans-2-[2-(3-chlorophenyl)-6-[3-[(3-cyano-1-piperidyl)methyl]cyclobutyl]-4-oxo-quinazolin-3-yl]-N-isopropyl-acetamide;
2-[2-(3-chlorophenyl)-6-[3-(diethylaminomethyl)cyclobutyl]-4-oxo-quinazolin-3-yl]-N-isopropyl-acetamide;
cis-2-[2-(3-chlorophenyl)-6-[3-(diethylaminomethyl)cyclobutyl]-4-oxo-quinazolin-3-yl]-N-isopropyl-acetamide;
trans-2-[2-(3-chlorophenyl)-6-[3-(diethylaminomethyl)cyclobutyl]-4-oxo-quinazolin-3-yl]-N-isopropyl-acetamide;
2-[2-(3-chlorophenyl)-6-[3-[[(3S)-3-fluoropyrrolidin-1-yl]methyl]cyclobutyl]-4-oxo-quinazolin-3-yl]-N-isopropyl-acetamide;
cis-2-[2-(3-chlorophenyl)-6-[3-[[(3S)-3-fluoropyrrolidin-1-yl]methyl]cyclobutyl]-4-oxo-quinazolin-3-yl]-N-isopropyl-acetamide;
trans-2-[2-(3-chlorophenyl)-6-[3-[[(3S)-3-fluoropyrrolidin-1-yl]methyl]cyclobutyl]-4-oxo-quinazolin-3-yl]-N-isopropyl-acetamide;
2-[2-(3-chlorophenyl)-6-[3-(dimethylaminomethyl)cyclobutyl]-4-oxo-quinazolin-3-yl]-N-isopropyl-acetamide;
cis-2-[2-(3-chlorophenyl)-6-[3-(dimethylaminomethyl)cyclobutyl]-4-oxo-quinazolin-3-yl]-N-isopropyl-acetamide;
trans-2-[2-(3-chlorophenyl)-6-[3-(dimethylaminomethyl)cyclobutyl]-4-oxo-quinazolin-3-yl]-N-isopropyl-acetamide;
2-[2-(3-chlorophenyl)-6-[3-(3,6-dihydro-2H-pyridin-1-ylmethyl)cyclobutyl]-4-oxo-quinazolin-3-yl]-N-isopropyl-acetamide;
cis-2-[2-(3-chlorophenyl)-6-[3-(3,6-dihydro-2H-pyridin-1-ylmethyl)cyclobutyl]-4-oxo-quinazolin-3-yl]-N-isopropyl-acetamide;
trans-2-[2-(3-chlorophenyl)-6-[3-(3,6-dihydro-2H-pyridin-1-ylmethyl)cyclobutyl]-4-oxo-quinazolin-3-yl]-N-isopropyl-acetamide;
2-[2-(3-chlorophenyl)-6-[3-[(3-fluoroazetidin-1-yl)methyl]cyclobutyl]-4-oxo-quinazolin-3-yl]-N-isopropyl-acetamide;
cis-2-[2-(3-chlorophenyl)-6-[3-[(3-fluoroazetidin-1-yl)methyl]cyclobutyl]-4-oxo-quinazolin-3-yl]-N-isopropyl-acetamide;
trans-2-[2-(3-chlorophenyl)-6-[3-[(3-fluoroazetidin-1-yl)methyl]cyclobutyl]-4-oxo-quinazolin-3-yl]-N-isopropyl-acetamide;
2-[2-(3-chlorophenyl)-6-[3-[(4-ethoxy-1-piperidyl)methyl]cyclobutyl]-4-oxo-quinazolin-3-yl]-N-isopropyl-acetamide;
cis-2-[2-(3-chlorophenyl)-6-[3-[(4-ethoxy-1-piperidyl)methyl]cyclobutyl]-4-oxo-quinazolin-3-yl]-N-isopropyl-acetamide;
trans-2-[2-(3-chlorophenyl)-6-[3-[(4-ethoxy-1-piperidyl)methyl]cyclobutyl]-4-oxo-quinazolin-3-yl]-N-isopropyl-acetamide;
2-[6-[3-(azepan-1-ylmethyl)cyclobutyl]-2-(3-chlorophenyl)-4-oxo-quinazolin-3-yl]-N-isopropyl-acetamide;
cis-2-[6-[3-(azepan-1-ylmethyl)cyclobutyl]-2-(3-chlorophenyl)-4-oxo-quinazolin-3-yl]-N-isopropyl-acetamide;
trans-2-[6-[3-(azepan-1-ylmethyl)cyclobutyl]-2-(3-chlorophenyl)-4-oxo-quinazolin-3-yl]-N-isopropyl-acetamide;
2-[2-(3-chlorophenyl)-6-[3-[(4-methyl-1-piperidyl)methyl]cyclobutyl]-4-oxo-quinazolin-3-yl]-N-isopropyl-acetamide;
cis-2-[2-(3-chlorophenyl)-6-[3-[(4-methyl-1-piperidyl)methyl]cyclobutyl]-4-oxo-quinazolin-3-yl]-N-isopropyl-acetamide;
trans-2-[2-(3-chlorophenyl)-6-[3-[(4-methyl-1-piperidyl)methyl]cyclobutyl]-4-oxo-quinazolin-3-yl]-N-isopropyl-acetamide;
2-[2-(3-chlorophenyl)-6-[3-[(3-hydroxy-8-azabicyclo[3.2.1]octan-8-yl)methyl]cyclobutyl]-4-oxo-quinazolin-3-yl]-N-isopropyl-acetamide;
cis-2-[2-(3-chlorophenyl)-6-[3-[(3-hydroxy-8-azabicyclo[3.2.1]octan-8-yl)methyl]cyclobutyl]-4-oxo-quinazolin-3-yl]-N-isopropyl-acetamide;
trans-2-[2-(3-chlorophenyl)-6-[3-[(3-hydroxy-8-azabicyclo[3.2.1]octan-8-yl)methyl]cyclobutyl]-4-oxo-quinazolin-3-yl]-N-isopropyl-acetamide;
2-[2-(3-chlorophenyl)-6-[3-[[(3S)-3-methylpyrrolidin-1-yl]methyl]cyclobutyl]-4-oxo-quinazolin-3-yl]-N-isopropyl-acetamide;
cis-2-[2-(3-chlorophenyl)-6-[3-[[(3S)-3-methylpyrrolidin-1-yl]methyl]cyclobutyl]-4-oxo-quinazolin-3-yl]-N-isopropyl-acetamide;
trans-2-[2-(3-chlorophenyl)-6-[3-[[(3S)-3-methylpyrrolidin-1-yl]methyl]cyclobutyl]-4-oxo-quinazolin-3-yl]-N-isopropyl-acetamide;
2-[2-(3-chlorophenyl)-6-[3-(1,4-oxazepan-4-ylmethyl)cyclobutyl]-4-oxo-quinazolin-3-yl]-N-isopropyl-acetamide;
cis-2-[2-(3-chlorophenyl)-6-[3-(1,4-oxazepan-4-ylmethyl)cyclobutyl]-4-oxo-quinazolin-3-yl]-N-isopropyl-acetamide;
trans-2-[2-(3-chlorophenyl)-6-[3-(1,4-oxazepan-4-ylmethyl)cyclobutyl]-4-oxo-quinazolin-3-yl]-N-isopropyl-acetamide;
N-tert-butyl-2-[2-(3-chlorophenyl)-4-oxo-6-[3-(1-piperidylmethyl)cyclobutyl]quinazolin-3-yl]acetamide;
cis-N-tert-butyl-2-[2-(3-chlorophenyl)-4-oxo-6-[3-(1-piperidylmethyl)cyclobutyl]-quinazolin-3-yl]acetamide;
trans-N-tert-butyl-2-[2-(3-chlorophenyl)-4-oxo-6-[3-(1-piperidylmethyl)cyclo-butyl]quinazolin-3-yl]acetamide;
2-[2-(3-chlorophenyl)-4-oxo-6-[3-(1-piperidylmethyl)cyclobutyl]quinazolin-3-yl]-N-cyclopropyl-acetamide;
cis-2-[2-(3-chlorophenyl)-4-oxo-6-[3-(1-piperidylmethyl)cyclobutyl]quinazolin-3-yl]-N-cyclopropyl-acetamide;
trans-2-[2-(3-chlorophenyl)-4-oxo-6-[3-(1-piperidylmethyl)cyclobutyl]quinazolin-3-yl]-N-cyclopropyl-acetamide;
2-[2-(3-chlorophenyl)-4-oxo-6-[3-(1-piperidylmethyl)cyclobutyl]quinazolin-3-yl]-N-propyl-acetamide;
cis-2-[2-(3-chlorophenyl)-4-oxo-6-[3-(1-piperidylmethyl)cyclobutyl]quinazolin-3-yl]-N-propyl-acetamide;
trans-2-[2-(3-chlorophenyl)-4-oxo-6-[3-(1-piperidylmethyl)cyclobutyl]quinazolin-3-yl]-N-propyl-acetamide;

2-[2-(3-chlorophenyl)-4-oxo-6-[3-(1-piperidylmethyl)cyclobutyl]quinazolin-3-yl]-N-(cyclopropylmethyl)acetamide;

cis-2-[2-(3-chlorophenyl)-4-oxo-6-[3-(1-piperidylmethyl)cyclobutyl]quinazolin-3-yl]-N-(cyclopropylmethyl)acetamide;

trans-2-[2-(3-chlorophenyl)-4-oxo-6-[3-(1-piperidylmethyl)cyclobutyl]quinazolin-3-yl]-N-(cyclopropylmethyl)acetamide;

2-[2-(3-chlorophenyl)-6-[3-[(4-fluoro-1-piperidyl)methyl]cyclobutyl]-4-oxo-quinazolin-3-yl]-N-isopropyl-acetamide;

cis-2-[2-(3-chlorophenyl)-6-[3-[(4-fluoro-1-piperidyl)methyl]cyclobutyl]-4-oxo-quinazolin-3-yl]-N-isopropyl-acetamide;

trans-2-[2-(3-chlorophenyl)-6-[3-[(4-fluoro-1-piperidyl)methyl]cyclobutyl]-4-oxo-quinazolin-3-yl]-N-isopropyl-acetamide;

2-[2-(3-chlorophenyl)-6-[3-(6-oxa-2-azaspiro[3.3]heptan-2-ylmethyl)cyclobutyl]-4-oxo-quinazolin-3-yl]-N-isopropyl-acetamide;

cis-2-[2-(3-chlorophenyl)-6-[3-(6-oxa-2-azaspiro[3.3]heptan-2-ylmethyl)cyclobutyl]-4-oxo-quinazolin-3-yl]-N-isopropyl-acetamide;

trans-2-[2-(3-chlorophenyl)-6-[3-(6-oxa-2-azaspiro[3.3]heptan-2-ylmethyl)cyclobutyl]-4-oxo-quinazolin-3-yl]-N-isopropyl-acetamide;

2-[2-(3-chlorophenyl)-6-[3-[(4-hydroxy-1-piperidyl)methyl]cyclobutyl]-4-oxo-quinazolin-3-yl]-N-isopropyl-acetamide;

cis-2-[2-(3-chlorophenyl)-6-[3-[(4-hydroxy-1-piperidyl)methyl]cyclobutyl]-4-oxo-quinazolin-3-yl]-N-isopropyl-acetamide;

trans-2-[2-(3-chlorophenyl)-6-[3-[(4-hydroxy-1-piperidyl)methyl]cyclobutyl]-4-oxo-quinazolin-3-yl]-N-isopropyl-acetamide;

2-[2-(3-chlorophenyl)-6-[3-[[(3R)-3-hydroxy-1-piperidyl]methyl]cyclobutyl]-4-oxo-quinazolin-3-yl]-N-isopropyl-acetamide;

cis-2-[2-(3-chlorophenyl)-6-[3-[[(3R)-3-hydroxy-1-piperidyl]methyl]cyclobutyl]-4-oxo-quinazolin-3-yl]-N-isopropyl-acetamide;

trans-2-[2-(3-chlorophenyl)-6-[3-[[(3R)-3-hydroxy-1-piperidyl]methyl]cyclobutyl]-4-oxo-quinazolin-3-yl]-N-isopropyl-acetamide;

2-[2-(3-chlorophenyl)-6-[3-[[(3R)-3-methylpyrrolidin-1-yl]methyl]cyclobutyl]-4-oxo-quinazolin-3-yl]-N-isopropyl-acetamide;

cis-2-[2-(3-chlorophenyl)-6-[3-[[(3R)-3-methylpyrrolidin-1-yl]methyl]cyclobutyl]-4-oxo-quinazolin-3-yl]-N-isopropyl-acetamide;

trans-2-[2-(3-chlorophenyl)-6-[3-[[(3R)-3-methylpyrrolidin-1-yl]methyl]cyclobutyl]-4-oxo-quinazolin-3-yl]-N-isopropyl-acetamide;

2-[2-(3-chlorophenyl)-6-[3-[(3-methoxyazetidin-1-yl)methyl]cyclobutyl]-4-oxo-quinazolin-3-yl]-N-isopropyl-acetamide;

cis-2-[2-(3-chlorophenyl)-6-[3-[(3-methoxyazetidin-1-yl)methyl]cyclobutyl]-4-oxo-quinazolin-3-yl]-N-isopropyl-acetamide;

trans-2-[2-(3-chlorophenyl)-6-[3-[(3-methoxyazetidin-1-yl)methyl]cyclobutyl]-4-oxo-quinazolin-3-yl]-N-isopropyl-acetamide;

2-[2-(3-chlorophenyl)-6-[3-[(4-hydroxy-4-methyl-1-piperidyl)methyl]cyclobutyl]-4-oxo-quinazolin-3-yl]-N-isopropyl-acetamide;

cis-2-[2-(3-chlorophenyl)-6-[3-[(4-hydroxy-4-methyl-1-piperidyl)methyl]cyclobutyl]-4-oxo-quinazolin-3-yl]-N-isopropyl-acetamide;

trans-2-[2-(3-chlorophenyl)-6-[3-[(4-hydroxy-4-methyl-1-piperidyl)methyl]cyclobutyl]-4-oxo-quinazolin-3-yl]-N-isopropyl-acetamide;

2-[2-(3-chlorophenyl)-6-[3-[[(3S)-3-hydroxy-1-piperidyl]methyl]cyclobutyl]-4-oxo-quinazolin-3-yl]-N-isopropyl-acetamide;

cis-2-[2-(3-chlorophenyl)-6-[3-[[(3S)-3-hydroxy-1-piperidyl]methyl]cyclobutyl]-4-oxo-quinazolin-3-yl]-N-isopropyl-acetamide;

trans-2-[2-(3-chlorophenyl)-6-[3-[[(3S)-3-hydroxy-1-piperidyl]methyl]cyclobutyl]-4-oxo-quinazolin-3-yl]-N-isopropyl-acetamide;

2-[2-(3-chlorophenyl)-4-oxo-6-[3-[[4-(trifluoromethyl)-1-piperidyl]methyl]-cyclobutyl]quinazolin-3-yl]-N-isopropyl-acetamide;

cis-2-[2-(3-chlorophenyl)-4-oxo-6-[3-[[4-(trifluoromethyl)-1-piperidyl]methyl]-cyclobutyl]quinazolin-3-yl]-N-isopropyl-acetamide;

trans-2-[2-(3-chlorophenyl)-4-oxo-6-[3-[[4-(trifluoromethyl)-1-piperidyl]methyl]-cyclobutyl]quinazolin-3-yl]-N-isopropyl-acetamide;

2-[2-(3-chlorophenyl)-6-[3-[(3-fluoro-1-piperidyl)methyl]cyclobutyl]-4-oxo-quinazolin-3-yl]-N-isopropyl-acetamide;

cis-2-[2-(3-chlorophenyl)-6-[3-[(3-fluoro-1-piperidyl)methyl]cyclobutyl]-4-oxo-quinazolin-3-yl]-N-isopropyl-acetamide;

trans-2-[2-(3-chlorophenyl)-6-[3-[(3-fluoro-1-piperidyl)methyl]cyclobutyl]-4-oxo-quinazolin-3-yl]-N-isopropyl-acetamide;

2-[2-(3-chlorophenyl)-6-[3-[(3-hydroxyazetidin-1-yl)methyl]cyclobutyl]-4-oxo-quinazolin-3-yl]-N-isopropyl-acetamide;

cis-2-[2-(3-chlorophenyl)-6-[3-[(3-hydroxyazetidin-1-yl)methyl]cyclobutyl]-4-oxo-quinazolin-3-yl]-N-isopropyl-acetamide;

trans-2-[2-(3-chlorophenyl)-6-[3-[(3-hydroxyazetidin-1-yl)methyl]cyclobutyl]-4-oxo-quinazolin-3-yl]-N-isopropyl-acetamide;

2-[2-(3-chlorophenyl)-6-[3-(7-oxa-2-azaspiro[3.5]nonan-2-ylmethyl)cyclobutyl]-4-oxo-quinazolin-3-yl]-N-isopropyl-acetamide;

cis-2-[2-(3-chlorophenyl)-6-[3-(7-oxa-2-azaspiro[3.5]nonan-2-ylmethyl)cyclobutyl]-4-oxo-quinazolin-3-yl]-N-isopropyl-acetamide;

trans-2-[2-(3-chlorophenyl)-6-[3-(7-oxa-2-azaspiro[3.5]nonan-2-ylmethyl)cyclobutyl]-4-oxo-quinazolin-3-yl]-N-isopropyl-acetamide;

2-[2-(3-chlorophenyl)-6-[3-[[(2S,6R)-2,6-dimethylmorpholin-4-yl]methyl]cyclobutyl]-4-oxo-quinazolin-3-yl]-N-isopropyl-acetamide;

cis-2-[2-(3-chlorophenyl)-6-[3-[[(2S,6R)-2,6-dimethylmorpholin-4-yl]methyl]cyclobutyl]-4-oxo-quinazolin-3-yl]-N-isopropyl-acetamide;

trans-2-[2-(3-chlorophenyl)-6-[3-[[(2S,6R)-2,6-dimethylmorpholin-4-yl]methyl]cyclo-butyl]-4-oxo-quinazolin-3-yl]-N-isopropyl-acetamide;

2-[2-(3-chlorophenyl)-6-[3-[(2,6-dimethylmorpholin-4-yl)methyl]cyclobutyl]-4-oxo-quinazolin-3-yl]-N-isopropyl-acetamide;

cis-2-[2-(3-chlorophenyl)-6-[3-[(2,6-dimethylmorpholin-4-yl)methyl]cyclobutyl]-4-oxo-quinazolin-3-yl]-N-isopropyl-acetamide;

trans-2-[2-(3-chlorophenyl)-6-[3-[(2,6-dimethylmorpholin-4-yl)methyl]cyclobutyl]-4-oxo-quinazolin-3-yl]-N-isopropyl-acetamide;

2-[2-(3-chlorophenyl)-6-[3-[[(3R)-3-methylmorpholin-4-yl]methyl]cyclobutyl]-4-oxo-quinazolin-3-yl]-N-isopropyl-acetamide;

cis-2-[2-(3-chlorophenyl)-6-[3-[[(3R)-3-methylmorpholin-4-yl]methyl]cyclobutyl]-4-oxo-quinazolin-3-yl]-N-isopropyl-acetamide;

trans-2-[2-(3-chlorophenyl)-6-[3-[[(3R)-3-methylmorpholin-4-yl]methyl]cyclobutyl]-4-oxo-quinazolin-3-yl]-N-isopropyl-acetamide;

2-[2-(3-chlorophenyl)-4-oxo-6-[3-(1-piperidylmethyl)cyclobutyl]quinazolin-3-yl]-N-[(1S)-2,2,2-trifluoro-1-methyl-ethyl]acetamide;

cis-2-[2-(3-chlorophenyl)-4-oxo-6-[3-(1-piperidylmethyl)cyclobutyl]quinazolin-3-yl]-N-[(1S)-2,2,2-trifluoro-1-methyl-ethyl]acetamide;

trans-2-[2-(3-chlorophenyl)-4-oxo-6-[3-(1-piperidylmethyl)cyclobutyl]quinazolin-3-yl]-N-[(1S)-2,2,2-trifluoro-1-methyl-ethyl]acetamide;

2-[2-(3-chlorophenyl)-4-oxo-6-[3-(1-piperidylmethyl)cyclobutyl]quinazolin-3-yl]-N-[(1R)-2,2,2-trifluoro-1-methyl-ethyl]acetamide;

cis-2-[2-(3-chlorophenyl)-4-oxo-6-[3-(1-piperidylmethyl)cyclobutyl]quinazolin-3-yl]-N-[(1R)-2,2,2-trifluoro-1-methyl-ethyl]acetamide;

trans-2-[2-(3-chlorophenyl)-4-oxo-6-[3-(1-piperidylmethyl)cyclobutyl]quinazolin-3-yl]-N-[(1R)-2,2,2-trifluoro-1-methyl-ethyl]acetamide;

2-[2-(3-chlorophenyl)-4-oxo-6-[3-[2-(1-piperidyl)ethyl]cyclobutyl]quinazolin-3-yl]-N-isopropyl-acetamide;

cis-2-[2-(3-chlorophenyl)-4-oxo-6-[3-[2-(1-piperidyl)ethyl]cyclobutyl]quinazolin-3-yl]-N-isopropyl-acetamide;

trans-2-[2-(3-chlorophenyl)-4-oxo-6-[3-[2-(1-piperidyl)ethyl]cyclobutyl]quinazolin-3-yl]-N-isopropyl-acetamide; and 2-[2-(3-chlorophenyl)-4-oxo-6-[3-[2-(1-piperidyl)ethyl]cyclobut-2-en-1-yl]quinazolin-3-yl]-N-isopropyl-acetamide;

or an N-oxide, stereoisomer, or a pharmaceutically acceptable salt thereof, or the above compounds, wherein at least one of the atoms has been replaced by its stable, non-radioactive isotope.

20. A pharmaceutical composition comprising a compound of claim 1, or an N-oxide, a stereoisomer or at least one pharmaceutically acceptable salt thereof and at least one pharmaceutically acceptable carrier.

21. A method for the treatment of vasopressin-related diseases, comprising administering an effective amount of a compound of claim 1, or an N oxide, a stereoisomer, or pharmaceutically acceptable salt thereof to a subject in need thereof.

22. The method of claim 21, wherein the vasopressin-related diseases are selected from the group consisting of: diabetes; insulin resistance; nocturnal enuresis; incontinence; hypertension; pulmonary hypertension; heart failure; myocardial infarction; coronary spasm; unstable angina; PTCA (percutaneous transluminal coronary angioplasty); ischemias of the heart; edemas; renal vasospasm; necrosis of the renal cortex; hyponatremia; hypokalemia; Schwartz-Bartter syndrome; gastritic vasospasm; hepatocirrhosis; gastric and intestinal ulcers; emesis; emesis occurring during chemotherapy; travel sickness; affective disorders selected from the group consisting of: depressive disorders, anxiety disorders, obsessive-compulsive disorders, trauma and stressor-related disorders, and bipolar disorders; Alzheimer's disease; mild cognitive impairment and cognitive impairment associated with schizophrenia, aging, Alzheimer disease, Parkinson's disease and/or dementia;

increased aggression in conditions selected from the group consisting of Alzheimer's disease, schizophrenia, bipolar disorder, frontal lobe injuries and substance use disorders; Cushing's syndrome; sleep disorders; substance-related and addictive disorders; schizophrenia and psychosis; pain; and micturition disorders.

23. The method of claim 22,
where substance-related and addictive disorders are selected from the group consisting of: substance use disorder, substance-induced disorder, alcohol use disorder, alcohol intoxication, alcohol withdrawal, caffeine intoxication, caffeine withdrawal, *cannabis* use disorder, *cannabis* withdrawal, phencyclidine use disorder, other hallucinogen use disorders, phencyclidine intoxication, hallucinogen persisting perception disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, and gambling disorder.

24. The method of claim 22, where the depressive disorders are selected from the group consisting of: dysthymic disorders, major depression, seasonal depression, treatment-resistant depression disorders, disruptive mood dysregulation disorder, premenstrual dysphoric disorder, substance/medication-induced depressive disorder, and childhood onset mood disorders;

the anxiety disorders are selected from the group consisting of: phobias, panic disorders, drug withdrawal-induced anxiety disorders, separation anxiety disorder, selective mutism, social anxiety disorder, agoraphobia, and substance/medication-induced anxiety disorder;

the obsessive-compulsive disorders are selected from the group consisting of: obsessive-compulsive disorder, body dysmorphic disorder, hoarding disorder, trichotillomania, excoriation disorder, and substance/medication-induced obsessive-compulsive and related disorder;

the trauma and stressor-related disorders are selected from reactive attachment disorder, disinhibited social engagement disorder, post traumatic stress disorder, acute stress disorder, and adjustment disorder; and the bipolar disorders are selected from the group consisting of: bipolar I disorder, bipolar II disorder, cyclothymic disorder, and substance/medication-induced bipolar disorder.

25. The method of claim 21, where the vasopressin-related diseases are selected from the group consisting of: depressive disorders; anxiety disorders and stress-dependent anxiety disorders; and substance-related and addictive disorders, where the substance-related and addictive disorders are selected from the group consisting of alcohol use disorder, alcohol intoxication, and alcohol withdrawal.

26. The compound of claim 11, where $R^5$ is halogen.

27. The compound of claim 26, where $R^5$ is chlorine.

28. The compound of claim 13, where $R^6$ is $C_1$-$C_2$-alkyl which carries a radical —$NR^{11}R^{12}$.

29. The compound of claim 5, where $R^1$ is —$CH_2$—$C(=O)R^4$.

* * * * *